(12) United States Patent
Al-Murrani

(10) Patent No.: US 7,700,280 B2
(45) Date of Patent: Apr. 20, 2010

(54) METHODS FOR ASSESSING CISPLATIN RESISTANCE, DISEASE PROGRESSION, AND TREATMENT EFFICACY IN OVARIAN CANCER

(75) Inventor: Samer Al-Murrani, Topeka, KS (US)

(73) Assignee: The Penn State Research Foundation, University Park, PA (US)

( * ) Notice: Subject to any disclaimer, the term of this patent is extended or adjusted under 35 U.S.C. 154(b) by 2 days.

(21) Appl. No.: 11/026,734

(22) Filed: Dec. 30, 2004

(65) Prior Publication Data

US 2005/0176669 A1    Aug. 11, 2005

Related U.S. Application Data

(60) Provisional application No. 60/533,505, filed on Dec. 31, 2003.

(51) Int. Cl.
*C12Q 1/68* (2006.01)
*G01N 33/53* (2006.01)
*C12P 19/34* (2006.01)

(52) U.S. Cl. .............................. 435/6; 435/7.1; 435/91.2

(58) Field of Classification Search ........................ None
See application file for complete search history.

(56) References Cited

U.S. PATENT DOCUMENTS

| | | | |
|---|---|---|---|
| 5,624,803 | A | 4/1997 | Noonberg et al. |
| 5,902,880 | A | 5/1999 | Thompson |
| 6,146,886 | A | 11/2000 | Thompson |
| 6,395,713 | B1 | 5/2002 | Beigelman et al. |
| 2002/0051978 | A1* | 5/2002 | Roth et al. ..................... 435/6 |

FOREIGN PATENT DOCUMENTS

| | | |
|---|---|---|
| WO | WO 93/23569 | 11/1993 |
| WO | WO 94/02595 | 2/1994 |
| WO | WO 96/18736 | 6/1996 |
| WO | WO 99/04819 | 2/1999 |
| WO | WO 99/05094 | 2/1999 |
| WO | WO 99/07409 | 2/1999 |
| WO | WO 99/31262 | 6/1999 |
| WO | WO 99/32619 | 7/1999 |
| WO | WO 00/01846 | 1/2000 |
| WO | WO 00/44895 | 8/2000 |
| WO | WO 00/44914 | 8/2000 |
| WO | WO 00/53722 | 9/2000 |
| WO | WO 01/12781 | 2/2001 |
| WO | WO 01/29058 | 4/2001 |
| WO | WO 01/36646 | 5/2001 |
| WO | WO 02/14554 | 2/2002 |
| WO | WO 03/039327 | 5/2003 |

OTHER PUBLICATIONS

Sanchez-Carbayo, M. Use of High-Throughput DNA Microarrays to Identify Biomarkers for Bladder Cancer, Clinical Chemistry 49(1):23-31, 2003.*
Wu, T. Analysing Gene Expression Data From DNA Microarrays to Identify Candidate Genes, J. Pathol. 195(1):53-65, 2001.*
Lucentini, J. Gene Association Studies Typically Wrong, The Scientist 18(24):20, 2004.*
Chen, et al. Discordant Protein and mRNA Expression in Lung Adenocarcinomas, Molecular and Cellular Proteomics 1:304-313, 2002.*
Revision History for BC001410, NCBI Database.*
Samimi et al. cDNA microarray-based identification of genes and pathways associated with oxaliplatin resistance. Cancer Chemother Pharmacol, vol. 55, pp. 1-11, 2005.*
Li et al. Gen expression response to treatment in drug-sensitive and drug-resistant ovarian cancer cells. Oncogene, vol. 26, pp. 2860-2872, 2007.*
Golub et al. Molecular classification of cancer: class discovery and class prediction by gene expression monitoring. Science, vol. 286, pp. 531-537, 1999.*
Sherman-Baust et al. Remodeling of the extracellular matrix through overexpression of collagen VI contributes to cisplatin resistance in ovarian cancer cells. Cancer Cell, vol. 3, pp. 377-386, Apr. 2003.*
Jain et al. Rank-invariant resampling based estimation of false discovery rate for analysis of small sample mircorarray data. BMC Bioinformatics, vol. 6, pp. 187, 2005, printed as pp. 1/9 to 9/9.*
Pusztai and Hess. Clinical trial design for microarray predictive marker discovery and assessment. Annals of Oncology, vol. 15, pp. 1731-1737, 2004.*
Revision History for BC001410, NCBI Database, printed on Jan. 5, 2007.*
Revision History for BC015973, NCBI Database, printed on Jan. 5, 2007.*
Ohuchida, et al., "S100A11, A Putative Tumor Suppressor Gene. is Overexpressed in Pancreatic Carcinogenesis." Clin. Cancer Res., 12(18), pp. 5417-5422, 2006.
Kanamori, et al., "Increased expression of calcium-binding protein S100 in human uterine smooth tumours." Mol. Human Repro., 10(10), pp. 735-742, 2004.
Domoto, et al., "Evaluation of S100A10, annexin II and B-FABP expression as markers for renal cell carcinoma." Cancer Sci., 98(1), pp. 77-82, 2007.
El-Rifai, et al., "Gastric Cancers Overexpress S100A Calcium-binding Proteins." Cancer Res., 62, pp. 6823-6826, 2002.
Zhang, et al., "RNA Interference-mediated Silencing of the S100A10 Gene Attenuates Plasmin Generation and Invasiveness of Colo 222 Colorectal." J. Biol. Chem., 279(3), 2053-2062, 2004.

(Continued)

*Primary Examiner*—Christopher S. F. Low
*Assistant Examiner*—Jennifer Dunston
(74) *Attorney, Agent, or Firm*—McDonnell Boehnen Hulbert & Berghoff LLP

(57) ABSTRACT

The invention provides methods for predicting whether an ovarian cancer patient's tumor will be resistant to chemotherapy. The invention also provides methods for monitoring the effectiveness of treatment, particularly a chemotherapeutic treatment, in a patient treated for ovarian cancer. The invention further provides methods for treating ovarian cancer, by reducing chemotherapeutic drug resistance in said cells. In addition, the invention provides methods of screening compounds to identify tumor cell growth inhibitors in tumor cells resistant to conventional chemotherapeutic treatment regimes.

9 Claims, 60 Drawing Sheets

OTHER PUBLICATIONS

Khun WC, "Therapy for Recurrent Ovarian Cancer." Curr Women's Health Rep. Feb. 3(1):33-8, 2003.
Douillard JY et. al., "Challenging the Platinum Combinations in the Chemotherapy of NSCLC." Lung Cancer Dec. 38 Suppli 4:21-8, 2002.
Sandercock J et al., "First-lie Treatment for Advanced Ovarian Cancer: Paclitaxel, Platinum and the Evidence." Br. J Cancer Oct. 7; 87(8):815-24, 2002.
Whitley JC et al., "Temporal Expression and Cellular Localization of a Gastrin-Releasing Peptide-Related Gene in Ovine Uterus During the Oestrous Cycle and Pregnancy." J Endocrinol Apr; 157(1):139-48, 1998.
Smith CJ et al., "Development of Decompensated Dilated Cordiomyopathy is associated with Decreased Gene Expression and Activity of the Milrinone-Sensitive cAMP Phosphodiesterase PDE3A." Circulation Nov. 4; 96 (9):3116-23, 1997.
Jan M. Ruijter et al., "Statistical Evaluation of SAGE Libraries: Consequences for Experimental Design," Physiol Genomics 11: pp. 37-44 (2002).
Stephen L. Madden et al., "SAGE Transcript Profiles for p53-Dependent Growth Regulation," Oncogene 15, pp. 1079-1085 (1997).
Michael A. Hauser et al., "Genomic Convergence: Identifying Candidate Genes for Parkinson's Disease by Combining Serial Analysis of Gene Expression and Genetic Linkage," Human Molecular Genetics, vol. 12, No. 6 pp. 671-676 (2003).
Eric Raymond et al., "Cellular and Molecular Pharmacology of Oxaliplatin," Molecular Cancer Therapeutics, vol. 1, pp. 227-235 (2002).
Gerry P. Quinn and Michael J. Keough, "Experimental Design and Data Anlysis for Biologists," Cambridge University Press, pp. 48-50 (2002).
Victor E. Velculescu et al., "Serial Analysis of Gene Expression," Science, vol. 270 pp. 484-487 (1995).
Victor E. Velculescu et al., "Characterization of the Yeast Transcriptome," Cell, vol. 88 pp. 243-251 (1997).
Rintala-Dempsey et al., FEBS J. 275, 4956-4966 (2008).
Rintala-Dempsey et al., Biochemistry 45, 14695-14705 (2006).
Mai et. al., BBA 1477, 215-230 (2000).
Sharma and Sharma, Current Pharmaceutical Design 13, 3568-3575 (2007).
Kwon et. al., Frontiers in Bioscience 10, 300-325 (2005).
Choi et. al., FASEB 17, 235-246 (2003).
Zhang et. al., JBC 279, 2053-2062 (2004).
Wang et al., Gynecologic Oncology 114, 265-272 (2009).
Ljuca et al., Bosnian Journal of Basic Medical Sciences 7, 111-116 (2007).
Lu et al., 2003, "siRNA-mediated antitumorigenesis for drug target validation and therapeutics", Curr Opin Mol Therapeutics 5(3): 225-234.
Moler EJ et al., 2000, "Analysis of molecular profile data using generative and discriminative methods", Physiol Genomics 4:109-126.
Pejoic, 1995, "Genetic changes in ovarian cancer", Ann. Med. 27(1):73-8.
Bass, 2001, "The short answer", Nature 411: 428-429.
Elbashir et al., 2001, "Duplexes of 21-nucleotide RNAs mediate RNA interference in cultured mammalian cells", Nature 411(6836):494-8.
Fire et al, 1998, "Potent and specific genetic interference by double-stranded RNA in Caenorhabditis elegans", Nature 391:806.
Wianny and Goetz , "Specific interference with gene function by double-stranded RNA in early mouse development", 1999, Nature Cell Biol. 2:70.
Hammond et al., 2000, "An RNA-directed nuclease mediates post-transcriptional gene silencing in Drosophila cells", Nature 404(6775):293-6.
Elbashir et al., 2001, "Functional anatomy of siRNAs for mediating efficient RNAi in Drosophila melanogaster embryo lysate", EMBO J. 20(23):6877-88.
Paul et al., 2002, "Effective expression of small interfering RNA in human cells", Nature Biotechnology 20(5):505-8.
Miyagishi and Taira, 2002, "U6 promoter-driven siRNAs with four uridine 3' overhangs efficiently suppress targeted gene expression in mammalian cells", Nature Biotechnology 20(5):497-500.
Lee et al., 2002, "Expression of small interfering RNAs targeted against HIV-1 rev transcripts in human cells", Nature Biotechnology 20(5):500-5.
Novina et al., 2002, "siRNA-directed inhibition of HIV-1 infection", Nature Medicine, 8(7):681-6, online publication Jun. 3, 2003.
Akhtar et al., 1992, Trends Cell Bio. 2:139; Delivery Strategies for Antisense Oligonucleotide Therapeutics, ed. Akhtar, 1995.
Maurer et al., 1999, "Lipid-based systems for the intracellular delivery of genetic drugs", Mol. Membr. Biol. 16(1):129-40.
Hofland and Huang, 1999, "Formulation and delivery of nucleic acids", Handb. Exp. Pharmacol., 137:165-192.
Conry et al., 1999, "Phase I trial of a recombinant vaccinia virus encoding carcinoembryonic antigen in metastatic adenocarcinoma: comparison of intradermal versus subcutaneous administration", Clin. Cancer Res. 5(9):2330-7.
Chun et al., 1998, "Effect of infusion of vasoactive intestinal peptide (VIP)-antisense oligodeoxynucleotide into the third cerebral ventricle above the hypothalamic suprachiasmatic nucleus on the hyperglycemia caused by intracranial injection of 2-deoxy-D-glucose in rats", Neuroscience Letters 257(3):135-8.
D'Aldin et al., 1998, "Antisense oligonucleotides to the GluR2 AMPA receptor subunit modify excitatory synaptic transmission in vivo", Mol. Brain Research 55(1):151-64.
Dryden et al., 1998, "The lack of specificity of neuropeptide Y (NPY) antisense oligodeoxynucleotides administered intracerebroventricularly in inhibiting food intake and NPY gene expression in the rat hypothalamus", J. Endocrinol. 157(1):169-75.
Ghirnikar et al., 1998, "Chemokine inhibition in rat stab wound brain injury using antisense oligodeoxynucleotides", Neuroscience Letters 247(1):21-4.
Broaddus et al., 1997, "Distribution and stability of anisense phosphothioate oligonucleotide in rodent brain following direct intraparenchymal controlled-rate infusion", Neurosurg. Focus 3, article 4.
Gold, 1997, "Axonal regeneration of sensory nerves is delayed by continuous intrathecal infusion of nerve growth factor", Neuroscience 76:1153-1158.
lzant and Weintraub, 1985, "Constitutive and conditional suppression of exogenous and endogenous genes by anti-sense RNA", Science 229(4711):345-52.
McGarry and Lindquist, 1986, "Inhibition of heat shock protein synthesis by heat-inducible antisense RNA", Proc. Natl. Acad. Sci., USA 83(2):399-403.
Scanlon et al., 1991, "Ribozyme-mediated cleavage of c-fos mRNA reduces gene expression of DNA synthesis enzymes and metallothionein", Proc. Natl. Acad. Sci. USA 88(23):10591-5.
Kashani-Sabet et al., 1992, "Reversal of the malignant phenotype by an anti-ras ribozyme", Antisense Res. Dev. 2(1):3-15.
Dropulic et al., 1992, "Functional characterization of a U5 ribozyme: intracellular suppression of human immunodeficiency virus type 1 expression", J. Virol. 66(3):1432-41.
Weerasinghe et al., 1991, "Resistance to human immunodeficiency virus type 1 (HIV-1) infection in human CD4+ lymphocyte-derived cell lines conferred by using retroviral vectors expressing an HIV-1 RNA-specific ribozyme", J. Virol. 65(10):5531-4.
Ojwang et al., 1992,"Inhibition of human immunodeficiency virus type 1 expression by a hairpin ribozyme", Proc. Natl. Acad. Sci. USA 89(22):10802-6.
Chen et al., 1992, "Multitarget-ribozyme directed to cleave at up to nine highly conserved HIV-1 env RNA regions inhibits HIV-1 replication—potential effectiveness against most presently sequenced HIV-1 Isolates", Nucleic Acids Res. 20(17):4581-9.
Sarver et al., 1990, "Ribozymes as potential anti-HIV-1 therapeutic agents", Science 247(4947):1222-5.
Thompson et al., 1995, "Improved accumulation and activity of ribozymes expressed from a tRNA-based RNA polymerase III promoter", Nucleic Acids Res. 23(12):2259-68.
Good et al., 1997, "Expression of small, therapeutic RNAs in human cell nuclei", Gene Therapy 4: 45-54.

Kunkel and Pederson, 1989 "Transcription of a human U6 small nuclear RNA gene in vivo withstands deletion of intragenic sequences but not of an upstream TATATA box", Nucleic Acids Research 17:7371.

Ohkawa et al., 1992, "Activities of HIV-RNA targeted ribozymes transcribed from a 'shot-gun' type ribozyme-trimming plasmid", Nucleic Acids Symp. Ser. 27:15-6.

Taira et al., 1991, "Construction of a novel RNA-transcript-trimming plasmid which can be used both in vitro in place of run-off and (G)-free transcriptions and in vivo as multi-sequences transcription vectors", Nucleic Acids Res. 19(19):5125-30.

Ventura et al., 1993, "Activation of HIV-specific ribozyme activity by self-cleavage", Nucleic Acids Res. 21(14):3249-55.

Chowrira et al., 1994, "In vitro and in vivo comparison of hammerhead, hairpin, and hepatitis delta virus self-processing ribozyme cassettes", J. Biol. Chem. 269(41):25856-64.

Couture et al., 1996, "Anti-gene therapy: the use of ribozymes to Inhibit gene function", Trends in Genetics, 12(12):510-5.

Elroy-Stein and Moss, 1990, "Cytoplasmic expression system based on constitutive synthesis of bacteriophage 17 RNA polymerase in mammalian cells", Proc. Natl. Acad. Sci. USA 87(17):6743-7.

Gao and Huang 1993, "Cytoplasmic expression of a reporter gene by co-delivery of T7 RNA polymerase and T7 promoter sequence with cationic liposomes", Nucleic Acids Res. 21(12):2867-72.

Lieber et al., 1993, "Stable high-level gene expression in mammalian cells by T7 phage RNA polymerase", Methods Enzymol. 217:47-66.

Zhou et al., 1990, "Synthesis of functional mRNA in mammalian cells by bacteriophage T3 RNA polymerase", Mol. Cell. Biol. 10(9):4529-37.

Yu et al., 1993, "A hairpin ribozyme inhibits expression of diverse strains of human immunodeficiency virus type 1", Proc. Natl. Acad. Sci. USA 90: 6340-4.

L'Huillier et al, 1992, "Cytoplasmic delivery of ribozymes leads to efficient reduction in alpha-lactalbumin mRNA levels in C127I mouse cells", EMBO J. 11(12):4411-8.

Lisziewicz et al., 1993, "Inhibition of human Immunodeficiency virus type 1 replication by regulated expression of a polymeric Tat activation response RNA decoy as a strategy for gene therapy in AIDS", Proc. Natl. Acad. Sci. U.S.A 90(17):8000-4.

Sullenger and Cech, 1993, "Tethering ribozymes to a retroviral packaging signal for destruction of viral RNA". Science 262(5139):1566-9.

Noonberg et al., 1994, "In vivo generation of highly abundant sequence-specific oligonucleotides for antisense and triplex gene regulation", Nucleic Acid Res. 22(14):2830-6.

Kwon et al., 2000, "cis-fumagillin, a new methionine aminopeptidase (type 2) inhibitor produced by Penicillium sp. F2757", J. Antibiot. 53(8):799-806.

Zhou et al., 2003, "Fumagalone, a reversible inhibitor of type 2 methionine aminopeptidase and angiogenesis", J. Med. Chem. 46(16):3452-4.

Han et al., 2000, "Design and synthesis of highly potent fumagillin analogues from homology modeling for a human MetAP-2", Bioorganic & Medicinal Chem. Letters 10(1):39-43.

Wagner et al., 1981, "Nucleotide sequence of the thymidine kinase gene of herpes simplex virus type 1", Proc. Natl. Acad. Sci. U.S.A. 78:1444-45.

Brinster et al., 1982, "Regulation of metallothionein—thymidine kinase fusion plasmids injected into mouse eggs", Nature 296(5852):39-42.

Ridinger et al., 1998, "Clustered organization of S100 genes in human and mouse", Biochimica et Biophysica Acta 1448(2):254-63.

Lane and Sage, 1994, "The biology of SPARC, a protein that modulates cell-matrix interactions", FASEB J. 8(2):163-73.

Paley et al., 2000, "Alterations in SPARC and VEGF immunoreactivity in epithelial ovarian cancer", Gynecologic Oncology 78(3 Pt 1):336-41.

Yiu et al., 2001, "SPARC (secreted protein acidic and rich in cysteine) induces apoptosis in ovarian cancer cells", Am. J. Pathol. 159(2):609-22.

Ledda et al., 1997, "The expression of the secreted protein acidic and rich in cysteine (SPARC) is associated with the neoplastic progression of human melanoma", J. Invest. Dermatol. 108(2):210-4.

Porte et al., 1995, "Neoplastic progression of human colorectal cancer is associated with overexpression of the stromelysin-3 and BM-40/SPARC genes", Int. J. Cancer 64(1):70-5.

Thomas et al., 2000, "Differential expression of osteonectin/SPAEC during human prostate cancer progression", Clin. Cancer Res. 6(3):1140-9.

Golembieski et al., 1999, "Increased SPARC expression promotes U87 glioblastoma invasion in vitro", Int. J. Dev. Neurosci. 17(5-6):463-72.

Briggs et al., 2002, "Transcriptional upregulation of SPARC, in response to c-Jun overexpression, contributes to increased motility and invasion of MCF7 breast cancer cells", Oncogene 21(46):7077-91.

Huang and Wang, 2001, "The calpain family and human disease", Trends in Molecular Medicine 7(8):355-62.

Lollike et al., 2001, "Biochemical characterization of the penta-EF-hand protein grancalcin and identification of L-plastin as a binding partner", J. Biol. Chem. 276(21):17762-9.

Li and Chang, 1996, "Evidence that the human homologue of a rat initiation factor-2 associated protein (p67) is a methionine aminopeptidase", Biochem. Biophys. Res. Commun. 227(1):152-9.

Wu et al., 1993,"Cloning and characterization of complementary DNA encoding the eukaryotic initiation factor 2-associated 67-kDa protein (p67)", J. Biol. Chem. 268(15):10796-801.

Kruger and Figg, 2000, "TNP-470: an angiogenesis inhibitor in clinical development for cancer", Expert Opin. Investig. Drugs 9(6):1383-96.

Datta and Datta, 1999, "Induction of apoptosis due to lowering the level of eukaryotic initiation factor 2- associated protein, p67, from mammalian cells by antisense approach", Exp. Cell Res. 246(2):376-83.

Paulin et al., 2001, "Eukaryotic translation initiation factor 5 (eIF5) acts as a classical GTPase-activator protein", Current Biol. 11(1):55-9.

Das et al., 2001, "Eukaryotic translation initiation factor 5 functions as a GTPase-activating protein", J. Bio. Chem. 276:6720-6.

Proud, 2001, "Regulation of eukaryotic initiation factor eIF2 I3", Prog. Mol. Subcell. Biol. 26:95-114.

Browne and Proud, 2002, "Regulation of peptide-chain elongation in mammalian cells", Eur. J. Biochem. 269(22):5360-8.

Cuenda, 2000, "Mitogen-activated protein kinase kinase 4 (MKK4)", Int. J. Biochem. Cell Biol. 32(6):581-7.

Toshima, 2001, "Cofilin phosphorylation and actin reorganization activities of testicular protein kinase 2 and its predominant expression in testicular Sertoli cells", J. Biol. Chem. 276(33):31449-58.

Tian et al., 1995, "Fas-activated serine/threonine kinase (FAST) phosphorylates TIA-1 during Fasmediated apoptosis", J. Exp. Med. 182(3):865-74.

Diamandis, 2000, "Human kallikrein 6 (zyme/protease M/neurosin): a new serum biomarker of ovarian carcinoma", Clinical Biochem. 33(7):579-83.

Scorlias et al., 2000, "Genomic organization, physical mapping, and expression analysis of the human protein arginine methyltransferase 1 gene", Biochem. Biophys. Res. Commun. 278(2):349-59.

Kazlauskas et al., 2002, "Two distinct regions of the immunophilin-like protein XAP2 regulate dioxin receptor function and interaction with hsp90", J. Biol. Chem. 277(14):11795-801.

Mosunjac et al., 2000, "Use of a novel marker, calponin, for myoepithelial cells in fine-needle aspirates of papillary breast lesions", Diagn. Cytophathol. 23(3):151-5.

Tamm et al., 2000, "Expression and prognostic significance of IAP-Family genes in human cancers and myeloid leukemias", Clin. Cancer Res. 6:1796-1803.

Schwerk et al., 2003, "ASAP, a novel protein complex involved in RNA processing and apoptosis", Mol. Cell Biol. 23(8):2981-90.

Harada et al., 2001, "Binding of a SART3 tumor-rejection antigen to a pre-mRNA splicing factor RNPS1: a possible regulation of splicing by a complex formation", Int. J. Cancer 93(5):623-8.

Mathew et al., 1998, "Heat shock response and protein degradation: regulation of HSF2 by the ubiquitinproteasome pathway", Mol. Cell Biol. 18(9):5091-8.

Hong et al., 2000, "Molecular basis of competition between HSF2 and catalytic subunit for binding to the PR65/A subunit of PP2A", Biochem. Biophys. Res. Commun. 272(1):84-9.

Li et al., 2000, "Molecular basis of competition between HSF2 and catalytic subunit for binding to the PR65/A subunit of PP2A", Biochem. Biophys. Res. Commun. 274:117-23.

Lesche et al., 1997, "Ft1, a novel gene related to ubiquitin-conjugating enzymes, is deleted in the Fused toes mouse mutation", Mamm. Genome 8(12):879-83.

Hayer et al., 2001, "Overexpression of nm23-H4 RNA in colorectal and renal tumours", Anticancer Res. 21(4A):2821-5.

Wang et al., 2000, "Requirement of the RNA editing deaminase ADAR1 gene for embryonic erythropoiesis", Science 290(5497):1765-8.

Whitehouse et al., 2002, "NBR1 interacts with fasciculation and elongation protein zeta-1 (FEZ1) and calcium and integrin binding protein (CIB) and shows developmentally restricted expression in the neural tube", Eur. J. Biochem. 269(2):538-45.

Smedley et al., 1999, "Cloning and mapping of members of the MYM family", Genomics 60(2):244-7.

Protopopov et al., 2003, "An integrated physical and gene map of the 3.5-Mb chromosome 3p21.3 (AP20) region implicated in major human epithelial malignancies", Cancer Res. 63(2):404-12.

Senchenko et al., 2003, "Deletion mapping using quantitative real-time PCR identifies two distinct 3p21.3 regions affected in most cervical carcinomas" Oncogene 22(19):2984-92.

Kioka et al., 2002, "Vinexin, CAP/ponsin, ArgBP2: a novel adaptor protein family regulating cytoskeletal organization and signal transduction", Cell Structure and Function 27(1):1-7.

Savarese et al., 2001, "Coexpression of granulocyte colony stimulating factor and its receptor in primary ovarian carcinomas", Cancer Letters 162(1):105-15.

Fukasawa et al., 1996, "SRB1, a class B scavenger receptor, recognizes both negatively charged liposomes and apoptotic cells", Exp. Cell Res. 222(11):246-50.

Oh, 1998, "IGF-independent regulation of breast cancer growth by IGF binding proteins", Breast Cancer Res. Treat. 47:283-93.

Kauppi et al., 2002, "The small GTPase Rab22 interacts with EEA1 and controls endosomal membrane trafficking", J. Cell Science 115(Pt 5):899-911.

Jepsen and Rosenfeld, 2002, "Biological roles and mechanistic actions of co-repressor complexes", J. Cell Science 115(Pt 4):689-98.

Andrews and Howell, 1990, "Cellular pharmacology of cisplatin: perspectives on mechanisms of acquired resistance", Cancer Cells 2(2):35-43.

Nakano et al., 2003, "Expression pattern of cisplatin-induced metallothionein isoforms in squamous cell carcinoma", Anticancer Res. 23:299-304.

Baserga et al., 1997, "Mpp10p, a new protein component of the U3 snoRNP required for processing of 18S rRNA precursors", Nucleic Acids Symp. Ser. 36:64-7.

Griffith et al., 1998, "Molecular recognition of angiogenesis inhibitors fumagillin and ovalicin by methionine aminopeptidase 2", Proc. Natl. Acad. Sci. USA 95(26):15183-8.

Wang et al., 2000, "Selective inhibition of endothelial cell proliferation by fumagillin is not due to differential expression of methionine aminopeptidases", J. Cell. Biochem. 77(3):465-73.

Tanaka et al., 1995, "Prevention of hepatic metastasis of human colon cancer by angiogenesis inhibitor TNP-470", Cancer Res. 55(4):836-9.

GenBank Accession No. D88153, Homo sapiens mRNA for HYA22, complete cds, Aug. 1, 1997.

GenBank Accession No. AB049635, Homo sapiens MRPL4 mRNA for mitochondrial ribosomal protein L4, Jun. 14, 2001.

GenBank Accession No. AF037261, Homo sapiens SH3-containing adaptor molecule-1 mRNA, complete cds, Apr. 2, 1998.

GenBank Accession No. M59818, Human granulocyte colony-stimulating factor receptor (G-CSFR-1), Mar. 6, 1995.

GenBank Accession No. BC015710, Homo sapiens RAB22A, member RAS oncogene family, mRNA (cDNA clone MGC:16770 Image:3907891), complete cds, Jul. 15, 2006.

GenBank Accession No. BC017201, Homo sapiens insulin-like growth factor binding protein 7, mRNA (cDNA clone MGC:3699 Image:3632247), complete cds, Jul. 15, 2006.

GenBank Accession No. BC011770, Homo sapiens Fas-activated serine/threonine kinase, mRNA (cDNA clone MGC:19784 Image:3831196), complete cds, Jul. 15, 2006.

GenBank Accession No. AB057597, Homo sapiens mRNA for testicular protein kinase 2, complete cds, Aug. 16, 2001.

GenBank Accession No. BC022087, Homo sapiens scavenger receptor class B, member 1, mRNA, Apr. 1, 2004.

GenBank Accession No. BC031890, Homo sapiens KIAA0082, mRNA (cDNA clone MGC:29890 Image:4944457), complete cds, Jul. 15, 2006.

GenBank Accession No. NM_006312, Homo sapiens nuclear receptor co-repressor 2 (NCOR2), transcript variant 1, mRNA, Oct. 18, 2006.

GenBank Accession No. BC032338, Homo sapiens nuclear receptor co-repressor 2 (NCOR2), transcript variant 1, mRNA, Oct. 18, 2006.

GenBank Accession No. X98494, H.sapiens mRNA for M phase phosphoprotein 10, Apr. 18, 2005.

GenBank Accession No. BC015973, Homo sapiens S100 calcium binding protein A10, mRNA (cDNA clone MGC:23737 Image:4103596), complete cds, Sep. 28, 2006.

GenBank Accession No. BC001410, Homo sapiens S100 calcium binding protein A11, mRNA (cDNA clone MGC:2149 Image:3140092), complete cds, Sep. 14, 2006.

GenBank Accession No. AF261089, Homo sapiens calpain large polypeptide L2 mRNA, complete cds, Sep. 8, 2000.

GenBank Accession No. BC004974, Homo sapiens secreted protein, acidic, cysteine-rich (osteonectin), mRNA (cDNA clone MGC:3651 Image:2906092), complete cds, Jul. 15, 2006.

GenBank Accession No. BC013782, Homo sapiens methionyl aminopeptidase 2, mRNA (cDNA clone MGC:17192 Image:4340717), complete cds, Sep. 1, 2006.

GenBank Accession No. BC015525, Homo sapiens kallikrein 6 (neurosin, zyme), mRNA (cDNA clone MGC:9355 Image:3852344), complete cds, Jul. 15, 2006.

GenBank Accession No. AF222689, Homo sapiens protein arginine N-methyltransferase 1 (HRMT1L2) gene, complete cds, alternatively spliced, Apr. 10, 2001.

GenBank Accession No. U31913, Human HBV-X associated (XAP2) mRNA, complete cds, Jan. 7, 1997.

GenBank Accession No. D83735, Homo sapiens mRNA for neutral calponin, complete cds, Feb. 6, 1999.

GenBank Accession No. U19251, Homo sapiens neuronal apoptosis inhibitory protein mRNA, complete cds, Mar. 13, 1998.

GenBank Accession No. BC005291, Homo sapiens eukaryotic translation elongation factor 1 epsilon 1, mRNA (cDNA clone MGC:12352 Image:3685030), complete cds, Jul. 15, 2006.

GenBank Accession No. AF015608, Homo sapiens SR protein (RNPS1) mRNA, complete cds, Jun. 25, 1998.

GenBank Accession No. U49436, Human translation initiation factor 5 (eIF5) mRNA, complete cds, Jul. 12, 1996.

GenBank Accession No. BC013590, Homo sapiens eukaryotic translation initiation factor 2B, subunit 5, Jul. 15, 2006.

GenBank Accession No. M65217, Human heat shock factor 2 (HSF2) mRNA, complete cds, Apr. 27, 1993.

GenBank Accession No. AB010427, Homo sapiens mRNA for NOR1-1, complete cds, Jun. 18, 1999.

GenBank Accession No. BC001134, Homo sapiens fused toes homolog (mouse), mRNA (cDNA clone MGC:2845 Image:2967019), complete cds, Jul. 15, 2006.

GenBank Accession No. BC004880, Homo sapiens non-metastatic cells 4, protein expressed in, mRNA (cDNA clone MGC:11088 Image:3830205), complete cds, Jul. 15, 2006.

GenBank Accession No. U10439, Human double-stranded RNA adenosine deaminase mRNA, complete cds, Aug. 27, 1996.

GenBank Accession No. BC005214, Homo sapiens grancalcin, EF-hand calcium binding protein, mRNA (cDNA clone MGC:12231 Image:3996889), complete cds, Jul. 15, 2006.

GenBank Accession No. BC009808, Homo sapiens neighbor of BRCA1 gene 1, mRNA (cDNA clone MGC:1377 Image:2989212), complete cds, Feb. 22, 2005.

GenBank Accession No. L36870, Homo sapiens MAP kinase klnase 4 (MKK4) mRNA, complete cds, Feb. 28, 1995.

GenBank Accession No. AB007885, Homo sapiens KIAA0425 mRNA, partial cds, Jan. 10, 2004.

* cited by examiner

Validation of the expression of 250654 in epithelial ovarian cancer cell lines by quantitative real-time PCR

Probe Sequence

FAM-CGCGTATGAACTGGGCTTATGTGACGCG-DABCYL  (SEQ ID NO: 13)

Northern Blot Analysis of 306921

\* Points shown are averages of duplicates

Resistance to *cis*- platin

Northern Blot Analysis of 246120

*Points shown are averages of duplicates

Resistance to *cis*- platin

Northern Blot Analysis of 713886

* Points shown are averages of duplicates

Resistance to *cis-* platin

Northern Blot Analysis of 714196

*Points shown are averages of duplicates

Resistance to *cis*- platin

Northern Blot Analysis of 743230

*Points shown averages of duplicates

Resistance to *cis-* platin

OVCA 429 cell survival after 4 hours of exposure to Fumagillin
(All data points shown are averages of two independent experiments)

OVCA 429 cell survival after 4 hours of exposure to either cis-platin alone or combinations of *cis*-platin and Fumagillin
(All data points shown are averages of two independent experiments)

OVCA 429 cell survival after 8 hours of exposure to Fumagillin
(All data points shown are averages of two independent experiments)

OVCA 429 cell survival after 8 hours of exposure to either *cis*-platin alone or combinations of *cis*-platin and Fumagillin
(All data points shown are averages of two independent experiments)

OVCA 429 cell survival after 24 hours of exposure to Fumagillin
(All data points shown are averages of two independent experiments)

OVCA 429 cell survival after 24 hours of exposure to either *cis*-platin alone or combinations of *cis*-platin and Fumagillin
(All data points shown are averages of two independent experiments)

Silencing the 39093 mRNA

Target sequence #1    Target sequence #2    Target sequence #3

1 mRNA Target Sequence: AAA GAT CAG CAT TGG AAG ATA   (SEQ ID NO: 4)

2 mRNA Target Sequence: AAG CAC ATC GAC AAG TTA GAA   (SEQ ID NO: 5)

3 mRNA Target Sequence: AAA CAG TGC CGA TTG TGA AAG   (SEQ ID NO: 6)

Quantitative real-time PCR analysis of 39093 mRNA expression in
OVCA 429 cells transfected with sense strand #1 alone or with siRNA #1

Quantitative real-time PCR analysis of GAPDH mRNA expression in
OVCA 429 cells treated with siPort lipid alone or transfected with
39093 siRNA #1

Silencing the 250654 mRNA

1 mRNA Target Sequence: AAT CCT GTC CAG GTG GAA GTA (SEQ ID NO: 1)

2 mRNA Target Sequence: AAG CTC CAC CTG GAC TAC ATC (SEQ ID NO: 2)

3 mRNA Target Sequence: AAT GAC AAG TAC ATC GCC CTG (SEQ ID NO: 3)

SEQUENCE LISTING

<160> NUMBER OF SEQ ID NOS: 144

<210> SEQ ID NO 1
<211> LENGTH: 21
<212> TYPE: DNA
<213> ORGANISM: Homo Sapiens

<400> SEQUENCE: 1
aatcctgtcc aggtggaagt a                                              21

<210> SEQ ID NO 2
<211> LENGTH: 21
<212> TYPE: DNA
<213> ORGANISM: Homo Sapiens

<400> SEQUENCE: 2
aagctccacc tggactacat c                                              21

```
<210> SEQ ID NO 3
<211> LENGTH: 21
<212> TYPE: DNA
<213> ORGANISM: Homo Sapiens

<400> SEQUENCE: 3
aatgacaagt acatcgccct g                                          21

<210> SEQ ID NO 4
<211> LENGTH: 21
<212> TYPE: DNA
<213> ORGANISM: Homo Sapiens

<400> SEQUENCE: 4
aaagatcagc attggaagat a                                          21

<210> SEQ ID NO 5
<211> LENGTH: 21
<212> TYPE: DNA
<213> ORGANISM: Homo Sapiens

<400> SEQUENCE: 5
aagcacatcg acaagttaga a                                          21

<210> SEQ ID NO 6
<211> LENGTH: 21
<212> TYPE: DNA
<213> ORGANISM: Homo Sapiens

<400> SEQUENCE: 6
aaacagtgcc gattgtgaaa g                                          21

<210> SEQ ID NO 7
<211> LENGTH: 21
<212> TYPE: DNA
<213> ORGANISM: Homo Sapiens

<400> SEQUENCE: 7
aaggcatacg ccaagatcaa c                                          21

<210> SEQ ID NO 8
<211> LENGTH: 21
<212> TYPE: DNA
<213> ORGANISM: Homo Sapiens

<400> SEQUENCE: 8
aaacttcttc ctgacgaatc g                                          21

<210> SEQ ID NO 9
<211> LENGTH: 21
<212> TYPE: DNA
<213> ORGANISM: Homo Sapiens

<400> SEQUENCE: 9
aaacgctatt caagatattt a                                          21

<210> SEQ ID NO 10
<211> LENGTH: 21
<212> TYPE: DNA
<213> ORGANISM: Homo Sapiens

<400> SEQUENCE: 10
aaaggatggt tataactaca c                                          21
```

<210> SEQ ID NO 11
<211> LENGTH: 21
<212> TYPE: DNA
<213> ORGANISM: Homo Sapiens

<400> SEQUENCE: 11
aagaaactgg acaccaacag t                                              21

<210> SEQ ID NO 12
<211> LENGTH: 21
<212> TYPE: DNA
<213> ORGANISM: Homo Sapiens

<400> SEQUENCE: 12
aatctgattg gtggcctagc t                                              21

<210> SEQ ID NO 13
<211> LENGTH: 28
<212> TYPE: DNA
<213> ORGANISM: Artificial
<220> FEATURE:
<223> OTHER INFORMATION: Molecular Beacon Probe
<220> FEATURE:
<221> NAME/KEY: Unsure
<222> LOCATION: (1)..(1)
<223> OTHER INFORMATION: c linked to FAM
<220> FEATURE:
<221> NAME/KEY: Unsure
<222> LOCATION: (28)..(28)
<223> OTHER INFORMATION: g linked to DABCYL

<400> SEQUENCE: 13
cgcgtatgaa ctgggcttat gtgacgcg                                       28

<210> SEQ ID NO 14
<211> LENGTH: 20
<212> TYPE: DNA
<213> ORGANISM: Artificial
<220> FEATURE:
<223> OTHER INFORMATION: PCR Primer

<400> SEQUENCE: 14
ctgggctctg ccttaaacac                                                20

<210> SEQ ID NO 15
<211> LENGTH: 20
<212> TYPE: DNA
<213> ORGANISM: Artificial
<220> FEATURE:
<223> OTHER INFORMATION: PCR Primer

<400> SEQUENCE: 15
gctcccaaaa gtttgaacca                                                20

<210> SEQ ID NO 16
<211> LENGTH: 20
<212> TYPE: DNA
<213> ORGANISM: Artificial
<220> FEATURE:
<223> OTHER INFORMATION: PCR Primer

<400> SEQUENCE: 16
ttgcctgagg ctgtaactga                                                20

```
<210> SEQ ID NO 17
<211> LENGTH: 20
<212> TYPE: DNA
<213> ORGANISM: Artificial
<220> FEATURE:
<223> OTHER INFORMATION: PCR Primer

<400> SEQUENCE: 17
ccacttcttt gccacaaagt                                          20

<210> SEQ ID NO 18
<211> LENGTH: 20
<212> TYPE: DNA
<213> ORGANISM: Artificial
<220> FEATURE:
<223> OTHER INFORMATION: PCR Primer

<400> SEQUENCE: 18
gaattcggtc agctcagagt                                          20

<210> SEQ ID NO 19
<211> LENGTH: 25
<212> TYPE: DNA
<213> ORGANISM: Artificial
<220> FEATURE:
<223> OTHER INFORMATION: Molecular Beacon Probe
<220> FEATURE:
<221> NAME/KEY: Unsure
<222> LOCATION: (1)..(1)
<223> OTHER INFORMATION: c linked to FAM
<220> FEATURE:
<221> NAME/KEY: Unsure
<222> LOCATION: (25)..(25)
<223> OTHER INFORMATION: g linked to DABCYL

<400> SEQUENCE: 19
cgcctgggtg ggtttgaagg aggcg                                    25

<210> SEQ ID NO 20
<211> LENGTH: 20
<212> TYPE: DNA
<213> ORGANISM: Artificial
<220> FEATURE:
<223> OTHER INFORMATION: PCR Primer

<400> SEQUENCE: 20
atcgagtccc tgattgctgt                                          20

<210> SEQ ID NO 21
<211> LENGTH: 20
<212> TYPE: DNA
<213> ORGANISM: Artificial
<220> FEATURE:
<223> OTHER INFORMATION: PCR Primer

<400> SEQUENCE: 21
gcctgcatga ggtggttagt                                          20

<210> SEQ ID NO 22
<211> LENGTH: 20
<212> TYPE: DNA
<213> ORGANISM: Artificial
<220> FEATURE:
<223> OTHER INFORMATION: PCR Primer

<400> SEQUENCE: 22
cttgccatga ctccttcctc                                          20
```

```
<210> SEQ ID NO 23
<211> LENGTH: 20
<212> TYPE: DNA
<213> ORGANISM: Artificial
<220> FEATURE:
<223> OTHER INFORMATION: PCR Primer

<400> SEQUENCE: 23
gcagaagcac atcgacaagt                                               20

<210> SEQ ID NO 24
<211> LENGTH: 21
<212> TYPE: DNA
<213> ORGANISM: Artificial
<220> FEATURE:
<223> OTHER INFORMATION: PCR Primer

<400> SEQUENCE: 24
gcctgcattt aatccattct c                                             21

<210> SEQ ID NO 25
<211> LENGTH: 20
<212> TYPE: DNA
<213> ORGANISM: Artificial
<220> FEATURE:
<223> OTHER INFORMATION: PCR Primer

<400> SEQUENCE: 25
taaccacgtc ctgctgaagt                                               20

<210> SEQ ID NO 26
<211> LENGTH: 23
<212> TYPE: DNA
<213> ORGANISM: Artificial
<220> FEATURE:
<223> OTHER INFORMATION: PCR Primer

<400> SEQUENCE: 26
gctttaagaa agttcttatc aac                                           23

<210> SEQ ID NO 27
<211> LENGTH: 19
<212> TYPE: DNA
<213> ORGANISM: Artificial
<220> FEATURE:
<223> OTHER INFORMATION: PCR Primer

<400> SEQUENCE: 27
gcacagcgga gtggtaaga                                                19

<210> SEQ ID NO 28
<211> LENGTH: 20
<212> TYPE: DNA
<213> ORGANISM: Artificial
<220> FEATURE:
<223> OTHER INFORMATION: PCR Primer

<400> SEQUENCE: 28
cagaggagtc agacacattg                                               20

<210> SEQ ID NO 29
<211> LENGTH: 22
<212> TYPE: DNA
<213> ORGANISM: Artificial
<220> FEATURE:
<223> OTHER INFORMATION: PCR Primer
```

```
<400> SEQUENCE: 29
gtatacttac ttcagtgctg tt                                              22

<210> SEQ ID NO 30
<211> LENGTH: 23
<212> TYPE: DNA
<213> ORGANISM: Artificial
<220> FEATURE:
<223> OTHER INFORMATION: PCR Primer

<400> SEQUENCE: 30
cattcttgct ataacgttta aca                                             23

<210> SEQ ID NO 31
<211> LENGTH: 19
<212> TYPE: DNA
<213> ORGANISM: Artificial
<220> FEATURE:
<223> OTHER INFORMATION: PCR Primer

<400> SEQUENCE: 31
ctctgtgact tcggcatca                                                  19

<210> SEQ ID NO 32
<211> LENGTH: 19
<212> TYPE: DNA
<213> ORGANISM: Artificial
<220> FEATURE:
<223> OTHER INFORMATION: PCR Primer

<400> SEQUENCE: 32
cagacatcag agcggacat                                                  19

<210> SEQ ID NO 33
<211> LENGTH: 21
<212> TYPE: DNA
<213> ORGANISM: Artificial
<220> FEATURE:
<223> OTHER INFORMATION: PCR Primer

<400> SEQUENCE: 33
aagaactggg ttcagtggaa a                                               21

<210> SEQ ID NO 34
<211> LENGTH: 20
<212> TYPE: DNA
<213> ORGANISM: Artificial
<220> FEATURE:
<223> OTHER INFORMATION: PCR Primer

<400> SEQUENCE: 34
gagagtgcat ggtcttgagt                                                 20

<210> SEQ ID NO 35
<211> LENGTH: 20
<212> TYPE: DNA
<213> ORGANISM: Artificial
<220> FEATURE:
<223> OTHER INFORMATION: PCR Primer

<400> SEQUENCE: 35
agccaccagc taagtacctt                                                 20
```

```
<210> SEQ ID NO 36
<211> LENGTH: 21
<212> TYPE: DNA
<213> ORGANISM: Artificial
<220> FEATURE:
<223> OTHER INFORMATION: PCR Primer

<400> SEQUENCE: 36
catcgatttc aaccggaaca a                                              21

<210> SEQ ID NO 37
<211> LENGTH: 20
<212> TYPE: DNA
<213> ORGANISM: Artificial
<220> FEATURE:
<223> OTHER INFORMATION: PCR Primer

<400> SEQUENCE: 37
gtgtgtggac ctccatgtta                                                20

<210> SEQ ID NO 38
<211> LENGTH: 21
<212> TYPE: DNA
<213> ORGANISM: Artificial
<220> FEATURE:
<223> OTHER INFORMATION: PCR Primer

<400> SEQUENCE: 38
agcacaccat tacagacaag t                                              21

<210> SEQ ID NO 39
<211> LENGTH: 20
<212> TYPE: DNA
<213> ORGANISM: Artificial
<220> FEATURE:
<223> OTHER INFORMATION: PCR Primer

<400> SEQUENCE: 39
ggaaccagtt tctgcaggaa                                                20

<210> SEQ ID NO 40
<211> LENGTH: 19
<212> TYPE: DNA
<213> ORGANISM: Artificial
<220> FEATURE:
<223> OTHER INFORMATION: PCR Primer

<400> SEQUENCE: 40
ctccagcagc acctcaatg                                                 19

<210> SEQ ID NO 41
<211> LENGTH: 22
<212> TYPE: DNA
<213> ORGANISM: Artificial
<220> FEATURE:
<223> OTHER INFORMATION: PCR Primer

<400> SEQUENCE: 41
atccaaggtt atgtggtttc tt                                             22

<210> SEQ ID NO 42
<211> LENGTH: 19
<212> TYPE: DNA
<213> ORGANISM: Artificial
<220> FEATURE:
<223> OTHER INFORMATION: PCR Primer
```

<400> SEQUENCE: 42
cacctcctgg gcttctgaa                                                        19

<210> SEQ ID NO 43
<211> LENGTH: 22
<212> TYPE: DNA
<213> ORGANISM: Artificial
<220> FEATURE:
<223> OTHER INFORMATION: PCR Primer

<400> SEQUENCE: 43
gatccatgaa gctaatgtac aa                                                    22

<210> SEQ ID NO 44
<211> LENGTH: 19
<212> TYPE: DNA
<213> ORGANISM: Artificial
<220> FEATURE:
<223> OTHER INFORMATION: PCR Primer

<400> SEQUENCE: 44
acgggcagaa gccttcgtt                                                        19

<210> SEQ ID NO 45
<211> LENGTH: 19
<212> TYPE: DNA
<213> ORGANISM: Artificial
<220> FEATURE:
<223> OTHER INFORMATION: PCR Primer

<400> SEQUENCE: 45
cctgaggttc tccgagatg                                                        19

<210> SEQ ID NO 46
<211> LENGTH: 20
<212> TYPE: DNA
<213> ORGANISM: Artificial
<220> FEATURE:
<223> OTHER INFORMATION: PCR Primer

<400> SEQUENCE: 46
tccagcccga aattctctgt                                                       20

<210> SEQ ID NO 47
<211> LENGTH: 19
<212> TYPE: DNA
<213> ORGANISM: Artificial
<220> FEATURE:
<223> OTHER INFORMATION: PCR Primer

<400> SEQUENCE: 47
caagaggcgg aagggtaaa                                                        19

<210> SEQ ID NO 48
<211> LENGTH: 17
<212> TYPE: DNA
<213> ORGANISM: Artificial
<220> FEATURE:
<223> OTHER INFORMATION: PCR Primer

<400> SEQUENCE: 48
cagccgctcg ggtaggt                                                          17

<210> SEQ ID NO 49
<211> LENGTH: 20
<212> TYPE: DNA
<213> ORGANISM: Artificial
<220> FEATURE:
<223> OTHER INFORMATION: PCR Primer

<400> SEQUENCE: 49
cactatggaa ggaccttgct                                              20

<210> SEQ ID NO 50
<211> LENGTH: 21
<212> TYPE: DNA
<213> ORGANISM: Artificial
<220> FEATURE:
<223> OTHER INFORMATION: PCR Primer

<400> SEQUENCE: 50
ggatacaggt gtaggtaaat c                                            21

<210> SEQ ID NO 51
<211> LENGTH: 22
<212> TYPE: DNA
<213> ORGANISM: Artificial
<220> FEATURE:
<223> OTHER INFORMATION: PCR Primer

<400> SEQUENCE: 51
tcccagatta ggaatttatg ta                                           22

<210> SEQ ID NO 52
<211> LENGTH: 19
<212> TYPE: DNA
<213> ORGANISM: Artificial
<220> FEATURE:
<223> OTHER INFORMATION: PCR Primer

<400> SEQUENCE: 52
cttctggaac aggcgaaga                                               19

<210> SEQ ID NO 53
<211> LENGTH: 18
<212> TYPE: DNA
<213> ORGANISM: Artificial
<220> FEATURE:
<223> OTHER INFORMATION: PCR Primer

<400> SEQUENCE: 53
gctggcccag acgacgaa                                                18

<210> SEQ ID NO 54
<211> LENGTH: 19
<212> TYPE: DNA
<213> ORGANISM: Artificial
<220> FEATURE:
<223> OTHER INFORMATION: PCR Primer

<400> SEQUENCE: 54
gcagacacac gtggatggt                                               19

<210> SEQ ID NO 55
<211> LENGTH: 22
<212> TYPE: DNA
<213> ORGANISM: Artificial
<220> FEATURE:
<223> OTHER INFORMATION: PCR Primer

```
<400> SEQUENCE: 55
gatgaagtta aatcctcctt tg                                          22

<210> SEQ ID NO 56
<211> LENGTH: 20
<212> TYPE: DNA
<213> ORGANISM: Artificial
<220> FEATURE:
<223> OTHER INFORMATION: PCR Primer

<400> SEQUENCE: 56
cctcttctgt gctgtcactt                                             20

<210> SEQ ID NO 57
<211> LENGTH: 19
<212> TYPE: DNA
<213> ORGANISM: Artificial
<220> FEATURE:
<223> OTHER INFORMATION: PCR Primer

<400> SEQUENCE: 57
cctgcaagaa gagctgctg                                              19

<210> SEQ ID NO 58
<211> LENGTH: 19
<212> TYPE: DNA
<213> ORGANISM: Artificial
<220> FEATURE:
<223> OTHER INFORMATION: PCR Primer

<400> SEQUENCE: 58
cacagctgtc ctggcatca                                              19

<210> SEQ ID NO 59
<211> LENGTH: 21
<212> TYPE: DNA
<213> ORGANISM: Homo Sapiens

<400> SEQUENCE: 59
aaatggaaca cgccatggaa a                                           21

<210> SEQ ID NO 60
<211> LENGTH: 21
<212> TYPE: DNA
<213> ORGANISM: Homo Sapiens

<400> SEQUENCE: 60
aaattcgctg gggataaagg c                                           21

<210> SEQ ID NO 61
<211> LENGTH: 21
<212> TYPE: DNA
<213> ORGANISM: Homo Sapiens

<400> SEQUENCE: 61
aataatgaag gacctggacc a                                           21

<210> SEQ ID NO 62
<211> LENGTH: 20
<212> TYPE: DNA
<213> ORGANISM: Artificial
<220> FEATURE:
<223> OTHER INFORMATION: PCR Primer
```

```
<400> SEQUENCE: 62
gctcccaaaa gtttgaacca                                              20

<210> SEQ ID NO 63
<211> LENGTH: 20
<212> TYPE: DNA
<213> ORGANISM: Artificial
<220> FEATURE:
<223> OTHER INFORMATION: PCR Primer

<400> SEQUENCE: 63
gcctgcatga ggtggttagt                                              20

<210> SEQ ID NO 64
<211> LENGTH: 21
<212> TYPE: DNA
<213> ORGANISM: Homo Sapiens

<400> SEQUENCE: 64
aaatgggacg aggagcttat g                                            21

<210> SEQ ID NO 65
<211> LENGTH: 21
<212> TYPE: DNA
<213> ORGANISM: Homo Sapiens

<400> SEQUENCE: 65
aagcgcatca cgacaaggat a                                            21

<210> SEQ ID NO 66
<211> LENGTH: 21
<212> TYPE: DNA
<213> ORGANISM: Homo Sapiens

<400> SEQUENCE: 66
aacaggattg actactatag c                                            21

<210> SEQ ID NO 67
<211> LENGTH: 21
<212> TYPE: DNA
<213> ORGANISM: Homo Sapiens

<400> SEQUENCE: 67
aatacagggt cactcaagta g                                            21

<210> SEQ ID NO 68
<211> LENGTH: 21
<212> TYPE: DNA
<213> ORGANISM: Homo Sapiens

<400> SEQUENCE: 68
aaatatctta atgtgtctcg c                                            21

<210> SEQ ID NO 69
<211> LENGTH: 21
<212> TYPE: DNA
<213> ORGANISM: Homo Sapiens

<400> SEQUENCE: 69
aagtgtgagc tgcgccacaa g                                            21
```

```
<210> SEQ ID NO 70
<211> LENGTH: 21
<212> TYPE: DNA
<213> ORGANISM: Homo Sapiens

<400> SEQUENCE: 70
aagagccccc ttacccacta c                                              21

<210> SEQ ID NO 71
<211> LENGTH: 21
<212> TYPE: DNA
<213> ORGANISM: Homo Sapiens

<400> SEQUENCE: 71
aacaggaaga atccccctctg g                                             21

<210> SEQ ID NO 72
<211> LENGTH: 21
<212> TYPE: DNA
<213> ORGANISM: Homo Sapiens

<400> SEQUENCE: 72
aaacgtgtga tacaggaagg c                                              21

<210> SEQ ID NO 73
<211> LENGTH: 21
<212> TYPE: DNA
<213> ORGANISM: Homo Sapiens

<400> SEQUENCE: 73
aacaagtacg acgacaacgt c                                              21

<210> SEQ ID NO 74
<211> LENGTH: 21
<212> TYPE: DNA
<213> ORGANISM: Homo Sapiens

<400> SEQUENCE: 74
aacgtcaagg cctacttcaa g                                              21

<210> SEQ ID NO 75
<211> LENGTH: 24
<212> TYPE: DNA
<213> ORGANISM: Homo Sapiens
<220> FEATURE:
<221> NAME/KEY: misc_feature
<222> LOCATION: (3)..(3)
<223> OTHER INFORMATION: n is a, c, g, or t

<400> SEQUENCE: 75
sdnaatattc atacggcatg gact                                           24

<210> SEQ ID NO 76
<211> LENGTH: 21
<212> TYPE: DNA
<213> ORGANISM: Homo Sapiens

<400> SEQUENCE: 76
aacctaaaat agaagacccc t                                              21

<210> SEQ ID NO 77
<211> LENGTH: 21
<212> TYPE: DNA
<213> ORGANISM: Homo Sapiens
```

-continued

```
<400> SEQUENCE: 77
aaaagatgct gactcagaaa a                                              21

<210> SEQ ID NO 78
<211> LENGTH: 21
<212> TYPE: DNA
<213> ORGANISM: Homo Sapiens

<400> SEQUENCE: 78
aacctaaaat agaagacccc t                                              21

<210> SEQ ID NO 79
<211> LENGTH: 21
<212> TYPE: DNA
<213> ORGANISM: Homo Sapiens

<400> SEQUENCE: 79 aagacccta tgcaattagc t                                               21

<210> SEQ ID NO 80
<211> LENGTH: 21
<212> TYPE: DNA
<213> ORGANISM: Homo Sapiens

<400> SEQUENCE: 80
aaaaagcctg aagaacagca c                                              21

<210> SEQ ID NO 81
<211> LENGTH: 21
<212> TYPE: DNA
<213> ORGANISM: Homo Sapiens

<400> SEQUENCE: 81
aaatgggatt taatgcattc a                                              21

<210> SEQ ID NO 82
<211> LENGTH: 21
<212> TYPE: DNA
<213> ORGANISM: Homo Sapiens

<400> SEQUENCE: 82
aacttcatga ctgttgatca a                                              21

<210> SEQ ID NO 83
<211> LENGTH: 21
<212> TYPE: DNA
<213> ORGANISM: Homo Sapiens

<400> SEQUENCE: 83
aacatcatga gttgcgtcaa g                                              21

<210> SEQ ID NO 84
<211> LENGTH: 21
<212> TYPE: DNA
<213> ORGANISM: Homo Sapiens

<400> SEQUENCE: 84
aagcagcagg tccttaagaa c                                              21

<210> SEQ ID NO 85
<211> LENGTH: 21
<212> TYPE: DNA
<213> ORGANISM: Homo Sapiens
```

```
<400> SEQUENCE: 85
aatctcatca acaagtactt t                                          21

<210> SEQ ID NO 86
<211> LENGTH: 21
<212> TYPE: DNA
<213> ORGANISM: Homo Sapiens

<400> SEQUENCE: 86
aattcagaac gtcagcacct g                                          21

<210> SEQ ID NO 87
<211> LENGTH: 21
<212> TYPE: DNA
<213> ORGANISM: Homo Sapiens

<400> SEQUENCE: 87
aagaggagaa ctgacccaga a                                          21

<210> SEQ ID NO 88
<211> LENGTH: 21
<212> TYPE: DNA
<213> ORGANISM: Homo Sapiens

<400> SEQUENCE: 88
aaatgagcga ttggatggtg g                                          21

<210> SEQ ID NO 89
<211> LENGTH: 21
<212> TYPE: DNA
<213> ORGANISM: Homo Sapiens

<400> SEQUENCE: 89
aagatcatca agggctccag t                                          21

<210> SEQ ID NO 90
<211> LENGTH: 21
<212> TYPE: DNA
<213> ORGANISM: Homo Sapiens

<400> SEQUENCE: 90
aatgtggttc gaataattac a                                          21

<210> SEQ ID NO 91
<211> LENGTH: 21
<212> TYPE: DNA
<213> ORGANISM: Homo Sapiens

<400> SEQUENCE: 91
aaactcgaga tgactttgtg c                                          21

<210> SEQ ID NO 92
<211> LENGTH: 21
<212> TYPE: DNA
<213> ORGANISM: Homo Sapiens

<400> SEQUENCE: 92
aatcaacagc tgcagaggtt c                                          21

<210> SEQ ID NO 93
<211> LENGTH: 21
<212> TYPE: DNA
<213> ORGANISM: Homo Sapiens
```

```
<400> SEQUENCE: 93
aaggatggaa ctatcttatg c                                              21

<210> SEQ ID NO 94
<211> LENGTH: 21
<212> TYPE: DNA
<213> ORGANISM: Homo Sapiens

<400> SEQUENCE: 94
aatttcgacg atgccaccat g                                              21

<210> SEQ ID NO 95
<211> LENGTH: 21
<212> TYPE: DNA
<213> ORGANISM: Homo Sapiens

<400> SEQUENCE: 95
aaccgacaag tgtgacaact c                                              21

<210> SEQ ID NO 96
<211> LENGTH: 21
<212> TYPE: DNA
<213> ORGANISM: Homo Sapiens

<400> SEQUENCE: 96
aaagaaatgt gtggtcattg a                                              21

<210> SEQ ID NO 97
<211> LENGTH: 21
<212> TYPE: DNA
<213> ORGANISM: Homo Sapiens

<400> SEQUENCE: 97
aaatcgatgg aactatacat c                                              21

<210> SEQ ID NO 98
<211> LENGTH: 21
<212> TYPE: DNA
<213> ORGANISM: Homo Sapiens

<400> SEQUENCE: 98
aactatacat caggtgtatg t                                              21

<210> SEQ ID NO 99
<211> LENGTH: 21
<212> TYPE: DNA
<213> ORGANISM: Homo Sapiens

<400> SEQUENCE: 99
aatggtttca cccatcagag c                                              21

<210> SEQ ID NO 100
<211> LENGTH: 21
<212> TYPE: DNA
<213> ORGANISM: Homo Sapiens

<400> SEQUENCE: 100
aagggctcag ctacattcaa c                                              21

<210> SEQ ID NO 101
<211> LENGTH: 21
<212> TYPE: DNA
<213> ORGANISM: Homo Sapiens
```

<400> SEQUENCE: 101
aatacaacgt ccagcaacag t    21

<210> SEQ ID NO 102
<211> LENGTH: 22
<212> TYPE: DNA
<213> ORGANISM: Homo Sapiens

<400> SEQUENCE: 102
aactccatgt ttcataaacc gg    22

<210> SEQ ID NO 103
<211> LENGTH: 21
<212> TYPE: DNA
<213> ORGANISM: Homo Sapiens

<400> SEQUENCE: 103
aacgtgtatg gcttcgacat g    21

<210> SEQ ID NO 104
<211> LENGTH: 21
<212> TYPE: DNA
<213> ORGANISM: Homo Sapiens

<400> SEQUENCE: 104
aagttccaga aatctgaaat a    21

<210> SEQ ID NO 105
<211> LENGTH: 21
<212> TYPE: DNA
<213> ORGANISM: Homo Sapiens

<400> SEQUENCE: 105
aagaaaatcc agaacatgta g    21

<210> SEQ ID NO 106
<211> LENGTH: 21
<212> TYPE: DNA
<213> ORGANISM: Homo Sapiens

<400> SEQUENCE: 106
aaaacagtag cttcggagaa g    21

<210> SEQ ID NO 107
<211> LENGTH: 21
<212> TYPE: DNA
<213> ORGANISM: Homo Sapiens

<400> SEQUENCE: 107
aaggtaaaaa ggggtcacta t    21

<210> SEQ ID NO 108
<211> LENGTH: 21
<212> TYPE: DNA
<213> ORGANISM: Homo Sapiens

<400> SEQUENCE: 108
aaaggggtca ctatggagtt c    21

<210> SEQ ID NO 109
<211> LENGTH: 22
<212> TYPE: DNA
<213> ORGANISM: Homo Sapiens

```
<400> SEQUENCE: 109
agcaccagca ctggctcatc aa                                      22

<210> SEQ ID NO 110
<211> LENGTH: 19
<212> TYPE: DNA
<213> ORGANISM: Homo Sapiens

<400> SEQUENCE: 110
agagccagaa gagctgcta                                          19

<210> SEQ ID NO 111
<211> LENGTH: 20
<212> TYPE: DNA
<213> ORGANISM: Homo Sapiens

<400> SEQUENCE: 111
aaccgacaag tgtgacaact                                         20

<210> SEQ ID NO 112
<211> LENGTH: 18
<212> TYPE: DNA
<213> ORGANISM: Homo Sapiens

<400> SEQUENCE: 112
tgtgccttgc gggcagta                                           18

<210> SEQ ID NO 113
<211> LENGTH: 20
<212> TYPE: DNA
<213> ORGANISM: Homo Sapiens

<400> SEQUENCE: 113
caccaccacc accaaatgaa                                         20

<210> SEQ ID NO 114
<211> LENGTH: 20
<212> TYPE: DNA
<213> ORGANISM: Homo Sapiens

<400> SEQUENCE: 114
catccattcg acgcctttga                                         20

<210> SEQ ID NO 115
<211> LENGTH: 20
<212> TYPE: DNA
<213> ORGANISM: Homo Sapiens

<400> SEQUENCE: 115
ccagcagcac agtcaacaaa                                         20

<210> SEQ ID NO 116
<211> LENGTH: 20
<212> TYPE: DNA
<213> ORGANISM: Homo Sapiens

<400> SEQUENCE: 116
tggtagcttc tgcttcacaa                                         20

<210> SEQ ID NO 117
<211> LENGTH: 19
<212> TYPE: DNA
<213> ORGANISM: Homo Sapiens
```

-continued

```
<400> SEQUENCE: 117
ccagagctgc actcattcc                                                  19

<210> SEQ ID NO 118
<211> LENGTH: 22
<212> TYPE: DNA
<213> ORGANISM: Homo Sapiens

<400> SEQUENCE: 118
cactgttggt gataaagcaa tt                                              22

<210> SEQ ID NO 119
<211> LENGTH: 22
<212> TYPE: DNA
<213> ORGANISM: Homo Sapiens

<400> SEQUENCE: 119
ggataaaggc tacttaacaa ag                                              22

<210> SEQ ID NO 120
<211> LENGTH: 20
<212> TYPE: DNA
<213> ORGANISM: Homo Sapiens

<400> SEQUENCE: 120
ccactttgcc atctctacac                                                 20

<210> SEQ ID NO 121
<211> LENGTH: 18
<212> TYPE: DNA
<213> ORGANISM: Homo Sapiens

<400> SEQUENCE: 121
gagccgagga ggttgaag                                                   18

<210> SEQ ID NO 122
<211> LENGTH: 20
<212> TYPE: DNA
<213> ORGANISM: Homo Sapiens

<400> SEQUENCE: 122
ctcctctggg tctatagtgt                                                 20

<210> SEQ ID NO 123
<211> LENGTH: 18
<212> TYPE: DNA
<213> ORGANISM: Homo Sapiens

<400> SEQUENCE: 123
gaccctggtg gcggtgaa                                                   18

<210> SEQ ID NO 124
<211> LENGTH: 19
<212> TYPE: DNA
<213> ORGANISM: Homo Sapiens

<400> SEQUENCE: 124
ggtgcctgca gcatcttca                                                  19

<210> SEQ ID NO 125
<211> LENGTH: 18
<212> TYPE: DNA
<213> ORGANISM: Homo Sapiens
```

```
<400> SEQUENCE: 125
ggagagccct ggcacgta                                              18

<210> SEQ ID NO 126
<211> LENGTH: 20
<212> TYPE: DNA
<213> ORGANISM: Homo Sapiens

<400> SEQUENCE: 126
ccttcatctg caggttcttg                                            20

<210> SEQ ID NO 127
<211> LENGTH: 21
<212> TYPE: DNA
<213> ORGANISM: Homo Sapiens

<400> SEQUENCE: 127
acgacggaca cattaattac t                                          21

<210> SEQ ID NO 128
<211> LENGTH: 19
<212> TYPE: DNA
<213> ORGANISM: Homo Sapiens

<400> SEQUENCE: 128
tccatgctgc agctgatga                                             19

<210> SEQ ID NO 129
<211> LENGTH: 19
<212> TYPE: DNA
<213> ORGANISM: Homo Sapiens

<400> SEQUENCE: 129
ccttcggcaa agggagagt                                             19

<210> SEQ ID NO 130
<211> LENGTH: 21
<212> TYPE: DNA
<213> ORGANISM: Homo Sapiens

<400> SEQUENCE: 130
ctggatgagt tcagagagtt t                                          21

<210> SEQ ID NO 131
<211> LENGTH: 18
<212> TYPE: DNA
<213> ORGANISM: Homo Sapiens

<400> SEQUENCE: 131
gcctcgacag gcagagat                                              18

<210> SEQ ID NO 132
<211> LENGTH: 21
<212> TYPE: DNA
<213> ORGANISM: Homo Sapiens

<400> SEQUENCE: 132
cttgtagctg aagatgtcaa t                                          21

<210> SEQ ID NO 133
<211> LENGTH: 19
<212> TYPE: DNA
<213> ORGANISM: Homo Sapiens
```

```
<400> SEQUENCE: 133
ctctatgccc gggacaagt                                                    19

<210> SEQ ID NO 134
<211> LENGTH: 21
<212> TYPE: DNA
<213> ORGANISM: Homo Sapiens

<400> SEQUENCE: 134
aagacatgtc gaagccatac a                                                 21

<210> SEQ ID NO 135
<211> LENGTH: 21
<212> TYPE: DNA
<213> ORGANISM: Homo Sapiens

<400> SEQUENCE: 135
aatgtcatcc acgccagcga c                                                 21

<210> SEQ ID NO 136
<211> LENGTH: 21
<212> TYPE: DNA
<213> ORGANISM: Homo Sapiens

<400> SEQUENCE: 136
aatggaaagt gcgtcatcct a                                                 21

<210> SEQ ID NO 137
<211> LENGTH: 21
<212> TYPE: DNA
<213> ORGANISM: Homo Sapiens

<400> SEQUENCE: 137
aagttcacaa ttggcgacca c                                                 21

<210> SEQ ID NO 138
<211> LENGTH: 21
<212> TYPE: DNA
<213> ORGANISM: Homo Sapiens

<400> SEQUENCE: 138
aagtgcttca gcatcgacaa c                                                 21

<210> SEQ ID NO 139
<211> LENGTH: 21
<212> TYPE: DNA
<213> ORGANISM: Homo Sapiens

<400> SEQUENCE: 139
aagagttacc tagaagcacc t                                                 21

<210> SEQ ID NO 140
<211> LENGTH: 21
<212> TYPE: DNA
<213> ORGANISM: Homo Sapiens

<400> SEQUENCE: 140
aaaaaaccga atcttcaggt c                                                 21

<210> SEQ ID NO 141
<211> LENGTH: 21
<212> TYPE: DNA
<213> ORGANISM: Homo Sapiens
```

-continued

```
<400> SEQUENCE: 141
aaactctctg aactcatcca g                                              21

<210> SEQ ID NO 142
<211> LENGTH: 21
<212> TYPE: DNA
<213> ORGANISM: Homo Sapiens

<400> SEQUENCE: 142
aactggatcc aaaaaaccat t                                              21

<210> SEQ ID NO 143
<211> LENGTH: 21
<212> TYPE: DNA
<213> ORGANISM: Homo Sapiens

<400> SEQUENCE: 143
aatgaccgtt acattgtcaa t                                              21

<210> SEQ ID NO 144
<211> LENGTH: 21
<212> TYPE: DNA
<213> ORGANISM: Homo Sapiens

<400> SEQUENCE: 144
aaaatatggg aacctacaat a                                              21
```

METHODS FOR ASSESSING CISPLATIN RESISTANCE, DISEASE PROGRESSION, AND TREATMENT EFFICACY IN OVARIAN CANCER

This application is related to and claims priority to U.S. provisional application Ser. No. 60/533,505 filed Dec. 31, 2003, the disclosure of which is incorporated by reference herein.

FIELD OF THE INVENTION

The invention relates to methods for predicting whether an ovarian cancer patient will be resistant to chemotherapy and methods for determining whether an individual patient has colon cancer. The invention also relates to methods for monitoring the effectiveness of therapy in a patient treated for ovarian cancer. The invention further relates to methods for treating ovarian cancer and colon cancer. In addition, the invention relates to methods of screening for compounds that can inhibit growth of tumor cells, particularly ovarian cancer cells or colon cancer cells. The invention also relates to methods for reducing or inhibiting resistance to chemotherapeutic drug treatment or therapy, particularly in ovarian cancer cells that are resistant to conventional chemotherapeutic treatment regimes.

BACKGROUND OF THE INVENTION

Ovarian cancer is the most lethal of gynecological malignancies with a mortality rate of 60%. The five-year survival rates for the various clinical stages of the disease are as follows: Stage I>90%, Stage II=80%, Stage III=20% and Stage IV=10%; there is a significant drop in the survival rates at later stages of the disease. Standard-of-care treatment for advanced stages of the disease includes cytoreductive surgery followed by chemotherapy.

For most patients there is a low probability of surviving, since approximately 75% of all patients are diagnosed at stages III and IV of the disease, and poor prognosis is associated with late diagnosis of the disease at its advanced stages. Resistance to currently-available chemotherapeutic agents is another major problem. Although complete clinical response is achieved in 75% of patients after initial treatment, most will develop recurrent disease and require re-treatment. Unfortunately, the overwhelming majority will eventually develop chemoresistance and succumb to the disease.

Chemoresistance is a complex phenomenon that involves a change in the expression and biological activity of several genes and gene products. The genes or gene families that are expressed differently in responsive and non-responsive individuals can be used as molecular markers for predicting which patients might be resistant to a particular chemotherapeutic agent or combination thereof, as is typically used clinically. In addition, genes that are overexpressed in chemoresistant individuals can be targets for inhibition, which may decrease resistance of a cancer cell to a chemotherapeutic agent or agents.

As with ovarian cancer, the survival of patients with colorectal cancer is best when the disease is diagnosed early. If the cancer is detected early, the 5-year survival rate for colon cancer patients is approximately 90%; unfortunately, despite increased surveillance and preventative measures, only 37% of cancers are found at this early stage. When the cancer has spread regionally to involve other organs the survival rate drops to around 64% and it is drastically lowered (8%) after the cancer has metastasized (Cancer Facts and Figures 2002; American Cancer Society publication).

Thus, there is a need for identifying colon and ovarian cancers early in the course of the disease process, and a particular need for identifying cancers that are chemoresistant. More specifically, since it is understood in the art that the behavior of cancer cells, both regarding their tumorigenicity and their resistance to chemotherapeutic drugs is mediated by the expression of a not completely defined set of particular genes, there is a need in the art to identify genes and collections or sets of genes that serve as effective molecular markers for chemoresistance in ovarian cancer, as well as such genes or gene sets that provide clinically effective therapeutic targets for ovarian cancer and colon cancer.

SUMMARY OF THE INVENTION

This invention provides methods and reagents for identifying genes involved in, or whose expression is modulated by, or wherein said modulated expression is associated with or responsible for resistance to chemotherapeutic drug treatment. In particular, the invention provides genes involved with, or whose expression is so modulated, or wherein said modulated expression is associated with or responsible for resistance to chemotherapeutic drug treatment, as well as patterns of modulated gene expression of a plurality of genes wherein said patterns are characteristic of chemotherapeutic drug resistant cells, particularly drug-resistant ovarian cancer cells. The invention further provides methods for identifying compounds that interact with or affect expression or activity of one or a plurality of said genes. Also provided are said compounds that are useful as alternatives to or in conjunction with chemotherapeutic agents for treating ovarian cancer, particularly such cancers that are or have become resistant to conventional chemotherapeutic treatment. The invention further provides methods and reagents for monitoring chemotherapeutic treatment to identify patients whose tumors are or have become resistant to chemotherapeutic agents.

The invention provides methods for identifying compounds that decrease chemotherapeutic drug resistance and inhibit, retard or prevent growth of tumor cells, most preferably ovarian cancer cells, that are resistant to a chemotherapeutic agent, the method comprising the steps of: (a) contacting with a test compound a chemotherapeutic drug resistant cell growing in the presence of a chemotherapeutic drug for a time or at a concentration wherein the cell is resistant to the drug and wherein the cell expresses at least one gene that is overexpressed in chemoresistant ovarian cancer cells, wherein the overexpressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1 or KIAA0082 (as identified by the GenBank accession numbers set forth in Table 1); (b) assaying said cells for expression or activity of one or a plurality of said genes or gene products in the presence and absence of the test compound; and/or (c) comparing cell growth and/or expression or activity of at least one of the genes or gene products in the presence and absence of the test compound, wherein a compound is identified as a compound that inhibits chemoresistant tumor cell growth if expression or activity of the gene or gene product in the presence of the test compound is reduced relative to expression of the gene in the absence of the test compound, or if cell growth is inhibited in the presence of the compound, or both. In certain embodiments, gene expression is detected by assaying a biological sample using an array of, inter alia, nucleic acid (gene) probes or antibodies specific for a plurality of gene products identified herein.

Further, the invention provides methods for identifying compounds that decrease drug resistance and inhibit, retard or prevent growth of tumor cells, most preferably ovarian cancer cells, that are resistant to a chemotherapeutic agent, the method comprising the steps of: a) contacting with a test compound a cell growing in the presence of a chemotherapeutic drug for a time or at a concentration wherein the cell is resistant to the drug and wherein the cell expresses a gene that is expressed at a lower level in chemoresistant ovarian cancer cells compared with a chemo-sensitive cell, wherein the gene is HMT1, NAIP, eEF1ε, RAB22A, NCOR2, MT1 or MPP10 (as identified by the GenBank accession numbers set forth in Table 1); b) assaying said cells for cell growth and/or gene expression or gene product activity in the presence and absence of the test compound; and c) comparing expression of the gene or activity of the gene product in the presence and absence of the test compound, wherein a compound is identified as a compound that inhibits chemoresistant tumor cell growth if (i) expression of the gene or activity of the gene product in the presence of the test compound is increased relative to expression of the gene or activity of the gene product in the absence of the test compound, and/or (ii) if cell growth is inhibited in the presence of the compound, and/or (iii) if cell growth is inhibited while expression and/or activity of the gene are increased. In certain embodiments, gene expression is detected by assaying a biological sample using an array of, inter alia, nucleic acid (gene) probes or antibodies specific for a plurality of gene products identified herein.

The invention provides methods for decreasing drug resistance, or inhibiting, retarding or preventing growth of a tumor cell, or both, comprising the step of contacting the tumor cell with at least one inhibitor of a cellular gene, wherein the cellular gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1 or KIAA0082 in the presence of a chemotherapeutic drug for a time or at a concentration wherein the cell is resistant to the drug in the absence of the cellular gene inhibitor. In preferred embodiments, the tumor cell is a human tumor cell, and more preferably an ovarian cancer cell. In particular aspects, one or a plurality of the genes identified according to the invention are inhibited with antisense RNA or siRNA molecules specifically designed to target one or a plurality of said genes. In alternative aspects, the gene products of said genes are inhibited using inhibitors of these proteins.

The invention provides methods for decreasing drug resistance of a tumor cell, comprising the step of contacting the tumor cell with at least one compound that increases expression or activity of a cellular gene, wherein the cellular gene is HMT1, NAIP, eEF1ε, RAB22A, NCOR2, MT1, or MPP10, in the presence or absence of a chemotherapeutic drug for a time or at a concentration wherein the cell is resistant to the drug in the absence of the compound that increases expression or activity of a HMT1, NAIP, eEF1ε, RAB22A, NCOR2, MT1, or MPP10. In preferred embodiments, the tumor cell is a human tumor cell, and more preferably an ovarian cancer cell.

The invention also provides methods for inhibiting, retarding or preventing growth of a tumor cell, comprising the step of contacting the tumor cell with at least one compound that increases expression or activity of a cellular gene, wherein the cellular gene is HMT1, NAIP, eEF1ε, RAB22A, NCOR2, MT1, or MPP10, in the presence or absence of a chemotherapeutic drug for a time or at a concentration wherein cell proliferation is slowed or inhibited in the presence of the compound that increases expression or activity of a HMT1, NAIP, eEF1ε, RAB22A, NCOR2, MT1, or MPP10 compared with cell proliferation in the absence said compound. In preferred embodiments, the tumor cell is a human tumor cell, and more preferably an ovarian cancer cell.

In another aspect, the invention provides methods for inhibiting, retarding or preventing growth of a tumor cell, most preferably an ovarian cancer cell, the method comprising the step of contacting the tumor cell with a combination of a chemotherapeutic agent or agents and at least one inhibitor of a cellular gene, wherein the cellular gene is S100A10, S100A11, Calpain 2, SPARC, MetAP2, KLK6, ARA9, Calponin 2, RNPS1, eIF5, eIF2Bε, WDR1, Fused toes, NM23D, Grancalcin, SAPK/Erk1, zinc finger protein-262 MYM, HYA22, Vinexin β, G-CSFR, IGFBP-7, or KIAA0082. In a particular aspect, the cellular gene is MetAP2, the chemotherapeutic agent is platinum-based, and the at least one inhibitor is fumagillin or a derivative of fumagillin. In another particular aspect, the cellular gene is Calpain 2, the chemotherapeutic agent is platinum-based, and the at least one inhibitor is N-acetyl-leucyl-leucyl-norleucinal (ALLN) or a derivative thereof. An inhibitor of a cellular gene shown in Table 1 can be, for example, a siRNA molecule or an shRNA molecule that is specifically designed to target a gene shown in Table 1, or a small molecule inhibitor.

In another aspect, the invention provides methods for inhibiting, retarding or preventing growth of a tumor cell, most preferably an ovarian cancer cell, the method comprising the step of contacting the tumor cell with a combination of a chemotherapeutic agent or agents and at least one compound that increases expression or activity of a cellular gene, wherein the cellular gene is HMT1, NAIP, eEF1ε, RAB22A, NCOR2, MT1, or MPP10. In preferred embodiments, the tumor cell is a human tumor cell, and more preferably an ovarian cancer cell.

The invention also provides methods of predicting whether an ovarian cancer patient's tumor will be resistant to chemotherapeutic treatment, comprising the steps of: (a) detecting an amount of one or a plurality of expressed genes or gene products encoded thereby in a biological sample taken from the patient, wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) detecting an amount of the one or the plurality of expressed genes or gene products encoded thereby in a control sample comprising a nontumor tissue sample, most preferably from the tissue of origin of the tumor, or a tissue sample from a patient that responded well to chemotherapy, corresponding to the one or plurality of expressed genes or gene products detected in subpart (a), wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; and (c) comparing the amount of the expressed gene or gene product measured in step (a) with the amount of the expressed gene or gene product detected in step (b), wherein the patient is predicted to be resistant to chemotherapy if the amount detected in step (a) is greater than the amount detected in step (b) by a factor of at least 20%. In a particular aspect, the biological sample is a tumor sample. In a particular aspect, the control sample is a biological sample obtained from a cancer patient who is responsive to chemotherapy. In certain embodiments, gene expression is detected by assaying a biological sample using an array of, inter alia, nucleic acid (gene) probes or antibodies specific for a plurality of gene products identified herein.

In a particular aspect, the method predicts that a patient will be resistant to platinum-based chemotherapy when the measured amount of MetAP2 expressed in the biological sample from the cancer patient is greater than the amount detected in a chemotherapeutic drug responsive individual or in ovarian tissue from an individual without ovarian cancer.

The invention also provides methods of predicting whether an ovarian cancer patient's tumor will be resistant to chemotherapeutic treatment, comprising the steps of: (a) detecting an amount of one or a plurality of expressed genes or gene products encoded thereby in a biological sample taken from the patient, wherein the expressed gene is HMT1, NAIP, eEF1ε, RAB22A, NCOR2, MT1, or MPP10; (b) detecting an amount of the one or the plurality of expressed genes or gene products encoded thereby in a control sample corresponding to the one or plurality of expressed genes or gene products detected in subpart (a), wherein the expressed gene is HMT1, NAIP, eEF1ε, RAB22A, NCOR2, MT1 or MPP10; and (c) comparing the amount of the expressed gene or gene product measured in step (a) with the amount of the expressed gene or gene product detected in step (b), wherein the patient is predicted to be resistant to chemotherapy if the amount detected in step (a) is less than the amount detected in step (b) by a factor of at least 20%, more preferably at least 50%. In a particular aspect, the control sample is a biological sample obtained from a cancer patient who is responsive to chemotherapy. In a particular aspect, the biological sample is a tumor sample. In certain embodiments, gene expression is detected by assaying a biological sample using an array of, inter alia, nucleic acid (gene) probes or antibodies specific for a plurality of gene products identified herein.

The invention further provides methods for monitoring disease progression in an ovarian cancer patient, particularly an ovarian cancer patient being treated with a chemotherapeutic treatment, comprising the steps of: (a) detecting an amount of one or a plurality of expressed genes or gene products encoded thereby in a biological sample taken from the patient, wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) repeating step (a) using a subsequently-collected biological sample obtained from the patient; and (c) comparing the amount of expressed gene or gene product detected in step (a) with the amount of expressed gene or gene product detected in step (b), wherein disease progression is monitored by detecting changes in the amount of expressed gene or gene products in the subsequently-collected biological sample compared with the biological sample taken in step (a), and whereby disease progression is detected when the amount of the expressed gene or expressed gene product detected in step (b) is greater than the amount of the expressed gene or gene product detected in step (a). In certain embodiments, the patient undergoes chemotherapeutic or other treatment during the period between detecting the amount of gene expression in step (a) and the amount detected in step (b). In a particular aspect, the biological sample is a tumor sample. In preferred embodiments, gene expression is detected by assaying a biological sample using an array of, inter alia, nucleic acid (gene) probes or antibodies specific for a plurality of gene products identified herein.

The invention further provides methods for monitoring disease progression in an ovarian cancer patient, particularly an ovarian cancer patient being treated with a chemotherapeutic treatment, comprising the steps of: (a) detecting an amount of one or a plurality of expressed genes or gene products encoded thereby in a biological sample taken from the patient, wherein the expressed gene is HMT1, NAIP, eEF1ε, RAB22A, NCOR2, MT1 or MPP10; (b) repeating step (a) using a subsequently-collected biological sample obtained from the patient; and (c) comparing the amount of expressed gene or gene product detected in step (a) with the amount of expressed gene or gene product detected in step (b), wherein disease progression is monitored by detecting changes in the amount of expressed gene or gene products in the subsequently-collected biological sample compared with the biological sample taken in step (a), and whereby disease progression is detected when the amount of the expressed gene or expressed gene product detected in step (b) is less than or equal to the amount of the expressed gene or gene product detected in step (a). In certain embodiments, the patient undergoes chemotherapeutic or other treatment during the period between detecting the amount of gene expression in step (a) and the amount detected in step (b). In a particular aspect, the biological sample is a tumor sample. In certain embodiments, gene expression is detected by assaying a biological sample using an array of, inter alia, nucleic acid (gene) probes or antibodies specific for a plurality of gene products identified herein.

In addition, the invention provides methods for monitoring the effectiveness of a pharmaceutical composition as an agent for treating cancer, particularly ovarian or colon cancer in a patient comprising the steps of: (a) detecting an amount of one or a plurality of expressed genes or gene products encoded thereby in a biological sample taken from a patient, wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) administering an amount a pharmaceutical composition to the patient; (c) repeating step (a) using a subsequently-collected biological sample obtained from the patient; and (d) comparing the amount of expressed gene or gene product detected in step (a) with the amount of expressed gene or gene product detected in step (c), wherein the effectiveness of the pharmaceutical composition is monitored by detecting changes in the amount of expressed gene or gene products in the subsequently-collected biological sample compared with the biological sample taken in step (a), and whereby the pharmaceutical composition is effective when the amount of the expressed gene or expressed gene product detected in step (c) is less than the amount of the expressed gene or gene product detected in step (a) and where growth of the tumor is decreased (i.e., slowed, retarded or inhibited) in the presence of the pharmaceutical composition. In a particular aspect, the biological sample is a tumor sample. In certain embodiments, gene expression is detected by assaying a biological sample using an array of, inter alia, nucleic acid (gene) probes or antibodies specific for a plurality of gene products identified herein.

The invention also provides methods for monitoring the effectiveness of a pharmaceutical composition as an agent for treating cancer, particularly ovarian cancer in a patient comprising the steps of: (a) detecting an amount of one or a plurality of expressed genes or gene products encoded thereby in a biological sample taken from a patient, wherein the expressed gene is HMT1, NAIP, eEF1ε, RAB22A, NCOR2, MT1 or MPP10; (b) administering an amount a pharmaceutical composition to the patient; (c) repeating step (a) using a subsequently-collected biological sample obtained from the patient; and (d) comparing the amount of expressed gene or gene product detected in step (a) with the amount of expressed gene or gene product detected in step (c), wherein the effectiveness of the pharmaceutical composition is monitored by detecting changes in the amount of expressed gene or gene products in the subsequently-collected biological sample compared with the biological sample taken in step (a), and whereby the pharmaceutical composition is effective when the amount of the expressed gene or expressed gene product detected in step (c) is greater than the amount of the expressed gene or gene product detected in step (a) and whereby growth of the tumor is decreased (i.e., slowed, retarded or inhibited) in the presence of the pharmaceutical composition. In a particular aspect, the biological sample is a tumor sample. In certain embodiments, gene expression is detected by assaying a biological sample using an array of, inter alia, nucleic acid (gene) probes or antibodies specific for a plurality of gene products identified herein.

The invention also provides a method of detecting colon cancer comprising the steps of: (a) obtaining a biological sample from an animal, preferably a human; (b) detecting an amount of one or a plurality of expressed genes or gene products encoded thereby in the biological sample, wherein the expressed gene is S100A10, S100A11, Calpain 2, SPARC, or MetAP2; (c) detecting an amount of the one or plurality of expressed genes or gene products detected in a control sample comprising a nontumor colon tissue sample; (d) comparing the amount the one or plurality of expressed genes or gene products from step (b) with the amount in step (c), wherein colon cancer is detected if there is a difference in the amount in step (b) compared with the amount in step (c). The difference detected can be overexpression of the one or plurality of said genes, or can be lack of or underexpression of the one or plurality of said genes, in the biological sample taken in step (a) compared with the biological sample taken in step (c). For example, colon cancer is detected if the amount of S100A10, S100A11, SPARC, and/or MetAP2 is greater in step (b) compared with the amount in step (c), and/or if the amount of Calpain 2 is less in step (b) than the amount in step (c). In certain embodiments, the animal is a human, preferably a human having colon cancer. Preferably, the biological sample is a colon tissue sample, more preferably a polyp and yet more preferably an adematous polyp, which are commonly used in the art as tissue samples for colon screening activities. In certain embodiments, gene expression is detected by assaying a biological sample using an array of, inter alia, nucleic acid (gene) probes or antibodies specific for a plurality of gene products identified herein.

In yet another embodiment, the invention provides methods for diagnosing cancer and/or chemotherapeutic drug resistance in an animal, preferably a human, comprising the step of detecting a pattern of changes in amount of two or a plurality of expressed genes or gene products encoded thereby. In a particular embodiment, the expressed genes are genes shown in Table 1. Generally, these methods of the invention comprise the steps of: (a) obtaining a biological sample from an animal, preferably a human; (b) detecting an amount of two or a plurality of expressed genes or gene products encoded thereby in the biological sample, wherein the expressed gene is shown in Table 1; (c) detecting an amount of the two or plurality of expressed genes or gene products detected in a control sample; (d) determining a pattern of changes in the amount of the two or a plurality of expressed genes or gene products encoded thereby by comparing the amount the two or plurality of expressed genes or gene products from step (b) with the amount in step (c), wherein the pattern is associated with a cancer, for example colon or ovarian cancer, or drug resistance, for example resistance to cis-platin. In certain embodiments, gene expression is detected by assaying a biological sample using an array of, inter alia, nucleic acid (gene) probes or antibodies specific for a plurality of gene products identified herein.

The invention also provides methods for detecting chemotherapeutic drug resistance in an animal with ovarian cancer, the method comprising the steps of (a) detecting an amount of a plurality of expressed genes or gene products encoded thereby in a biological sample taken from the animal, wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) detecting an amount of the said plurality of expressed genes or gene products encoded thereby in a control sample comprising nontumor ovarian tissue or tumor tissue from a patient responsive to chemotherapy, corresponding to the plurality of expressed genes or gene products detected in subpart (a), wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; and (c) comparing the amount of the expressed gene or gene product measured in step (a) with the amount of the expressed gene or gene product detected in step (b), wherein the patient is predicted to be resistant to chemotherapy if the amount detected in step (a) is greater than the amount detected in step (b) by a factor of at least 20%. As provided herein, the plurality of said genes wherein the amount detected in step (a) is greater than the amount detected in step (b) by a factor of at least 20% defines a gene expression pattern specific for tumor samples that are resistant to a chemotherapeutic drug. In a particular aspect, the control sample is a biological sample obtained from a cancer patient who is responsive to chemotherapy. Preferably, expression of one or a plurality of said genes is greater in the tumor sample detected in step (a) than in the control sample detected in step (b). In preferred embodiments, the animal is a human, most preferably a human cancer patient. As disclosed herein, the invention further provides a gene expression pattern that predicts resistance to said chemotherapeutic drug when said gene expression pattern is detected. In preferred embodiments, gene expression is detected by assaying a biological sample using an array of, inter alia, nucleic acid (gene) probes or antibodies specific for a plurality of gene products identified herein.

Advantageously, some genes identified herein have never been recognized as associated with either ovarian or colon cancer and may prove to be novel targets for intervention with these diseases.

Specific preferred embodiments of the invention will become evident from the following more detailed description of certain preferred embodiments and the claims.

BRIEF DESCRIPTION OF THE DRAWINGS

FIG. 41 (lower panel) depicts a graph showing that there was an enhancement of the effect of cis-platin in the presence of 0.1 μg/ml fumagillin but not when the cells were treated with cis-platin in the presence of 10 μg/ml fumagillin for 8 hours.

FIG. 42 (lower panel) depicts a graph showing that there was an enhancement of the cytotoxic effect of cis-platin in the presence of 0.1 μg/ml fumagillin but not when the cells were treated with cis-platin in the presence of 10 μg/ml fumagillin for 24 hours.

Figure 1:
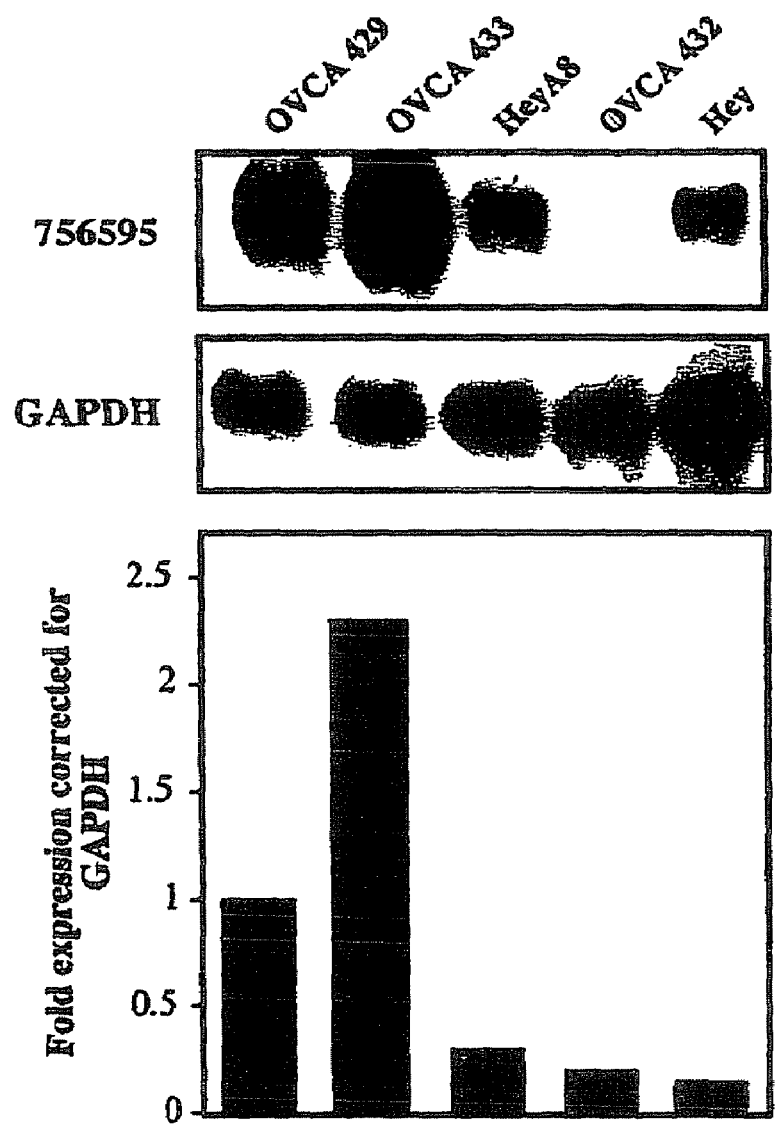
FIG. 1 is a photograph of an autoradiogram showing the results of Northern blot analysis, and a graphical representation of the Northern blot results demonstrating that S100A10 is expressed at increased levels in ovarian cancer cell lines that have increased resistance to chemotherapeutic drug(s).

mRNA expression of Calpain 2 and S100A11 was greatly reduced in the relevant siRNA lanes.

DETAILED DESCRIPTION OF THE PREFERRED EMBODIMENTS

The invention provide methods for inhibiting, retarding or preventing growth of a tumor cell, comprising the step of contacting the tumor cell in the presence of a chemotherapeutic drug at a concentration to which the cell is resistant with at least one modulator of expression or activity of one or a plurality of cellular genes, wherein the cellular gene is a gene shown in Table 1, and wherein contacting the tumor cell with said gene expression modulator reduces, inhibits, retards or prevents drug resistance in the tumor cell. The tumor cell can be for example, an ovarian cancer. In one embodiment, the tumor cell can be contacted in vivo (e.g. a cell that has not been removed from a patient).

The term "biological sample" as used herein includes, but is not limited to, a tissue or bodily fluid obtained from an animal, preferably a mammal and most preferably a human. For example, a biological sample can be biopsy material, bone marrow samples, blood, blood plasma, serum or cellular fraction thereof, urine, saliva, tears, or cells derived from a biological source. In one embodiment, the mammal is a human suspected of having or previously diagnosed as having or in need of screening for a cancer, in particular ovarian or colon cancer. In certain embodiments, a biological sample is a tumor sample.

As used herein, the term "ovarian cancer" will be understood to refer generally to epithelial ovarian cancer, which comprises some 80% of all diagnosed human cancer from ovarian tissues. The remainder, comprising germline-derived ovarian cancer and clear cell ovarian cancer, are rare, and frequently misdiagnosed. Insofar as the changes in gene expression disclosed herein are also found in these minor tumor types, the methods and compositions of the inventions apply thereto.

As used herein, a "modulator" of gene expression or gene product activity can be any chemical compound, nucleic acid molecule, peptide or polypeptide that can cause an increase or decrease in expression of a gene or activity of a gene product. In certain embodiments, a modulator of the invention is a compound that causes an increase in the expression or activity of one or a plurality of cellular genes whose expression or activity is decreased in tumor cells that are resistant to chemotherapeutic agents; such modulators are termed "activators" herein. In other embodiments, a modulator is an inhibitor of expression or activity of one or a plurality of cellular genes, particularly a gene whose expression is increased in tumor cells that are resistant to chemotherapeutic agents; such modulators are termed "inhibitors" herein.

As used herein, an "inhibitor" can be any chemical compound, nucleic acid molecule, peptide or polypeptide such as an antibody against a gene product that can reduce activity of a gene product or directly interfere with expression of a gene. An inhibitor of the invention, for example, can inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. Furthermore, an inhibitor of the invention can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

As used herein, an "activator" can be any chemical compound, nucleic acid molecule, peptide or polypeptide can enhance activity of a gene product (e.g., by stabilizing the gene product, preventing its proteolytic degradation or increasing its enzymatic or binding activity or directly activating expression of a gene). An activator of the invention can increase the activity of a protein that is encoded by a gene either directly or indirectly. Direct activation can be accomplished, for example, by binding to a protein and thereby enhancing binding of the protein to an intended target, such as a receptor. Indirect activation can be accomplished, for example, by binding to a protein's intended target, such as a receptor or binding partner, and enhancing activity, e.g. by increasing the effective concentration of the target. Furthermore, an activator of the invention can activate a gene by increasing expression of the gene, e.g., by increasing gene expression (transcription, processing, translation, post-translational modification), for example, by stabilizing the gene's mRNA or blocking degradation of the mRNA transcript, or by post-translational modification of a gene product, or by causing changes in intracellular localization.

As described herein, the expression of several genes in chemoresistant ovarian tumor cells differs substantially from expression thereof in chemosensitive ovarian tumor cells. Table 1 provides a list of such genes identified using methods described in the Examples below. The Table also summarizes expression patterns of these genes in cells sensitive or resistant to cis-platin, a widely used chemotherapeutic agent.

TABLE 1

| GenBank Accession # | Names | Chromosomal location | Protein information | Expression pattern as validated in cell lines |
|---|---|---|---|---|
| BC015973 | S100A10 p11 CLP11 Calpactin 1 light chain 42C | 1q21.3 | Extracellular 96 amino acids | Increased with increased resistance to cis-platin |
| BC001410 | S100A11 S100C Calgizzarin | 1q21.3 | Extracellular 105 amino acids | Increased with increased resistance to cis-platin |

TABLE 1-continued

| GenBank Accession # | Names | Chromosomal location | Protein information | Expression pattern as validated in cell lines |
|---|---|---|---|---|
| AF261089 | Calpain 2 CANPL2 MCANP | 1q41-q42.11 | Cytoplasmic and Cell membrane 700 amino acids | Increased with increased resistance to cis-platin |
| BC004974 | SPARC Osteonectin BM-40 | 5q31.3-q33.1 | Extracellular 303 amino acids | Increased with increased resistance to cis-platin |
| BC013782 | MetAP2 p67eIF2 MNPEP | 12q22 | Cytoplasmic 478 amino acids | Increased with increased resistance to cis-platin |
| BC015525 | KLK6 Zyme Neurosin Protease M | 19q13.33 | Extracellular 244 amino acids | Increases with increased resistance to cis-platin |
| AF222689 | HMT1 HMT2 ANM1 HCP1 | 19q13.33 | Nuclear 361 amino acids | Decreased with increased resistance to cis-platin |
| U31913 | ARA9 XAP2 | 11q13.3 | Cytoplasmic 330 amino acids | Increased with increased resistance to cis-platin |
| D83735 | Calponin 2 | 19p13.3 | Cytoplasmic 309 amino acids | Increased with increased resistance to cis-platin |
| U19251 | NAIP | 5q13.1-13.2 | Cytoplasmic 1403 amino acids | Decreased with increased resistance to cis-platin |
| BC005291 | eEF1ε p18 | 6p24.3-p25.1 | Cytoplasmic 174 amino acids | Decreased with increased resistance to cis-platin |
| AF015608 | RNPS1 | 16p13.3 | Cytoplasmic | Increased with increased resistance to cis-platin |
| U49436 | eIF5 eIF5A | 14q32.32 | Cytoplasmic 431 amino acids | Increased with increased resistance to cis-platin |
| BC013590 | eIF2Bε | 3q27.1 | Cytoplasmic 721 amino acids | Increased with increased resistance to cis-platin |
| M65217 | HSF2 HSTF2 | 6q22.31 | Cytoplasmic and Nuclear 536 amino acids | Increased with increased resistance to cis-platin |
| AB010427 | WDR1 NORI-1 | 4p16.1 | Cytoplasmic 606 amino acids | Increased with increased resistance to cis-platin |
| BC001134 | Fused toes (Ft1) | 16q12.2 | Unknown 292 amino acids | Increased with increased resistance to cis-platin |
| BC004880 | NM23D mn23-H4 | 16p13.3 | Mitochondrial inter-membrane space 187 amino acids | Increased with increased resistance to cis-platin |
| U10439 | ADAR1 | 1q21.1-q21.2 | Nuclear 1226 amino acids | Increased with increased resistance to cis-platin |
| BC005214 | Grancalcin | 2q24.2 | Cytoplasmic/ Membranes 217 amino acids | Increased with increased resistance to cis-platin |
| BC009808 | NBR1 | 17q21.1-q21.31 | 966 amino acids | Increased with increased resistance to cis-platin |
| L36870 | SAPK/Erk1 JNKK1 MEK4 MKK4 MAPKK4 | 17p11.2-p12 | Cytoplasmic 399 amino acids | Increased with increased resistance to cis-platin |
| AB007885 | Zinc finger protein-262 MYM | 1p32-p34.3 | Unknown | Increased with increased resistance to cis-platin |
| D88153 | HYA22 | 3p21.3 | Unknown | Increased with increased resistance to cis-platin |
| AB049635 | MRPL4 CGI-28 | 19p13.2 | Mitochondrial | Increased with increased resistance to cis-platin |

TABLE 1-continued

| GenBank Accession # | Names | Chromosomal location | Protein information | Expression pattern as validated in cell lines |
|---|---|---|---|---|
| AF037261 | Vinexin β | 8p21.3 | Associated with Cytoskeleton | Increased with increased resistance to cis-platin |
| M59818 | G-CSFR | 1p35-34.3 | Cell membrane or soluble form 836 amino acids | Increased with increased resistance to cis-platin |
| BC015710 | RAB22A | 20q13.32 | Membrane associated 194 amino acids | Decreased with increased resistance to cis-platin |
| BC017201 | IGFBP-7 MAC25 FSTL2 | 4q12 | Secreted 282 amino acids | Increased with increased resistance to cis-platin |
| BC011770 | FAST kinase | 7q36.1 | Cytoplasmic 549 amino acids | Increased with increased resistance to cis-platin |
| AB057597 | TESK2 | 1p34.1 | Nuclear/Associated with Cytoskeleton | Increased with increased resistance to cis-platin |
| BC022087 | SRB1 CLA1 CD36L1 | 12q24.31 | Cell membrane | Increased with increased resistance to cis-platin |
| BC031890 | KIAA0082 | 6p21.1 | Unknown 836 amino acids | Increased with increased resistance to cis-platin |
| NM_006312 | NCOR2 | 12q24 | Nuclear 2517 amino acids | Decreased with increased resistance to cis-platin |
| BC032338 | MT1 | 16q13 | Mostly nuclear, can be secreted | Decreased with increased resistance to cis-platin |
| X98494 | MPP10 | 2p12-2p13.2 | Mostly cytoplasmic, can be secreted | Decreased with increased resistance to cis-platin |

The chromosomal locations that appear in bold type in Table 1 have been reported to be associated with ovarian cancer (Pejoic, 1995, *Ann. Med.* 27:73-78).

In one embodiment, an inhibitor of a cellular gene shown in Table 1 can be, for example, a small molecule inhibitor, an antibody, a nucleic acid such as an antisense nucleic acid, a short interfering RNA (siRNA) molecule, or a short hairpin RNA (shRNA) molecule. In addition, such inhibitors can be specifically designed using the methods described herein or using methods known in the art. For example, antibodies, particularly neutralizing antibodies and preferably monoclonal antibodies, to proteins encoded by a gene shown in Table 1 can be generated by conventional means as described, for example, in "Antibodies: A Laboratory Manual" by Harlow and Lane (Cold Spring Harbor Press, 1988), which is hereby incorporated by reference.

In a particular embodiment, an inhibitor of the invention is a siRNA that binds to mRNA encoding a target gene, wherein the target gene is a gene shown in Table 1.

In a preferred embodiment, certain inhibitors provided by the invention are species of short interfering RNA (siRNA). The term "short interfering RNA" or "siRNA" as used herein refers to a double stranded nucleic acid molecule capable of RNA interference or "RNAi", as disclosed, for example, in Bass, 2001, *Nature* 411: 428-429; Elbashir et al., 2001, *Nature* 411: 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914. As used herein, siRNA molecules need not be limited to those molecules containing only RNA, but further encompasses chemically modified nucleotides and non-nucleotides having RNAi capacity or activity.

Short interfering RNA mediated RNAi has been studied in a variety of systems. Fire et al. were the first to observe RNAi in *C. elegans* (1998, *Nature* 391:806). Wianny and Goetz described RNAi mediated by dsRNA in mouse embryos (1999, *Nature Cell Biol.* 2:70). Hammond et al. described RNAi in *Drosophila* cells transfected with dsRNA (2000, *Nature* 404:293). Elbashir et al. described RNAi induced by introduction of duplexes of synthetic 21-nucleotide RNAs in cultured mammalian cells including human embryonic kidney and HeLa cells (2001, *Nature* 411:494). These studies have shown that siRNA duplexes comprising 21 nucleotides are most active when containing two nucleotide 3'-overhangs. Furthermore, substitution of one or both siRNA strands with 2'-deoxy or 2'-O-methyl nucleotides abolishes RNAi activity, whereas substitution of 3'-terminal siRNA nucleotides with deoxynucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.* 20:6877). Other studies have indicated that a 5'-phosphate on the target-complementary strand of a siRNA duplex is required for siRNA activity and that ATP is utilized in cells to maintain the 5'-phosphate moiety on the siRNA (Nykanen et al., 2001, *Cell* 107:309). However siRNA molecules lacking a 5'-phosphate are active when introduced exogenously, suggesting that 5'-phosphorylation of siRNA constructs may occur in vivo. Chemically-modified siRNA can be directly injected into the blood stream for certain applications.

In certain embodiments, the invention provides expression vectors comprising a nucleic acid sequence encoding at least one siRNA molecule of the invention, in a manner that allows expression of the siRNA molecule. For example, the vector can contain sequence(s) encoding both strands of a siRNA molecule comprising a duplex. The vector can also contain sequence(s) encoding a single nucleic acid molecule that is self-complementary and thus forms a siRNA molecule. Non-limiting examples of such expression vectors are described in Paul et al., 2002, *Nature Biotechnology* 19:505; Miyagishi and Taira, 2002, *Nature Biotechnology* 19:497; Lee et al., 2002, *Nature Biotechnology* 19:500; and Novina et al., 2002, *Nature Medicine*, online publication Jun. 3, 2003.

In certain embodiments, siRNA molecules according to the invention can comprise a delivery vehicle, including inter alia liposomes, for administration to a subject, carriers and diluents and their salts, and can be present in pharmnaceutical compositions. Methods for the delivery of nucleic acid molecules are described, for example, in Akhtar et al., 1992, *Trends Cell Bio.* 2:139; Delivery Strategies for Antisense Oligonucleotide Therapeutics, ed. Akhtar, 1995, Maurer et al., 1999, *Mol. Membr. Biol.* 16:129-140; Hofland and Huang, 1999, *Handb. Exp. Pharmacol.*, 137:165-192; and Lee et al., 2000, *ACS Symp. Ser.* 752:184-192, all of which are incorporated herein by reference. Beigelman et al., U.S. Pat. No. 6,395,713 and Sullivan et al., PCT WO 94/02595, further describe general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722).

Alternatively, the nucleic acid/vehicle combination can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, *Clin. Cancer Res.* 5:2330-2337 and Barry et al., International PCT Publication No. WO 99/31262. Many examples in the art describe delivery methods of oligonucleotides by osmotic pump (see Chun et al., 1998, *Neuroscience Letters* 257:135-138, D'Aldin et al., 1998, *Mol. Brain Research* 55:151-164, Dryden et al., 1998, *J. Endocrinol.* 157:169-175, Ghirnikar et al., 1998, *Neuroscience Letters* 247:21-24) or direct infusion (Broaddus et al., 1997, *Neurosurg. Focus* 3, article 4). Other delivery routes include, but are not limited to oral delivery (such as in tablet or pill form) and/or intrathecal delivery (Gold, 1997, *Neuroscience* 76:1153-1158). More detailed descriptions of nucleic acid delivery and administration are provided in Sullivan et al., PCT WO 94/02595, Draper et al., PCT WO93/23569, Beigelman et al., PCT WO99/05094, and Klimuk et al., PCT WO99/04819, all of which are incorporated by reference herein.

Alternatively, certain siRNA molecules of the invention can be expressed within cells from eukaryotic promoters (see for example, Izant and Weintraub, 1985, *Science* 229:345; McGarry and Lindquist, 1986, *Proc. Natl. Acad. Sci., USA* 83:399; Scanlon et al., 1991, *Proc. Natl. Acad. Sci. USA* 88:10591-5; Kashani-Sabet et al., 1992, *Antisense Res. Dev.* 2:3-15; Dropulic et al., 1992, *J. Virol.* 66:1432-41; Weerasinghe et al., 1991, *J. Virol.* 65:5531-4; Ojwang et al., 1992, *Proc. Natl. Acad. Sci. USA* 89:10802-6; Chen et al., 1992, *Nucleic Acids Res.* 20:4581-9; Sarver et al., 1990, *Science* 247:1222-1225; Thompson et al., 1995, *Nucleic Acids Res.* 23:2259; Good et al., 1997, *Gene Therapy* 4:45; Miyagishi et al., 2001, *Nucleic Acids Research* 29:2502; and Kunkel and Pederson, 1989 *Nucleic Acids Research* 17:7371). Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595; Ohkawa et al., 1992, *Nucleic Acids Symp. Ser.* 27:15-6; Taira et al., 1991, *Nucleic Acids Res.* 19:5125-30; Ventura et al., 1993, *Nucleic Acids Res.* 21:3249-55; Chowrira et al., 1994, *J. Biol. Chem.* 269:25856).

In another aspect of the invention, RNA molecules of the present invention can be expressed from transcription units (see for example, Couture et al., 1996, *TIG* 12:510) inserted into DNA or RNA vectors. The recombinant vectors can be DNA plasmids or viral vectors. siRNA expressing viral vectors can be constructed based on, for example but not limited to, adeno-associated virus, retrovirus, adenovirus, lentivirus or alphavirus. In another embodiment, pol III based constructs are used to express nucleic acid molecules of the invention (see for example, Thompson, U.S. Pat. Nos. 5,902, 880 and 6,146,886). The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells ex-planted from a subject followed by reintroduction into the subject, or by any other means that would allow for introduction into the desired target cell (for a review, see Couture et al., 1996, *TIG.* 12:510).

In one embodiment, the invention provides an expression vector comprising a nucleic acid sequence encoding at least one siRNA molecule of the invention. The expression vector can encode one or both strands of a siRNA duplex, or a single self-complementary strand that self hybridizes into a siRNA duplex. The nucleic acid sequences encoding the siRNA molecules can be operably linked in a manner that allows expression of the siRNA molecule (see for example, Paul et al., 2002, *Nature Biotechnology* 19:505; Miyagishi and Taira, 2002, *Nature Biotechnology* 19:497; Lee et al., 2002, *Nature Biotechnology* 19:500; and Novina et al., 2002, *Nature Medicine, online publication Jun.* 3). The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

In another aspect, the invention provides an expression vector comprising: a) a transcription initiation region (e.g., eukaryotic pol I, II or III initiation region); b) a transcription termination region (e.g., eukaryotic pol I, II or III termination region); and c) a nucleic acid sequence encoding at least one of the siRNA molecules of the invention; wherein said sequence is operably linked to said initiation region and said termination region, in a manner that allows expression and/or delivery of the siRNA molecule. The vector can optionally include an open reading frame (ORF) for a protein operably linked on the 5' side or the 3'-side of the sequence encoding the siRNA of the invention; and/or an intron (intervening sequences).

Transcription of the siRNA molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA* 87:6743-7; Gao and Huang 1993, *Nucleic Acids Res.* 21:2867-72; Lieber et al., 1993, *Methods Enzymol.* 217:47-66; Zhou et al., 1990, *Mol. Cell. Biol.* 10:4529-37). Several investigators have demonstrated that nucleic acid molecules expressed from such promoters can function in mammalian cells (e.g. Kashani-Sabet et al., 1992, *Antisense Res. Dev.* 2:3-15; Ojwang et al., 1992, *Proc. Natl. Acad. Sci. USA* 89:10802-6; Chen et al., 1992, *Nucleic Acids Res.* 20:4581-9; Yu et al., 1993, *Proc. Natl. Acad. Sci. USA* 90:6340-4; L'Huillier et al., 1992, *EMBO J.* 11:4411-8; Lisziewicz et al., 1993, *Proc. Natl. Acad. Sci. U.S.A* 90:8000-4; Thompson et al., 1995, *Nucleic Acids Res.* 23:2259; Sullenger and Cech, 1993, *Science* 262:1566). More specifically, transcription units such as the ones derived from genes encoding U6 small nuclear (snRNA), transfer RNA (tRNA) and adenovirus VA RNA are useful in generating high concentrations of desired RNA molecules such as siRNA in cells (Thompson et al., 1995, *Nucleic Acids Res.* 23:2259; Couture et al., 1996, *TIG* 12:510; Noonberg et al., 1994, *Nucleic Acid Res.* 22:2830; Noonberg et al., U.S. Pat. No. 5,624,803; Good et al., 1997, *Gene Ther.* 4:45; Beigelman et al., International PCT Publication No. WO 96/18736. The above siRNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors; for a review see Couture et al., 1996, *TIG* 12:510).

In another embodiment, the invention provides an expression vector comprising a nucleic acid sequence encoding at least one of the siRNA molecules of the invention, in a manner that allows expression of that siRNA molecule. In a particular embodiment, the expression vector comprises: a) a transcription initiation region; b) a transcription termination region; and c) a nucleic acid sequence encoding at least one strand of the siRNA molecule; wherein the sequence is operably linked to the initiation region and the termination region, in a manner that allows expression and/or delivery of the siRNA molecule.

In another embodiment the expression vector comprises: a) a transcription initiation region; b) a transcription termination region; c) an open reading frame; and d) a nucleic acid sequence encoding at least one strand of a siRNA molecule, wherein the sequence is operably linked to the 3'-end of the open reading frame; and wherein the sequence is operably linked to the initiation region, the open reading frame and the termination region, in a manner that allows expression and/or delivery of the siRNA molecule.

In yet another embodiment the expression vector comprises: a) a transcription initiation region; b) a transcription termination region; c) an intron; and d) a nucleic acid sequence encoding at least one siRNA molecule; wherein the sequence is operably linked to the initiation region, the intron and the termination region, in a manner which allows expression and/or delivery of the nucleic acid molecule.

In another embodiment, the expression vector comprises: a) a transcription initiation region; b) a transcription termination region; c) an intron; d) an open reading frame; and e) a nucleic acid sequence encoding at least one strand of a siRNA molecule, wherein the sequence is operably linked to the 3'-end of the open reading frame; and wherein the sequence is operably linked to the initiation region, the intron, the open reading frame and the termination region, in a manner which allows expression and/or delivery of the siRNA molecule.

In one embodiment, growth of a tumor cell is inhibited by contacting the tumor cell with a siRNA that inhibits SPARC. Alternatively, the tumor cell can be contacted with the siRNA in the presence of a chemotherapeutic drug at a concentration to which the tumor cell is resistant. Examples of siRNA molecules that are SPARC inhibitors include, for example:

```
AATCC TGT CCA GGT GGA AGT A;      (SEQ ID NO: 1)

AAGCT CCA CCT GGA CTA CAT C;      (SEQ ID NO: 2)
and

AATGA CAA GTA CAT CGC CCT G.      (SEQ ID NO: 3)
```

In another embodiment, growth of a tumor cell is inhibited by contacting the tumor cell with a siRNA that inhibits MetAP2/p67. Alternatively, the tumor cell can be contacted with the siRNA in the presence of a chemotherapeutic drug at a concentration to which the tumor cell is resistant. Examples of siRNA molecules that are MetAP2/p67 inhibitors include, for example:

```
AAAGA TCA GCA TTG GAA GAT A;      (SEQ ID NO: 4)

AAGCA CAT CGA CAA GTT AGA A;      (SEQ ID NO: 5)
and

AAACA GTG CCG ATT GTG AAA G.      (SEQ ID NO: 6)
```

In another embodiment, growth of a tumor cell is inhibited by contacting the tumor cell with a siRNA that inhibits Calpain 2. Alternatively, the tumor cell can be contacted with the siRNA in the presence of a chemotherapeutic drug at a concentration to which the tumor cell is resistant. Examples of siRNA molecules that are Calpain 2 inhibitors include, for example:

```
AAGGC ATA CGC CAA GAT CAA C;    (SEQ ID NO: 7)

AAACT TCT TCC TGA CGA ATC G;    (SEQ ID NO: 8)
and

AAACG CTA TTC AAG ATA TTT A.    (SEQ ID NO: 9)
```

In another embodiment, growth of a tumor cell is inhibited by contacting the tumor cell with a siRNA that inhibits S100A10. Alternatively, the tumor cell can be contacted with the siRNA in the presence of a chemotherapeutic drug at a concentration to which the tumor cell is resistant. Examples of siRNA molecules that are S100A10 inhibitors include, for example,

```
AAATG GAA CAC GCC ATG GAA A;    (SEQ ID NO: 59)

AAATT CGC TGG GGA TAA AGG C;    (SEQ ID NO: 60)
and

AATAA TGA AGG ACC TGG ACC A.    (SEQ ID NO: 61)
```

The invention also provides methods for inhibiting, retarding or preventing growth of a tumor cell comprising the step of contacting the tumor cell with a combination of a chemotherapeutic agent or agents and at least one inhibitor of a cellular gene, wherein the cellular gene is a gene shown in Table 1. Preferably, the tumor cell is an ovarian cancer cell. Chemotherapeutic agents are known in the art, and include, for example, cis-platin, paclitaxel, carboplatin, etoposide, hexamethylamine, melphalan, and anthracyclines.

In one embodiment, the inhibitor of a cellular gene shown in Table 1 can be a small molecule inhibitor. As used herein, the term "small molecule" refers to a molecule that has a molecular weight of less then about 1500 g/Mol. A small molecule can be, for example, small organic molecules, peptides or peptide-like molecules. By way of example, a small molecule inhibitor suitable in methods of the invention can be a calpain inhibitor, such as PD 147631, (2S,3S)-trans-epoxysuccinyl-L-leucy-lamido-3-methylbutane ethyl ester (E-64-d), N-acetyl-leucyl-leucyl-norleucinal (ALLN), N-Acetyl-Leu-Leu-Met-al (ALLM or $C_{19}H_{35}N_3O_4S$), or MDL 18270; or a MetAP-2 inhibitor, such as TNP-470 (also known as AGM 1470 or $C_{19}H_{28}ClNO_6$), fumagillin ($C_{26}H_{34}O_7$), cis-fumagillin (see Kwon et al., 2000, *J. Antibiot.* 53:799-806), fumagalone (see Zhou et al., 2003, *J. Med. Chem.* 46:3452-3454), or ovalicin ($C_{16}H_{24}O_4$). See also Han et al., 2000, *Bioorganic & Medicinal Chem. Letters* 10:39-43.

In one embodiment, the inhibitor of a cellular gene shown in Table 1 can be an inhibitor as defined above. Any combination of inhibitors can be used, for example, multiple inhibitors of a particular gene shown in Table 1, a combination of inhibitors that each inhibit one or a plurality of specific genes, or an inhibitor that inhibits multiple genes shown in Table 1, or any combination thereof.

In a particular embodiment, the inventive methods comprise the step of contacting a tumor cell with a combination of an inhibitor of MetAP2 and a platinum-based chemotherapeutic agent. A chemotherapeutic agent is "platinum-based" if a major component of the agent is cis-platin or carboplatin, optionally in combination with taxol or cyclophosphamide. An inhibitor of MetAP2 can be, for example, fumagillin or a derivative of fumagillin, or a MetAP2 siRNA such as without limitation SEQ ID NO: 4, SEQ ID NO: 5, or SEQ ID NO: 6.

The invention also provides methods for predicting whether an ovarian cancer patient's tumor is resistant to chemotherapeutic treatment. In these embodiments, the methods comprise the steps of: (a) detecting an amount of one or a plurality of expressed genes or gene products encoded thereby in a biological sample taken from the patient, wherein the expressed gene(s) is shown in Table 1; (b) detecting an amount of the one or the plurality of expressed genes or gene products encoded thereby in a control sample, wherein the expressed gene is a gene shown in Table 1; and (c) comparing the amount of the expressed gene or gene product measured in step (a) with the amount of the expressed gene or gene product detected in step (b), wherein the patient is predicted to be resistant to chemotherapy if the amount detected in step (a) differs from the amount detected in step (b) by a factor of at least 20%. In one embodiment, the amount detected can be an amount of mRNA of a gene shown in Table 1 or an amount of protein encoded by a gene shown in Table 1. In another embodiment, the control sample is a biological sample from a responsive or normal subject, i.e. an individual who responds to therapy or one without a cancer, such as ovarian cancer. In a particular aspect, the biological sample is a tumor sample.

In one embodiment, the expressed gene in step (a) and step (b) is one or a plurality of S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082, and a patient's tumor is predicted to be resistant to chemotherapeutic treatment if the amount of the expressed gene in step (a) is at least about 20% higher than the amount of the expressed gene in step (b).

In a particular embodiment, the expressed gene in step (a) and step (b) is one or a plurality of Vinexin β, G-CSFR, KLK6, SPARC, HYA22, Calpain 2, SAPK/Erk1, SRB1, ADAR1, MRPL4, eIF5, eIF2Bε, WDR1, NM23D, zinc finger protein-262 MYM, RNPS1, S100A10, S100A11, or MetAP2, and patient's tumor is predicted to be resistant to chemotherapeutic treatment if the amount of the expressed gene in step (a) is at least about 20% higher than the amount of the expressed gene in step (b).

In another embodiment, the expressed gene in step (a) and step (b) is one or a plurality of HMT1, NAIP, eEF1ε, RAB22A, NCOR2, MPP10, or MT1, and a patient's tumor is predicted to be resistant to chemotherapeutic treatment if the amount of the expressed gene in step (a) is at least about 20%, preferably 50%, lower than the amount of the expressed gene in step (b).

In a particular embodiment, the expressed gene in step (a) and step (b) is one or a plurality of HMT1, eEF1ε, NAIP, RAB22A or MT1, and patient's tumor is predicted to be resistant to chemotherapeutic treatment if the amount of the expressed gene in step (a) is at least about 20%, preferably 50% lower than the amount of the expressed gene in step (b).

Thus as disclosed herein the invention provides one or a plurality of gene expression or gene product activity patterns comprising a plurality of said genes that are differentially (i.e., at greater or lesser amounts) expressed or wherein the protein products encoded by said genes have differential activity in chemotherapeutic drug resistant ovarian tumor cells than in normal (i.e., non-tumor or chemo-sensitive) cells. Said patterns of differential gene expression or protein product activity are used according to the methods of the invention to detect chemotherapeutic drug-resistant cells in a biological, most preferably a tumor, sample, and are thus useful in predicting drug resistance in a tumor from an individual prior to a clinician initiating a fruitless treatment course associated with significant morbidity and mortality.

It will be understood by those of ordinary skill in the art that in the practice of the methods of the invention, patient tumor samples can be evaluated for expression of one or a plurality of the genes identified herein. Each of the plurality of genes identified herein is expected to show the differential gene expression detected using the instantly-disclosed methods in a percentage, most preferably a high percentage, of individual tumors isolated from specific ovarian cancer patients. It is also expected that the confidence in the results obtained using the predictive methods of the invention will increase with increasing numbers of said genes assayed that display the differential gene expression disclosed herein.

In one embodiment, the methods of the invention can be used to screen human patients in need of treatment with chemotherapy prior to actually treating said patients with a chemotherapeutic agent. Thus, the inventive methods can be used to screen patients to enable a care provider to determine whether or not treatment of said patient with a particular chemotherapeutic agent will be ineffective. A patient who is predicted to be non-resistant to chemotherapy based on methods of the invention is a candidate for treatment with chemotherapy and/or an inhibitor of a gene that is shown in Table 1. A patient who is predicted to be resistant to chemotherapy based on a method of the invention can be a candidate, inter alia for surgery and/or a chemotherapeutic treatment in conjunction with an inhibitor of a gene that is shown in Table 1, or another treatment method.

In the practice of the methods of the invention, gene expression is detected by detecting the amount of mRNA encoding any of the genes identified herein expressed in a biological sample, for example by hybridization assays such as Northern blots or dot blots, or by amplification methods such as polymerase chain reaction (PCR), more preferably coupled with reverse transcription of the mRNA to cDNA (RT-PCR), and even more preferably using methods known in the art for quantitative real-time RT-PCR, as described in more detail herein. Other approaches include detecting the amount of a protein product of said gene or genes, in non-limiting example by assaying a biological sample using protein-specific antisera, more preferably antibodies and even more preferably monoclonal antibodies specific for any particular gene as identified herein. Protein expression levels can also be determined by assaying a biological sample for an enzymatic or antigenic activity of the protein product. The invention also provides gene or antibody arrays for detecting expression of genes over- or under-expressed in chemotherapeutic drug resistant tumors, particularly ovarian and colon tumors, wherein the arrangement of the nucleic acid probes or antibodies in the array produce a recognizable, preferably machine-readable pattern when a tumor sample is chemotherapeutic drug-resistant, and/or a different, recognizable pattern when the tumor sample is chemotherapeutic drug-sensitive.

For example, according to the methods of the invention an amount of MetAP2 that is expressed in a biological sample from a patient is determined and compared with an amount of MetAP2 expressed in either a person who has ovarian cancer and responded to chemotherapy or a person who has ovarian cancer and did not respond to chemotherapy. As used herein, a person has "responded to" chemotherapy if a chemotherapeutic therapy had the effect of reducing tumor size or stopping tumor growth. Moreover, the term "responsive patient" is intended to mean one who after surgical resection is treated with chemotherapy and remains without clinical signs of disease for at least 6 months. If the amount of MetAP2 in the patient is equal to or less than the amount of MetAP2 expressed in a person who has ovarian cancer and who responded to chemotherapy, the patient is predicted to be responsive to certain chemotherapeutic agents (e.g. platinum-based compounds). If the amount of MetAP2 in the patient is greater than the amount of MetAP2 expressed in a person who has ovarian cancer and who responded to chemotherapy, the patient is predicted to be resistant to chemotherapeutic agents. Likewise, if the amount of MetAP2 in the patient is greater than the amount of MetAP2 expressed in a person who has cancer but did not respond to chemotherapy, the patient is predicted to be resistant to chemotherapeutic agents.

As shown in Table 1 and the Examples below, increased expression of MetAP2 in ovarian cancer is associated with increased resistance to cis-platin, a platinum-based chemotherapeutic agent. Consequently, in one embodiment, methods of the invention can predict that a patient's tumor will be resistant to platinum-based chemotherapy when the measured amount of MetAP2 expressed in the biological sample from the cancer patient is greater than the predetermined amount detected in a responsive individual. In another embodiment, methods of the invention can predict that a patient's tumor will be resistant to platinum-based chemotherapy when the measured amount of MetAP2 expressed in the biological sample from the cancer patient is equal to the predetermined amount detected in the responsive individual but where the expression of one or a plurality of genes, where the genes are: S100A10, S100A11, Calpain 2, SPARC, KLK6, ARA9, Calponin 2, RNPS1, eIF5, eIF2Bϵ, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082, is increased over expression in the responsive patient, and/or expression of one or a plurality of the HMT1, NAIP, eEF1ϵ, RAB22A, NCOR2, MT1 or MPP10 genes is decreased in comparison with expression in the responsive patient The invention further provides methods for monitoring disease progression in an ovarian cancer patient, particularly an ovarian cancer patient being treated with a chemotherapeutic treatment, comprising the steps of: (a) detecting an amount of one or a plurality of expressed genes or gene products encoded thereby in a biological sample taken from the patient, wherein the expressed gene is S100A10, S100A11, Calpain 2, SPARC, MetAP2, KLK6, ARA9, Calponin 2, RNPS1, eIF5, eIF2Bϵ, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, KIAA0082, MPP10, HMT1, NAIP, eEF1ϵ, RAB22A, NCOR2 or MT1; (b) repeating step (a) using a subsequently-collected biological sample obtained from the patient; and (c) comparing the amount of expressed gene or gene product detected in step (a) with the amount of expressed gene or gene product detected in step (b), wherein disease progression is monitored by detecting differences in the amount of expressed gene or gene products in the subsequently-collected biological sample compared with the biological sample taken in step (a). In a particular aspect, the biological sample is a tumor sample.

As set forth herein, disease progression is detected when the expressed gene(s) in steps (a) and (b) is S100A10, S100A11, Calpain 2, SPARC, MetAP2, KLK6, ARA9, Calponin 2, RNPS1, eIF5, eIF2Bϵ, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1 or KIAA0082, and the amount of the expressed gene or gene product detected in step (b) is greater than the amount of the expressed gene or gene product in step (a). In certain embodiments, the patient undergoes chemotherapeutic or other treatment during the period between detecting the amount of gene expression in step (a) and the amount detected in step (b).

As set forth herein, disease progression is detected when the expressed gene(s) in steps (a) and (b) is HMT1, NAIP, eEF1ε, RAB22A, NCOR2, MT1 or MPP10, and the amount of the expressed gene or gene product detected in step (b) is less than the amount of the expressed gene or gene product in step (a).

In certain embodiments, the patient undergoes chemotherapeutic or other treatment during the period between detecting the amount of gene expression in step (a) and the amount detected in step (b). In certain embodiments, the amount detected can be an amount of mRNA of a gene shown in Table 1 or an amount of protein encoded by a gene shown in Table 1.

Methods according to the invention for monitoring progression of ovarian cancer in a patient can be used, for example, to determine if a patient is responding positively or negatively to a certain treatment regime, such as a chemotherapeutic treatment regime.

For example, a patient is responding negatively where expression of S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082 is the same or greater in a biological sample taken from a patient at a time after the patient started a certain treatment regime compared with the amount of the expressed gene in a biological sample taken before or at the time the treatment regime was started. In another example, a patient is responding negatively where the expression of HMT1, NAIP, eEF1ε, RAB22A, NCOR2, MT1 or MPP10 is the same or less in a biological sample taken from a patient some time after the patient started a certain treatment regime compared with the amount of the expressed gene in a biological sample taken before or at the time the treatment regime was started. In such cases, a care provider can determine that the treatment regime is not effective.

Alternatively, a patient is responding positively, and no change in treatment is needed, where the expression of S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082, is less in a biological sample taken from a patient some time after the patient started a certain treatment regime compared with the amount of the expressed gene in a biological sample taken before or at the time the treatment regime was started. Furthermore, a patient is responding positively where the expression of HMT1, NAIP, eEF1ε, RAB22A, NCOR2, MT1 or MPP10 is greater in a biological sample taken from a patient some time after the patient started a certain treatment regime compared with the amount of the expressed gene in a biological sample taken before or at the time the treatment regime was started.

In addition, the invention provides methods for monitoring the effectiveness of a pharmaceutical composition as an agent for treating cancer in a patient comprising the steps of: (a) detecting an amount of one or a plurality of expressed genes or gene products encoded thereby in a biological sample taken from a patient, wherein the expressed gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) administering an amount of a pharmaceutical composition to the patient; (c) repeating step (a) using a subsequently-collected biological sample obtained from the patient; and (d) comparing the amount of expressed gene or gene product detected in step (a) with the amount of expressed gene or gene product detected in step (c), wherein the effectiveness of the pharmaceutical composition is monitored by detecting changes in the amount of expressed gene or gene products in the subsequently-collected biological sample compared with the biological sample taken in step (a). If gene expression is greater than or equal to the biological sample collected after treatment with the pharmaceutical composition than in the biological sample collected prior to treatment with the pharmaceutical composition and tumor growth has not been slowed, retarded or inhibited during treatment with the pharmaceutical composition, the pharmaceutical composition can be considered ineffective for treating the patient's cancer. For example, if an amount of S100A10 mRNA is higher in samples obtained after a patient has been treated with a pharmaceutical composition, the patient is predicted to be resistant to further treatment with that pharmaceutical composition. Thus, the pharmaceutical composition is considered ineffective against that patient's cancer. In a particular aspect, the biological sample is a tumor sample.

The invention further provides methods for monitoring the effectiveness of a pharmaceutical composition as an agent for treating cancer in a patient comprising the steps of: (a) detecting an amount of one or a plurality of expressed genes or gene products encoded thereby in a biological sample taken from a patient, wherein the expressed gene is HMT1, NAIP, eEF1ε, RAB22A, NCOR2, MT1 or MPP10; (b) administering an amount of a pharmaceutical composition to the patient; (c) repeating step (a) using a subsequently-collected biological sample obtained from the patient; and (d) comparing the amount of expressed gene or gene product detected in step (a) with the amount of expressed gene or gene product detected in step (c), wherein the effectiveness of the pharmaceutical composition is monitored by detecting changes in the amount of expressed gene or gene products in the biological sample collected after treatment with the pharmaceutical composition compared with the biological sample taken in step (a), i.e. collected prior to treatment with the pharmaceutical composition. If gene expression of one or a plurality of said genes is lower than or equal to in the subsequently-collected biological sample (i.e., collected after treatment with the pharmaceutical composition) than in the previously-collected biological sample (i.e., collected prior to treatment with the pharmaceutical composition), and tumor growth has not been slowed, retarded or inhibited during treatment with the pharmaceutical composition, the pharmaceutical composition can be considered ineffective for treating the patient's cancer, and the patient is predicted to be resistant to further treatments with that pharmaceutical composition. Thus, the pharmaceutical composition is considered ineffective against that patient's cancer. In a particular aspect, the biological sample is a tumor sample.

As used herein, a "pharmaceutical composition" can be any formulation comprising a compound (e.g. a protein, peptide, peptidomimetic, non-peptide organic molecule, an inorganic small molecule, or nucleic acid molecule) that is used to treat or tested for the ability to treat a cancer, such as colon or ovarian cancer.

The invention also provides methods for identifying compounds that inhibit growth of a tumor cell, particularly a chemoresistant tumor cell, and most particularly a chemoresistant ovarian cancer cell. In these embodiments, the method comprises the steps of: (a) contacting a cell that expresses one or a plurality of genes that are overexpressed in chemoresistant ovarian cancer cells with a test compound, wherein the gene is S100A10, S100A11, Calpain 2, SPARC, MetAP2, KLK6, ARA9, Calponin 2, RNPS1, eIF5, eIF2Bε, HSF2, WDR1, Fused toes, NM23D, ADAR1, Grancalcin, NBR1, SAPK/Erk1, zinc finger protein-262 MYM, HYA22, MRPL4, Vinexin β, G-CSFR, IGFBP-7, FAST kinase, TESK2, SRB1, or KIAA0082; (b) detecting expression of the gene in the presence and absence of the test compound; and (c) comparing expression of the gene in the presence of the compound with expression of the gene in the absence of the test compound, wherein a compound is identified as a compound that inhibits chemoresistant tumor cell growth if expression of the gene in the presence of the test compound is reduced relative to expression of the gene in the absence of the test compound. In a particular aspect, the biological sample is a tumor sample. In certain embodiments, the compound can inhibit growth of the tumor cell in the presence of a chemotherapeutic drug.

In addition, the invention provides methods of identifying a compound that inhibits growth of a tumor cell, particularly a chemoresistant tumor cell, and most particularly a chemoresistant ovarian cancer cell comprising the steps of: (a) contacting with a test compound a cell that expresses one or a plurality of genes that are expressed at a lower than normal level in chemoresistant ovarian cancer cells, wherein the gene is HMT1, NAIP, eEF1ε, RAB22A, NCOR2, MT1 or MPP10; (b) detecting expression of the gene in the presence and absence of the test compound; and (c) comparing expression of the gene in the presence and absence of the test compound, wherein a compound is identified as a compound that inhibits chemoresistant tumor cell growth if expression of the gene in the presence of the test compound is increased relative to expression of the gene in the absence of the test compound. In one embodiment, the compound can inhibit growth of the tumor cell in the presence of a chemotherapeutic drug.

The following examples, including the experiments conducted and results achieved are provided for illustrative purposes only and are not to be construed as limiting the invention.

EXAMPLES

Example 1

MTT Cell Proliferation Assays

Five ovarian cancer cell lines (OVCA 429, OVCA 433, OVCA 432, HEY and HEYA8) were ranked according to their levels of sensitivity to cis-platin using standard MTT cell proliferation assays.

Cells were grown in Minimal Eagle's Media (MEMα, obtained from Invitrogen Corp., Carlsbad, Calif.), 5% fetal bovine serum (FBS, heat inactivated), 1% antibiotic/antimycotic mixture (Invitrogen). The MTT stock solution (5 mg/mL; CALBIOCHEM, San Diego, Calif.) was prepared by dissolving dye in HBSS (Hank's Balanced Salt Solution), filtering said mixture and stored in 1 ml aliquots at −20° C. One ml of MTT stock was used for every 9 ml of media (total volume is 10 ml). Plates were covered with an opaque covering to protect the cells from light.

Each cell line was treated with 5, 25, 50, 100 and 200 μM cis-platin for 4, 8 and 24 hours. MTT assays were performed 96 hours after cis-platin treatment on 96 well plates. Media was removed from the cells and 200 μl of fresh MTT media was added to the cells and also to blank wells to serve as controls. Cells were incubated under normal cell culture conditions for 3-4 hours. Cells were then checked for formation of Formazan crystals, an indication of metabolic activity. Media was removed and 200 μl of 2-propanol were added to wells and control wells. After all the crystals were dissolved evenly, the cells were incubated for 20 minutes at room temperature in the dark. Results were read on a microplate reader at 570 nm.

Figure 39:
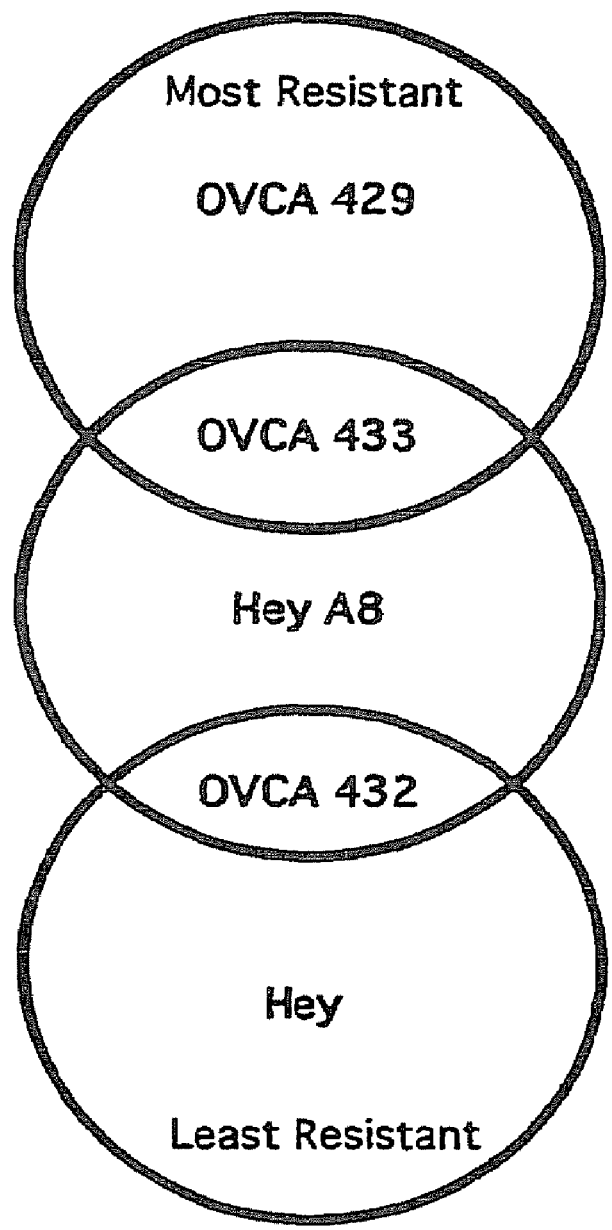
FIG. 39 shows the rankings of five ovarian cancer cell lines according to their level of sensitivity to cis-platin based on the results of MTT assays.

FIG. 39 (upper panel) shows the MTT assay results for 5 ovarian cancer cell lines used in these studies after 4 hours of exposure to cis-platin at various concentrations. After taking into account the performance of each cell line over the entire range of cis-platin concentrations and treatment times used, the cells were ranked in decreasing level of resistance as OVCA 429<OVCA 433<HEY A8<OVCA 432<HEY (lower panel).

MTT assays involving the exposure of cells to either a siRNA or drug inhibitor for a particular gene were conducted in essentially as described above. The cells were pre-treated with siRNAs for 48 hours prior to treatment with 0, 3.12, 6.25, 12.5, 25, 50, 100 and 200 μM cis-platin for 24 hours. For combination drug treatment experiments (fumagillin or ALLN) the cells were exposed to a combination treatment of increasing concentrations of the drug being tested and 0, 3.12, 6.25, 12.5, 25, 50, 100 and 200 μM cis-platin for 24 hours.

Example 2 cDNA Micro Array, Northern Blot, and Quantitative Real-Time PCR Analysis

The cell lines characterized in Example 1 were used to perform micro-array analysis. Cell pellets were collected from each cell line and RNA was isolated from the cells by dissolving the pellets in 1 ml of TRI-Reagent (obtained from Molecular Research Center, Inc, Cincinnati, Ohio) or Trizol (Invitrogen). The samples were then allowed to sit for 5 minutes. Phase separation was accomplished by adding 100 μl of 1-bromo-3-chloropropane (BCP) to the sample. After shaking for 15 seconds, samples were incubated at room temperature for 15 minutes and then centrifuged for 16 minutes at 13,000 RCF at 4-25° C. The supernatant was removed by pipette and placed into a new microfuge tube. RNA was then precipitated by mixing the supernatant with 500 μl of fresh isopropanol, incubated at room temperature for 10 minutes, and centrifuged for 9 minutes at 13,000 RCF at 4-25° C. The supernatant was then removed from the tube and the pellet was washed by adding 1 ml of 75% ethanol to the tube, vortexing, and then centrifuging for 6 minutes at 13,000 RCF at 4-25° C. The liquid was removed and the pellet was air-dried for about 8 minutes. The pellet was then dissolved in RNase-free water and placed on ice for immediate use or stored at −80° C.

Micro-arrays (obtained from Research Genetics Inc.) containing over 5000 sequence-verified cDNA clones were used to interrogate gene expression in these cells; all micro-array assays were conducted according to the manufacturer's instructions. Each clone was known to be expressed in ovarian tissue. Gene expression in the most resistant cell line (OVCA 429) was used as a standard to which gene expression in the other cell lines was compared. Analysis of the data revealed that OVCA 429 expressed 196 genes at increased levels and 83 genes expressed at decreased levels compared to the more sensitive cell lines.

Genes were selected for further analysis only if they satisfied the following criteria: an at least 2-fold difference in expression compared to the standard as detected on duplicate membranes; differential expression detected in 3 out of 4 cell lines compared to the standard (OVCA 429); and expression levels consistent with each cell line's sensitivity to cis-platin. Overexpressed genes were most highly expressed in OVCA 429 cells and expression gradually tapered off until the lowest level of expression was reached in the least resistant cell line HEY (and vice versa for genes expressed at lower levels in OVCA 429 cells).

Northern blot analysis and quantitative real-time PCR analysis of the genes that were differentially expressed (higher or lower levels) in the most resistant cell line (OVCA 429) when compared to the other cell lines were used to validate the microarray data and identify genes of interest for further analysis. The identified genes are listed in Table 2, which shows the gene name, a summary of the expression pattern in the cell lines, and the Figure that presents the results of the expression analyses.

TABLE 2

| GenBank Accession # | GeneCard cDNA id # | Names | Expression pattern as validated in cell lines | FIG. |
|---|---|---|---|---|
| BC015973 | 756595 | S100A10 p11 CLP11 Calpactin 1 light chain 42C | Increased with increased resistance to cis-platin | 1 |
| BC001410 | 810612 | S100A11 S100C Calgizzarin | Increased with increased resistance to cis-platin | 2 |
| AF261089 | 549728 | Calpain 2 CANPL2 mCANP | Increased with increased resistance to cis-platin | 6 |
| BC004974 | 250654 | SPARC Osteonectin BM-40 | Increased with increased resistance to cis-platin | 4 |
| BC013782 | 39093 | MetAP2 p67eIF2 MNPEP | Increased with increased resistance to cis-platin | 8 |
| BC015525 | 809784 | KLK6 Zyme Neurosin Protease M | Increases with increased resistance to cis-platin | 17 |
| AF222689 | 246120 | HMT1 HMT2 ANM1 HCP1 | Decreased with increased resistance to cis-platin | 18 |
| U31913 | 814731 | ARA9 XAP2 | Increased with increased resistance to cis-platin | 19 |

TABLE 2-continued

| GenBank Accession # | GeneCard cDNA id # | Names | Expression pattern as validated in cell lines | FIG. |
|---|---|---|---|---|
| D83735 | 713886 | Calponin 2 | Increased with increased resistance to cis-platin | 20 |
| U19251 | 1046522 | NAIP | Decreased with increased resistance to cis-platin | 21 |
| BC005291 | 306921 | eEF1ϵ P18 | Decreased with increased resistance to cis-platin | 13 |
| AF015608 | 897594 | RNPS1 | Increased with increased resistance to cis-platin | 22 |
| U49436 | 884867 | eIF5 Eif5A | Increased with increased resistance to cis-platin | 10 |
| BC013590 | 1630998 | Eif2Bϵ | Increased with increased resistance to cis-platin | 12 |
| M65217 | 669443 | HSF2 HSTF2 | Increased with increased resistance to cis-platin | 23 |
| AB010427 | 714196 | WDR1 NORI-1 | Increased with increased resistance to cis-platin | 24 |
| BC001134 | 321247 | Fused-toes (Ft1) | Increased with increased resistance to cis-platin | 25 |
| BC004880 | 203003 | NM23D nm23-H4 | Increased with increased resistance to cis-platin | 26 |
| U10439 | 950367 | ADAR1 | Increased with increased resistance to cis-platin | 27 |
| BC005214 | 34140 | Grancalcin | Increased with increased resistance to cis-platin | 7 |
| BC009808 | 882511; M17S2 | NBR1 | Increased with increased resistance to cis-platin | 28 |
| L36870 | 726147 | SAPK/Erk1 JNKK1 MEK4 MKK4 MAPKK4 | Increased with increased resistance to cis-platin | 14 |

TABLE 2-continued

| GenBank Accession # | GeneCard cDNA id # | Names | Expression pattern as validated in cell lines | FIG. |
|---|---|---|---|---|
| AB007885 | 427980 | Zinc finger protein-262 MYM | Increased with increased resistance to cis-platin | 29 |
| D88153 | 123980 | HYA22 | Increased with increased resistance to cis-platin | 31 |
| AB049635 | 824568 | MRPL4 CGI-28 | Increased with increased resistance to cis-platin | 30 |
| AF037261 | 1636620 | Vinexin β | Increased with increased resistance to cis-platin | 32 |
| M59818 | 809639 | G-CSFR | Increased with increased resistance to cis-platin | 33 |
| BC015710 | 838636 | RAB22A | Decreased with increased resistance to cis-platin | 36 |
| BC017201 | 68605 | IGFBP-7 MAC25 FSTL2 | Increased with increased resistance to cis-platin | 35 |
| BC011770 | 345077 | FAST kinase | Increased with increased resistance to cis-platin | 16 |
| AB057597 | 845441 | TESK2 | Increased with increased resistance to cis-platin | 15 |
| BC022087 | 756687 | SRB1 CLA1 CD36L1 | Increased with increased resistance to cis-platin | 34 |
| BC031890 | 825293 | KIAA0082 | Increased with increased resistance to cis-platin | 37 |
| NM_006312 | 743230; NCOR2 | NCOR2 | Decreased with increased resistance to cis-platin | 38 |
| BC032338 | 297392 | MT1 | Decreased with increased resistance to cis-platin | 51 |
| X98494 | 825214 | MPP10 | Decreased with increased resistance to cis-platin | 52 |

*GeneCard is a registered trademark of the Weizmann Institute of Science in Rehovot, Israel and numerical assignments can be changed at any time.

Northern Blot Analysis

In order to confirm expression patterns identified by microarray analysis, Northern blot analysis was performed using the NORTHERNMAX Protocol (Ambion Corp., Austin, Tex.) and DNA probes were labeled using STRIP-EZ DNA labeling kits (Ambion) according to the manufacturer's instructions.

Quantitative Real-Time PCR cDNA was synthesized by mixing together 1pg total cellular RNA isolated from ovarian cancer cell lines, 1 µl oligo dT, and water to a final volume of 12 µl, incubating this mixture at 70° C. for ten minutes, and then adding to the mixture 5 µl 2× Reaction Mix, 2 µl DTT, and 1 µl of SUPERSCRIPT II Enzyme (Invitrogen). The reaction mixture was then incubated at 42° C. for 60 minutes. cDNA dilutions from 1:4 to 1:256 were prepared. Master mixes were prepared with a final volume of 50 µl/well using the Qiagen QUANTITECT SYBR Green PCR Handbook (Qiagen Corp., Valencia Calif.). For every well of a plate that was used, 25 µl 2× QUANTITECT SYBR Green PCR Master Mix (Qiagen), 0.3 µm of forward primer, 0.3 µm of reverse primer, and RNase free water were added to a final volume of 45 µl.

The master mixes for each gene were thoroughly mixed and appropriate volumes were dispensed into PCR tubes or plates as follows: no template (control)=45 µl master gene mix+5 µl $H_2O$; buffer blank=25 µl $H_2O$+25 µl SYBR mix; and test samples=45 µl master gene mix+5 µl cDNA (diluted as above).

Sequence detection was determined using the ABI Prism 7700 (Applied Biosystems, Inc., Foster City, Calif.) sequence detection system or the M J Research (Waltham, Mass.) Opticon II system as follows: PCR initial activation step was carried out for 15 minutes at 95° C.; samples were denatured for 15 seconds at 94° C., annealed for 30 seconds at 53° C. (55° C. when the Opticon II system was used), and extended for 30 seconds at 72° C. (data was acquired during this step); the PCR reaction was repeated for 50 cycles. A melting curve analysis was prepared by adding on the following steps: 15 seconds at 95° C., 20 seconds at 60° C., and 20 seconds at 95° C.

In addition, RNA was prepared from tissue samples obtained from chemosensitive (i.e. responsive) and chemoresistant (i.e. non-responsive) ovarian cancer patients who had been treated with platinum-based chemotherapeutic agents. RNA was isolated by homogenizing 50-100 mg tissue samples in 1 ml TRI-Reagent or Trizol until the tissues were liquidized. The samples were then allowed to sit for 5 minutes. Phase separation was accomplished by adding 100 µl of BCP to the sample. After shaking for 15 seconds, samples were incubated at room temperature for 15 minutes and then centrifuged for 9 minutes at 13,000×g (relative centrifugal force, RCF) at 4-25° C. The supernatant was removed by pipette and placed into a new microfuge tube. RNA was then precipitated by mixing the supernatant with 500 µl of fresh isopropanol, incubated at room temperature for 20 minutes, and centrifuged for 9 minutes at 13,000 RCF at 4-25° C. The supernatant was then removed from the tube and the pellet was washed by adding 1 ml of 75% ethanol to the tube, vortexing, and then centrifuging for 6 minutes at 13,000 RCF at 4-25° C. The liquid was removed and the pellet was air-dried for about 8 minutes. The pellet was then dissolved in RNase-free water and placed on ice for immediate use or stored at −80° C.

Quantitative Real-Time PCR using primers for the genes shown in Table 3 was performed to detect changes in gene expression between the chemosensitive and chemoresistant patients. Expression of 18S RNA was used to correct the values of the expressed genes. The results are shown in Table 3 below. The results confirm the observations from the experiments conducted with RNA from cell lines.

TABLE 3

| Gene Name | GenBank Accession # | Fold Expression in Chemosensitive Patients | Fold Expression in Chemoresistant Patients | Fold Difference |
|---|---|---|---|---|
| Vinexin β | AF037261 | 1.4 | 2.8 | 2.0 |
| G-CSFR | M59818 | 1.7 | 2.6 | 1.5 |
| KLK6 | BC015525 | 0.3 | 3.3 | 11.0 |
| SPARC | BC004974 | 3.6 | 6.0 | 1.7 |
| HYA22 | D88153 | 1.75 | 2.4 | 1.4 |
| MRPL4 | AB049635 | 0.3 | 0.8 | 2.7 |
| eIF5 | U49436 | 0.8 | 1.3 | 1.6 |
| RAB22A | BC015710 | 0.15 | 0.075 | 2.0* |
| MT1 | BC032338 | 0.9 | 0.6 | 1.5* |
| MYM | AB007885 | 0.6 | 1.5 | 2.5 |
| RNPS1 | AF015608 | 0.7 | 1.4 | 2.0 |
| S100A11 | BC001410 | 1.0 | 2.0 | 2.0 |
| MetAP2 | BC013782 | 0.175 | 0.21 | 1.2 |
| S100A10 | BC015973 | 0.15 | 0.25 | 1.7 |
| SAPK | L36870 | 0.40 | 0.95 | 2.4 |
| Calpain 2 | AF261089 | 0.12 | 0.19 | 1.6 |
| NM23D | BC004880 | 0.70 | 1.3 | 1.9 |
| NIAP | U19251 | 4 | 2 | 2.0* |
| SRB1 | BC022087 | 0.08 | 0.13 | 1.6 |
| WDR1 | AB010427 | 1.5 | 5 | 3.3 |
| HMT1 | AF222689 | 0.19 | 0.05 | 3.8* |
| eEF1, | BC005291 | 0.65 | 0.15 | 4.3* |
| eIF2B, | BC013590 | 0.40 | 0.75 | 1.9 |
| ADAR1 | U10439 | 0.65 | 0.8 | 1.2 |

*this difference reflects a decrease in gene expression in the chemoresistant patients The following primer sequences were used to validate gene expression using Real-Time PCR:

250654 (this gene was initially validated with a specific molecular beacon probe, however, subsequent studies were carried out with SYBR green)

Molecular beacon validation:

```
                                        (SEQ ID NO: 13)
Beacon: FAM-CGCGTATGAACTGGGCTTATGTGACGCG-DABCYL
                                        (SEQ ID NO: 14)
Flanking forward primer: CTGGGCTCTGCCTTAAACAC
                                        (SEQ ID NO: 15)
Flanking reverse primer: GCTCCCAAAAGTTTGAACCA
                                        (SEQ ID NO: 16)
Internal forward primer: TTGCCTGAGGCTGTAACTGA
                                        (SEQ ID NO: 62)
Internal reverse primer: GCTCCCAAAAGTTTGAACCA For SYBR green:

(SEQ ID NO: 17)
forward: CCA CTT CTT TGC CAC AAA GT
                                        (SEQ ID NO: 18)
reverse: GAA TTC GGT CAG CTC AGA GT 810612
(this gene was validated with a specific molecular
beacon probe)
                                        (SEQ ID NO: 19)
Beacon: FAM-CGCCTGGGTGGGTTTGAAGGAGGCG-DABCYL
                                        (SEQ ID NO: 20)
Flanking forward primer: ATCGAGTCCCTGATTGCTGT
                                        (SEQ ID NO: 21)
Flanking reverse primer: GCCTGCATGAGGTGGTTAGT
                                        (SEQ ID NO: 22)
Internal forward primer: CTTGCCATGACTCCTTCCTC
                                        (SEQ ID NO: 63)
Internal reverse primer: GCCTGCATGAGGTGGTTAGT 39093
                                        (SEQ ID NO: 23)
forward: GCA GAA GCA CAT CGA CAA CT
                                        (SEQ ID NO: 24)
reverse: CCC TGC ATT TAA TCC ATT CTC 882511
                                        (SEQ ID NO: 25)
forward: TAA CCA CGT CCT CCT CAA GT
                                        (SEQ ID NO: 26)
reverse: CCT TTA AGA AAG TTC TTA TCA AC 950367
                                        (SEQ ID NO: 27)
forward: GCA CAG CGG AGT GGT AAG A
                                        (SEQ ID NO: 28)
reverse: CAG AGG AGT CAG ACA CAT TG 34140
                                        (SEQ ID NO: 29)
forward: GTA TAC TTA CTT CAG TGC TGT T
                                        (SEQ ID NO: 30)
reverse: CAT TCT TGC TAT AAC GTT AAA CA 726147
                                        (SEQ ID NO: 31)
forward: CTC TGT GAC TTC GGC ATC A
                                        (SEQ ID NO: 32)
reverse: CAG ACA TCA GAG CGG ACA T 427980
                                        (SEQ ID NO: 33)
forward: AAC AAC TGG GTT CAG TGG AAA
                                        (SEQ ID NO: 34)
reverse: GAG AGT CCA TGG TCT TGA GT 123980
                                        (SEQ ID NO: 35)
forward: AGC CAC GAG CTA AGT ACC TT
                                        (SEQ ID NO: 36)
reverse: CAT GGA TTT GAA CGG GAA GAA
```

```
824568
                                                  (SEQ ID NO: 37)
forward: GTG TGT GGA GGT GGA TGT TA
                                                  (SEQ ID NO: 38)
reverse: AGG AGA GGA TTA GAG AGA AGT 1636620
                                                  (SEQ ID NO: 39)
forward: GGA AGG AGT TTG TGG AGG AA
                                                  (SEQ ID NO: 40)
reverse: GTG GAG GAG GAG GTG AAT G 809639
                                                  (SEQ ID NO: 41)
forward: ATG GAA GGT TAT GTG GTT TGT T
                                                  (SEQ ID NO: 42)
reverse: GAG GTG GTG GGG TTG TGA A 756687
                                                  (SEQ ID NO: 43)
forward: GAT GGA TGA AGG TAA TGT AGA A
                                                  (SEQ ID NO: 44)
reverse: AGG GGG AGA AGG CTT CGT T 845441
                                                  (SEQ ID NO: 45)
forward: GGT GAG GTT GTG GGA GAT G
                                                  (SEQ ID NO: 46)
reverse: TGG AGG GGG AAA TTG TGT GT 68605
                                                  (SEQ ID NO: 47)
forward: GAA GAG GGG GAA GGG TAA A
                                                  (SEQ ID NO: 48)
reverse 1: GAG GGG GTG GGG TAG GT
                                                  (SEQ ID NO: 49)
reverse 2: GAG TAT GGA AGG ACC TTG GT 838636
                                                  (SEQ ID NO: 50)
forward: GGA TAG AGG TGT AGG TAA ATC
                                                  (SEQ ID NO: 51)
reverse: TCC GAG ATT AGG AAT TTA TGT A 345077
                                                  (SEQ ID NO: 52)
forward: CTT CTG GAA CAG GCG AAG A
                                                  (SEQ ID NO: 53)
reverse 1: GGT GGC GCA GAG GAG GAA
                                                  (SEQ ID NO: 54)
reverse 2: GCA GAG AGA CGT GGA TGG T 825214
                                                  (SEQ ID NO: 55)
forward: GAT GAA GTT AAA TCC TCC TTT G
                                                  (SEQ ID NO: 56)
reverse: CCT CTT GTG TGC TGT GAG TT 297392
                                                  (SEQ ID NO: 57)
forward: GGT GGA AGA AGA GGT GGT G
                                                  (SEQ ID NO: 58)
reverse: GAG AGG TGT GGT GGG ATG A 897594
                                                  (SEQ ID NO 109)
forward: AGC AGG AGG AGT GGC TGA TGA A
                                                  (SEQ ID NO 110)
reverse: AGA GGG AGA AGA GGT GGT A 713886
                                                  (SEQ ID NO 111)
forward: AAG GGA GAA GTG TGA CAA GT
                                                  (SEQ ID NO 112)
reverse: TGT GGG TTG GGG GGA GTA 884867
                                                  (SEQ ID NO 113)
forward: G AGG AGG AGG AGG AAA TGA A
                                                  (SEQ ID NO 114)
reverse: GA TGG ATT GGA GGG GTT TGA 321247
                                                  (SEQ ID NO 115)
forward: GGA GGA GGA GAG TGA AGA AA
                                                  (SEQ ID NO 116)
reverse: TGG TAG GTT GTG GTT GAG AA 1630998
                                                  (SEQ ID NO 117)
forward: CCA GAG CTG CAC TCA TTC C
                                                  (SEQ ID NO 118)
reverse: CAC TGT TGG TGA TAA AGC AAT T 756595
                                                  (SEQ ID NO 119)
forward: GGA TAA AGG CTA CTT AAC AAA G
                                                  (SEQ ID NO 120)
reverse: CCA CTT TGC CAT CTC TAC AC 549728
                                                  (SEQ ID NO 121)
forward: GAG CCG AGG AGG TTG AAA G
                                                  (SEQ ID NO 122)
reverse: CTC CTC TGG GTC TAT AGT GT 203003
                                                  (SEQ ID NO 123)
forward: GAC CCT GGT GGC GGT GAA
                                                  (SEQ ID NO 124)
reverse: GGT GCC TGC AGC ATC TTC A 814731
                                                  (SEQ ID NO 125)
forward: GGA GAG CCC TGG CAC GTA
                                                  (SEQ ID NO 126)
reverse: CCT TCA TCT GCA GGT TCT TG 714196
                                                  (SEQ ID NO 127)
forward: ACG ACG GAC ACA TTA ATT ACT
                                                  (SEQ ID NO 128)
reverse: TCC ATG CTG CAG CTG ATG A 809784
                                                  (SEQ ID NO 128)
forward: C CTT CGG CAA AGG GAG AGT
                                                  (SEQ ID NO 130)
reverse: CTG GAT GAG TTC AGA GAG TTT 825293
                                                  (SEQ ID NO 131)
forward: GCC TCG ACA GGC AGA GAT
                                                  (SEQ ID NO 132)
reverse: CTT GTA GCT GAA GAT GTC AAT 246120
                                                  (SEQ ID NO 133)
forward: CTC TAT GCC CGG GAC AAG T
                                                  (SEQ ID NO 134)
reverse: AAG ACA TGT CGA AGC CAT ACA
```

Figure 2:
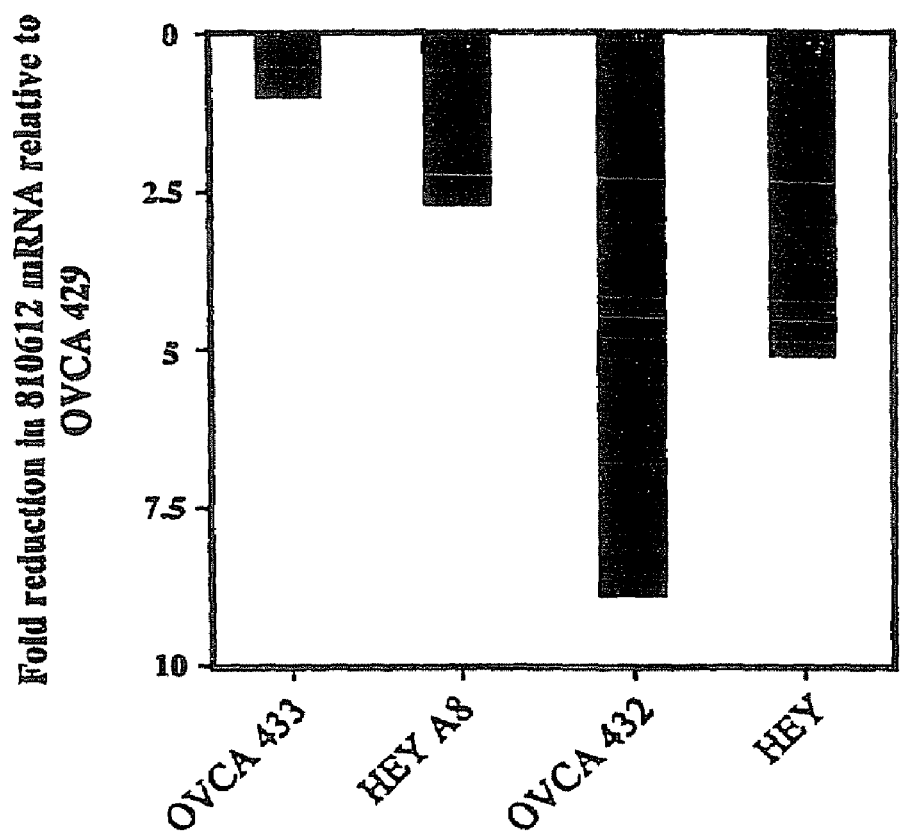
FIG. 2 is a photograph of an autoradiogram showing the results of Northern blot analysis and a graphical representation of the Northern blot results demonstrating that S100A11 is expressed at increased levels in ovarian cancer cell lines that have increased resistance to chemotherapeutic drug(s).
Figure 3:
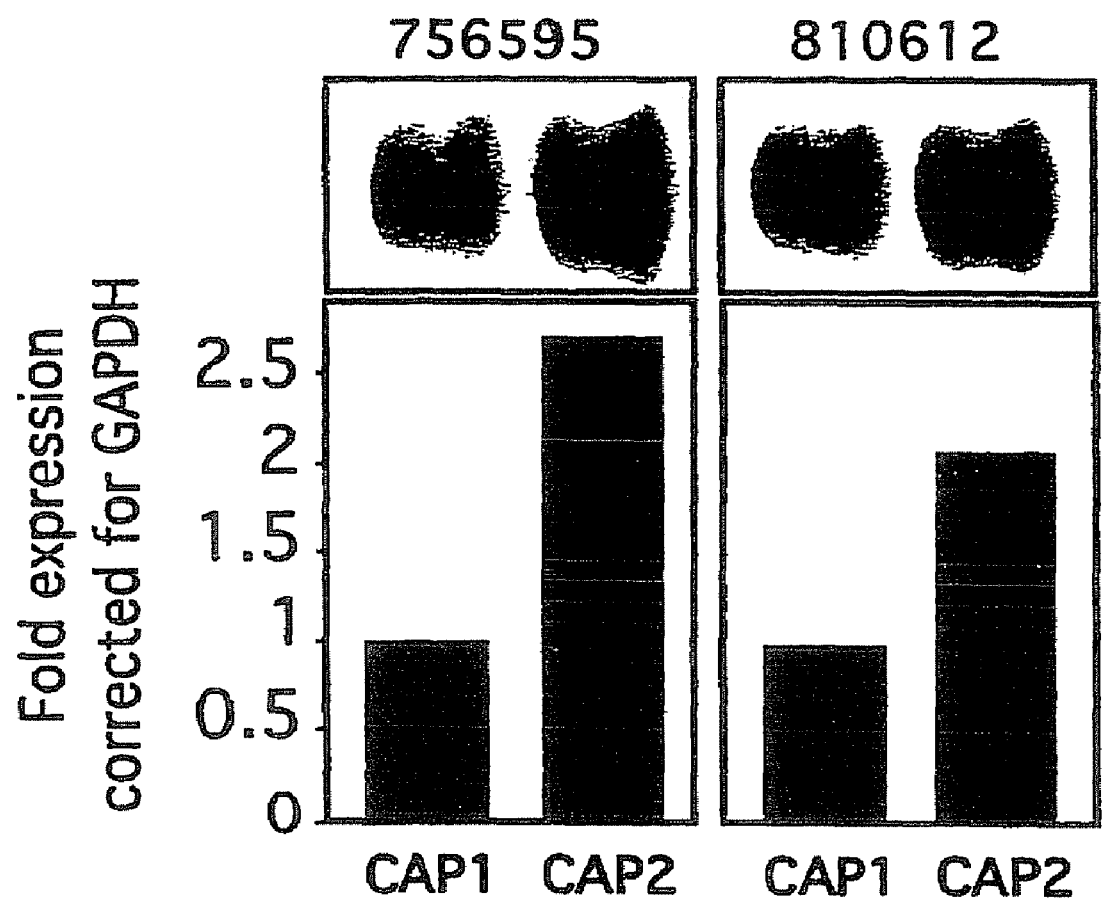
FIG. 3 is a photograph of an autoradiogram showing the results of Northern blot analysis and a graphical representation of the Northern blot results demonstrating that the mRNA levels for S100A10 and S100A11 are elevated in a patient tumor sample that is more resistant to chemotherapy compared to a sample from a more responsive patient.

Summary of Genes Up- or Down-Regulated in Ovarian Cancer Cells that are Resistant to Cis-Platin Genes Encoding EF-Hand Proteins:

Five genes encoding calcium-activated EF-Hand proteins were identified, namely, S100A10, S100A11, SPARC, Calpain 2 and Grancalcin). Two of the four genes, S100A10 and S100A11 are located adjacent to each other on chromosome 1 at 1q21 (Pejovic, 1995, *Ann. Med.* 27:73-78; Ridinger et al., 1998, *Biochimica et Biophysica Acta* 1448:254-263). This region of chromosome 1 has been reported as one of the hotbeds for chromosomal rearrangements in ovarian cancer (Pejovic, 1995, *Ann. Med.* 27:73-78). The exact biological functions of S100A10 and S100A11 are unknown. S100A10 and S100A11 are both expressed at higher levels in more resistant ovarian cancer cell lines (see FIG. 1 and FIG. 2, respectively). FIG. 3 shows that the mRNAs for S100A10 and S100A11 are also elevated in a patient that is more resistant to chemotherapy compared to a more responsive patient.

Figure 4:
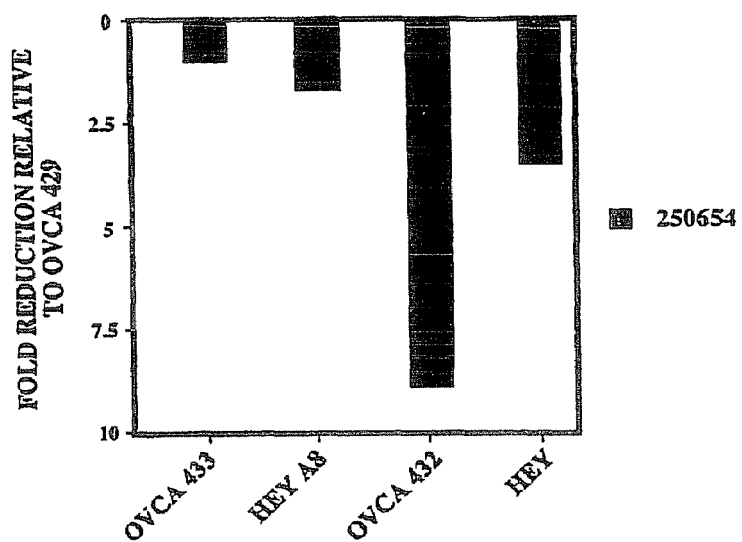
FIG. 4 is a graph representing the results of quantitative real-time PCR demonstrating that SPARC was expressed at increased levels in chemoresistant cell lines. The probe is represented by SEQ ID NO: 13.
Figure 5:
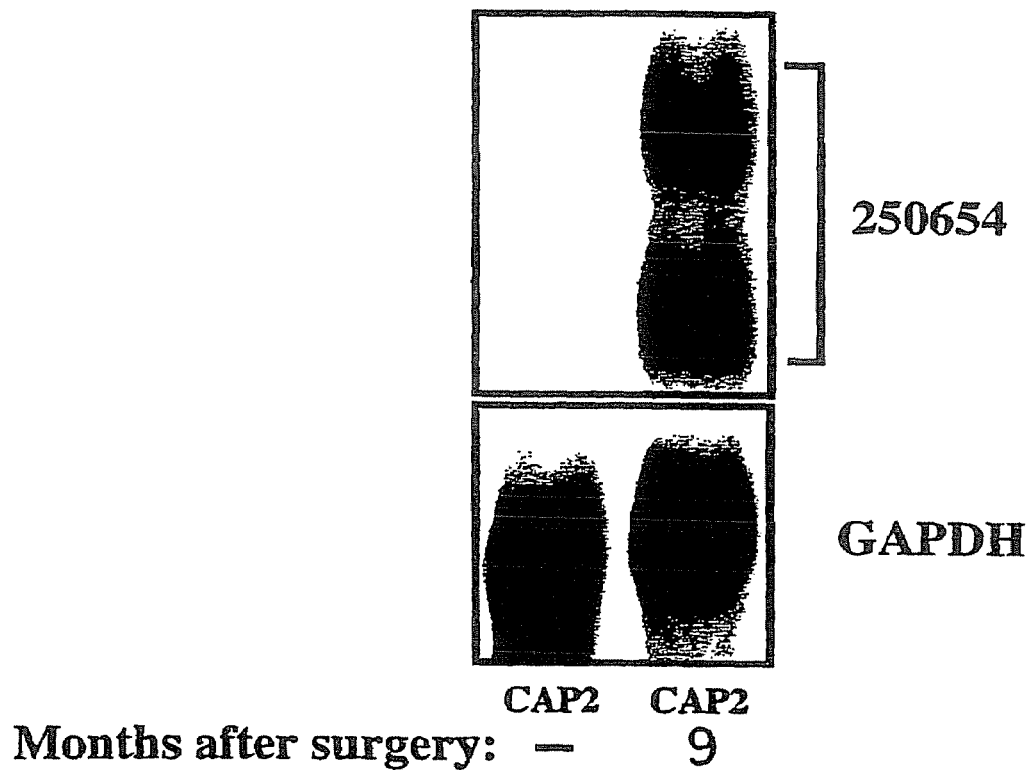
FIG. 5 is a photograph of an autoradiogram showing the results of Northern blot analysis demonstrating that SPARC mRNA was elevated in samples taken from a patient whose cancer had recurred.

SPARC (also known as Osteonectin and BM40) is a secreted protein (Lane and Sage, 1994, *FASEB J.* 8:163-173). SPARC has been shown to be highly expressed in the stroma of neoplastic ovaries (Paley et al., 2000, *Gynecologic Oncology* 78:336-341) and has been shown to induce apoptosis in ovarian cancer cells (Yiu et al., 2001, *Am. J. Pathol.* 159:609-622). However, high levels of SPARC have been detected in melanoma (Ledda et al., 1997, *J. Invest. Dermatol.* 108:210-214) and colorectal cancer (Porte et al., 1995, *Int. J. Cancer* 64:70-5), and also have been reported to promote cell migration and invasion in prostate cancer (Thomas et al., 2000, *Clin. Cancer Res.* 6:1140-9) and glioblastoma (Golembieski et al., 1999, *Int. J. Dev. Neurosci.* 17:463-72). SPARC overexpression also contributes to increased motility and invasion of breast cancer cells (Briggs et al., 2002, *Oncogene* 21:7077-91). As shown herein, SPARC was found to be expressed at higher levels in the more chemoresistant ovarian cancer cell lines (FIG. 4). SPARC mRNA was also elevated in samples taken from a patient whose tumor had recurred as shown in FIG. 5.

Figure 6:
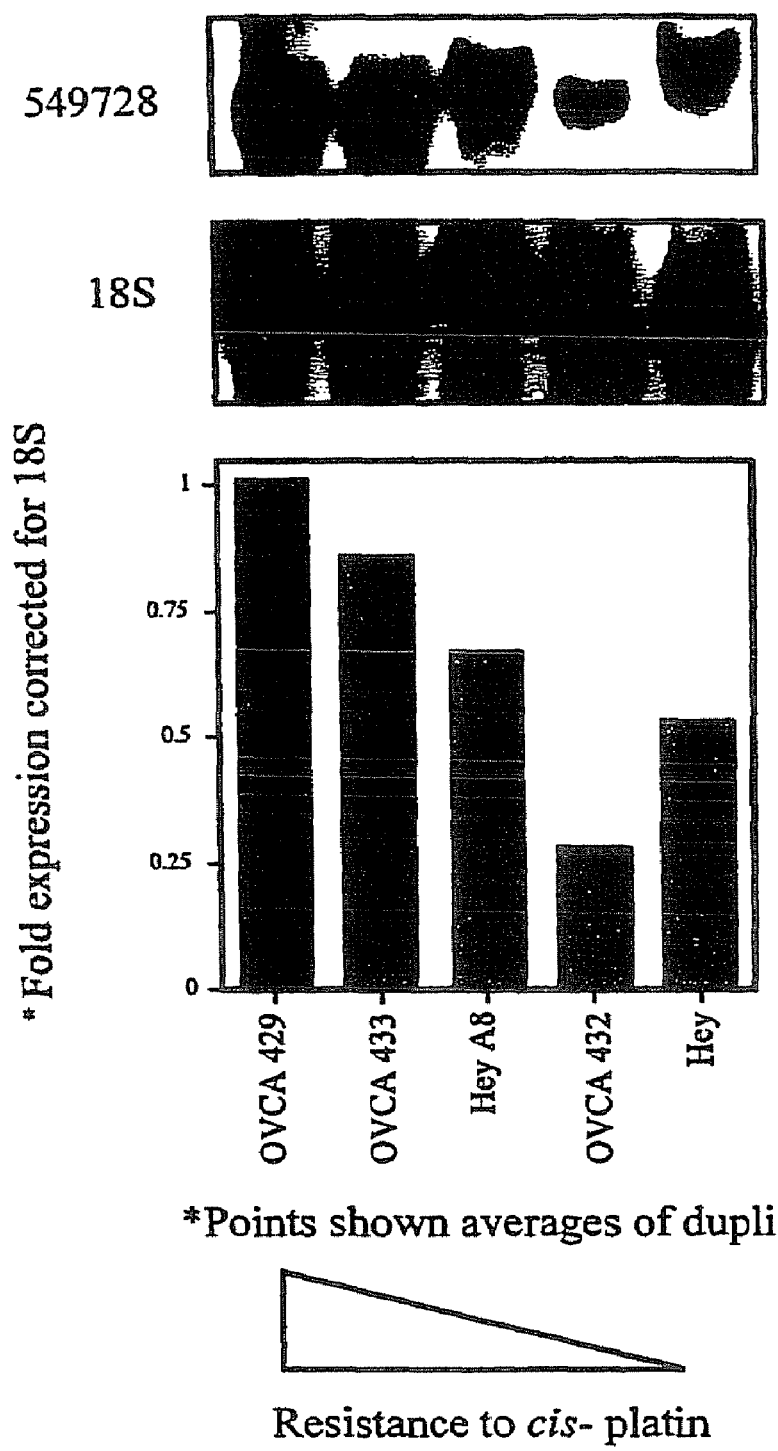
FIG. 6 is a photograph of an autoradiogram showing the results of Northern blot analysis and a graphical representation of the Northern blot results demonstrating that the levels of Calpain 2 mRNA were increased in the chemoresistant ovarian cancer cell lines.

Calpain 2 is a calcium-activated protease. Recently it was reported that an inhibitor of calpain 2 activity induced apoptosis in human acute lymphoblastic leukemia and non-Hodgkin's lymphoma as well as solid tumor cells (Huang and Wang, 2001, *TRENDS in Molecular Medicine* 7:355). Calpain 2 mRNA levels were increased in more chemoresistant ovarian cancer cell lines (FIG. 6).

Figure 7:
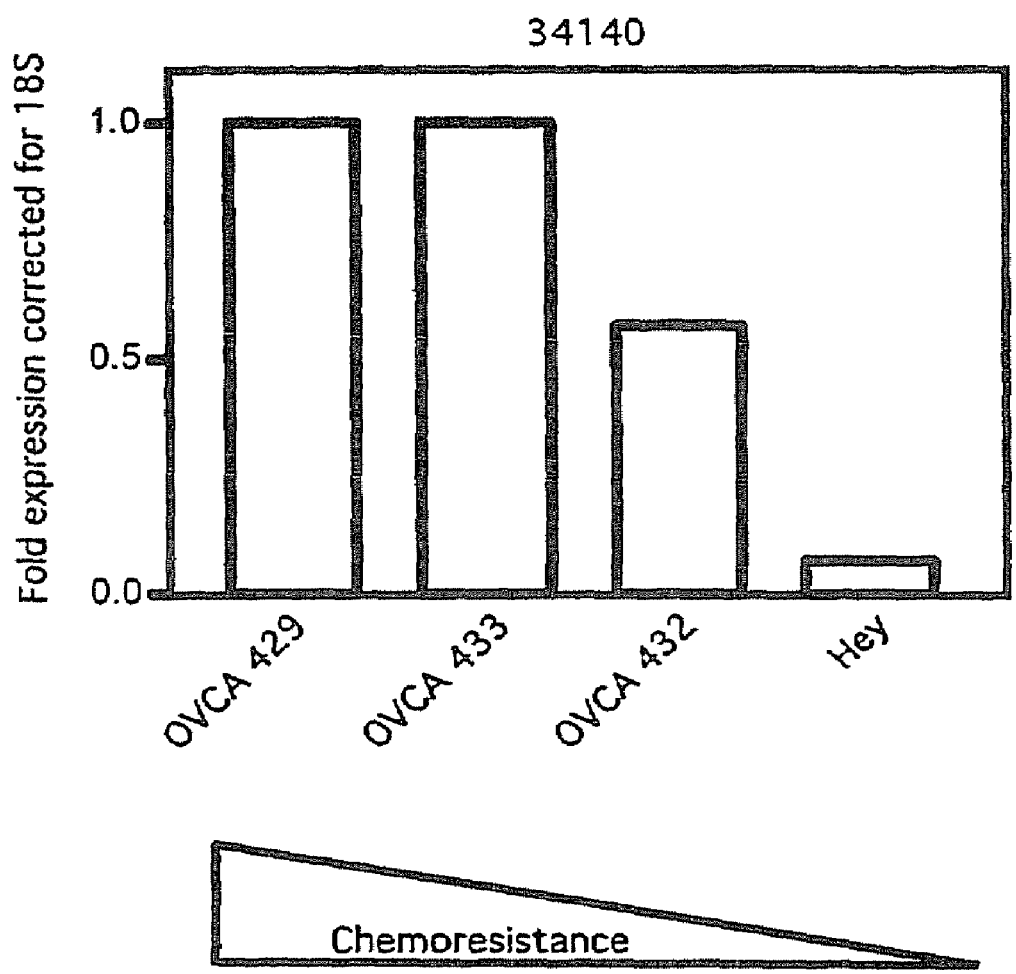
FIG. 7 is a graphical representation of Northern blot results demonstrating that Grancalcin mRNA levels were elevated in chemoresistant cell lines compared to cell lines sensitive to treatment with cis-platin.

Grancalcin is a recently-described $Ca^{2+}$-binding protein that belongs to the penta-EF-Hand subfamily of EF-Hand proteins and translocates to membranes upon $Ca^{2+}$ binding (Lollike et al., 2001, *J. Biol. Chem.* 276:17762-9). Grancalcin mRNA was found to be elevated in cell lines more resistant to cis-platin compared to cell lines more responsive to treatment with cis-platin (FIG. 7).

Figure 10:
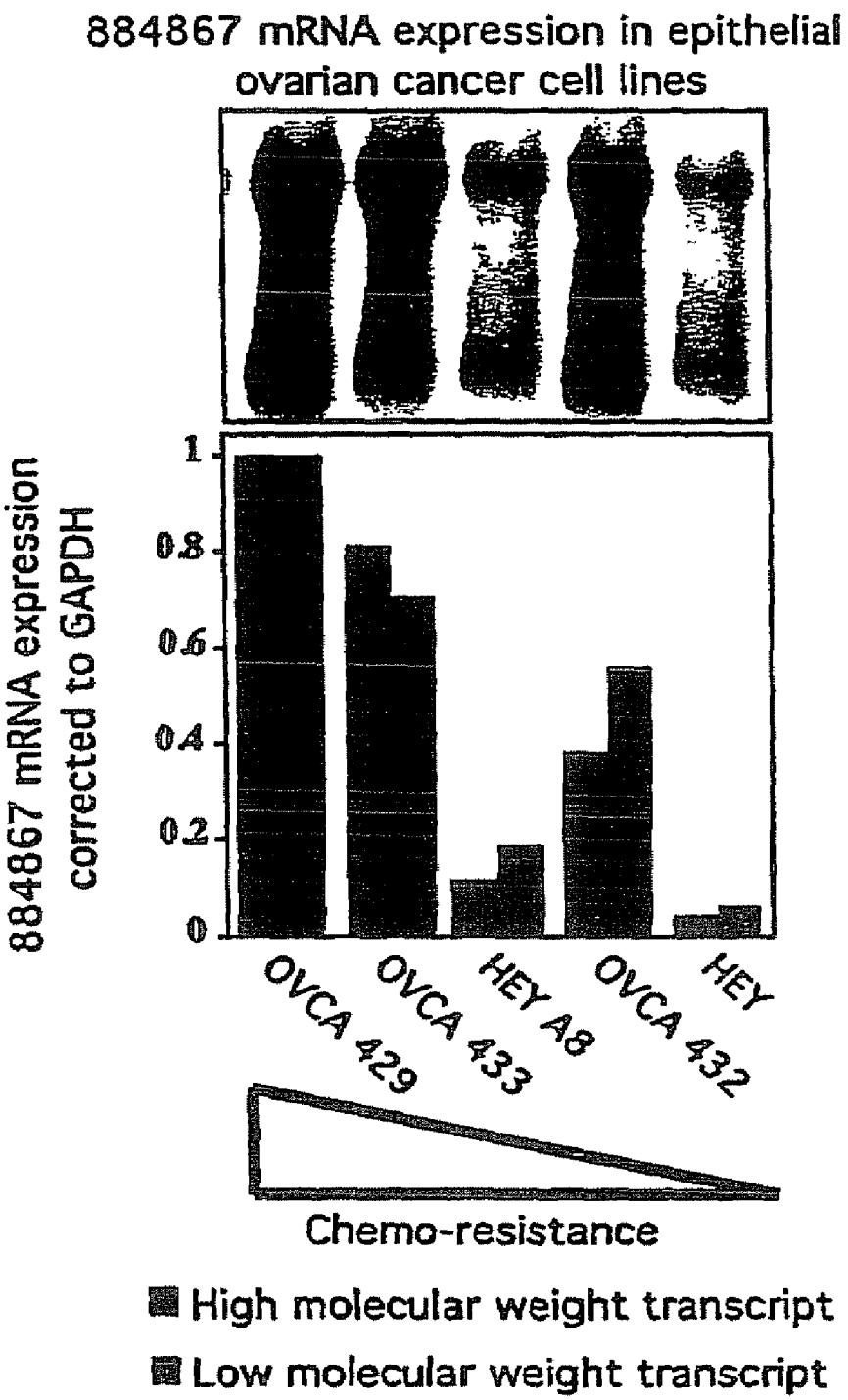
FIG. 10 is a photograph of an autoradiogram showing the results of Northern blot analysis and a graphical representation of the Northern blot results demonstrating that two transcripts of eIF5 were detected and that expression levels of both were elevated in ovarian cancer cell lines with the highest level of resistance to cis-platin.
Figure 11:
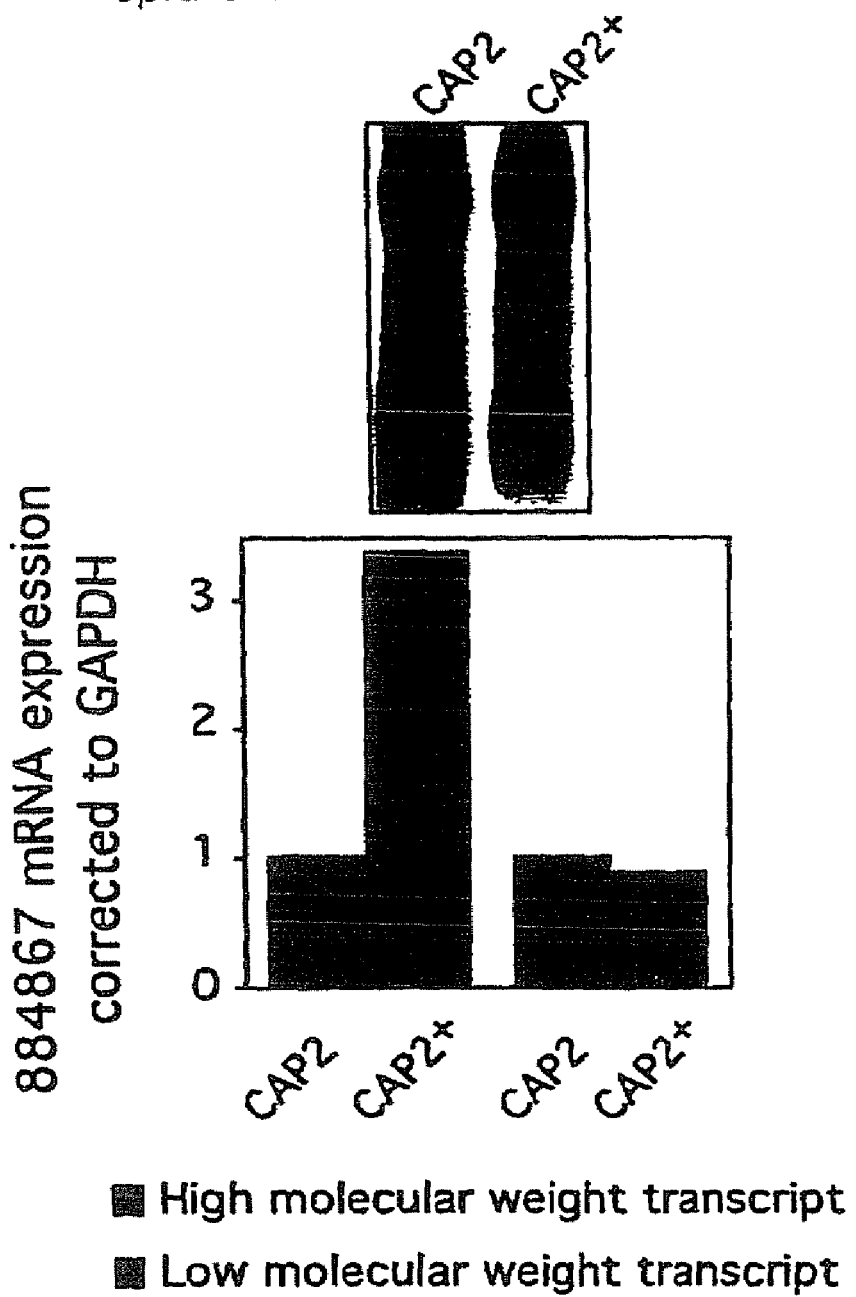
FIG. 11 is a photograph of an autoradiogram showing the results of Northern blot analysis and a graphical representation of the Northern blot results demonstrating expression of eIF5 in a chemoresistant patient tumor sample before (CAP2) and after the recurrence of the tumor (CAP2+).

Genes Encoding Proteins Involved in Protein Translation and Translational Control:

MetAP2: The expression of Methionine aminopeptidase 2 (also known as eIF-2 associated p67) has never been linked to ovarian cancer. The protein encoded by this gene seems to have two functions. It removes the first methionine from newly synthesized proteins (Li and Chang, 1996, *Biochem. Biophys. Res. Commun.* 227:152-9) and it also associates with eukaryotic initiation factor 2α (eIF-2α; a GTP binding protein) and inhibits its phosphorylation (Wu et al., 1993, *J. Biol. Chem.* 268:10796-10801). Using an antibody against the MetAP2, it appears that MetAP2 expression is elevated in the most resistant cell line OVCA 429 and down-regulated in Hey (the cell line most sensitive to cis-platin; see FIG. 8). Furthermore, when MetAP2 mRNA expression was examined in tissue samples obtained from three patients with different levels of resistance to cis-platin-based chemotherapy, MetAP2 appeared to be most elevated in the sample from the most resistant patient (CAP3 in FIG. 9) compared to patients with intermediate (CAP2; FIG. 9) and low (CAP1; FIG. 9) levels of resistance to chemotherapy. A drug, TNP-470, that specifically targets MetAP2 is currently in clinical trials as an angiogenesis inhibitor in several human tumors (Kruger and Figg, 2000, *Expert Opin. Investig. Drugs* 9:1383-96). Furthermore, lowering the cellular levels of MetAP2 using antisense oligonucleotides has been shown to induce apoptosis (Datta and Datta, 1999, *Exp. Cell Res.* 246:376-83). These observations suggest that this protein could be an important target for therapy in ovarian cancer.

eIF5 is another central protein for translation initiation and protein synthesis that functions as a GTPase-activator protein (Paulin et al., 2001, *Current Biol.* 11:55-9; Das et al., 2001, *J. Bio. Chem.* 276:6720-6). Two transcripts were detected and the levels of expression of both were elevated in ovarian cancer cell lines with the highest level of resistance to cis-platin (FIG. 10) and in a more resistant patient (FIG. 11).

Figure 12:
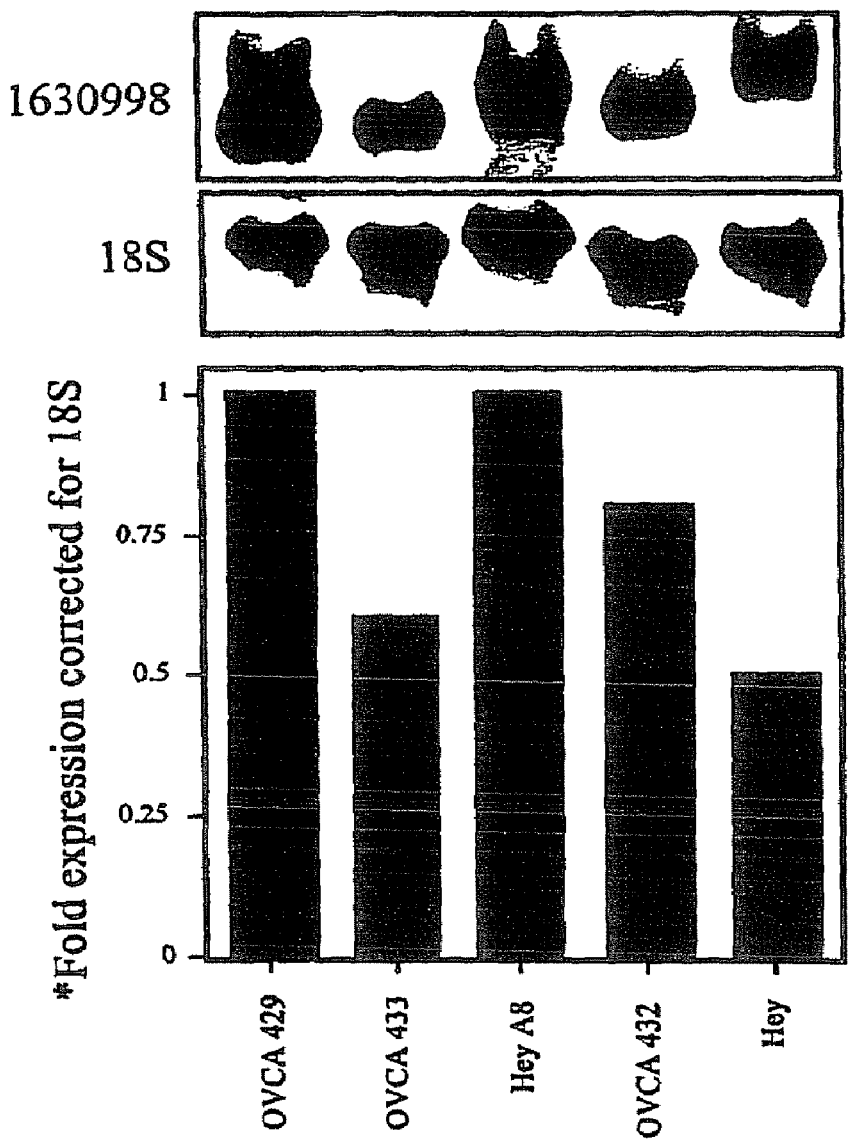
FIG. 12 is a photograph of an autoradiogram showing the results of Northern blot analysis and a graphical representation of the Northern blot results demonstrating that mRNA for eIF2Bε was elevated in chemoresistant cell lines.
Figure 12:
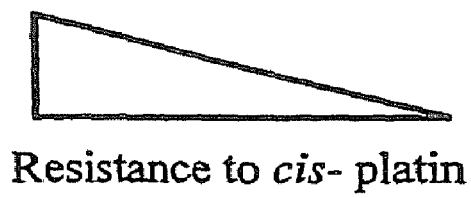
Figure 13:
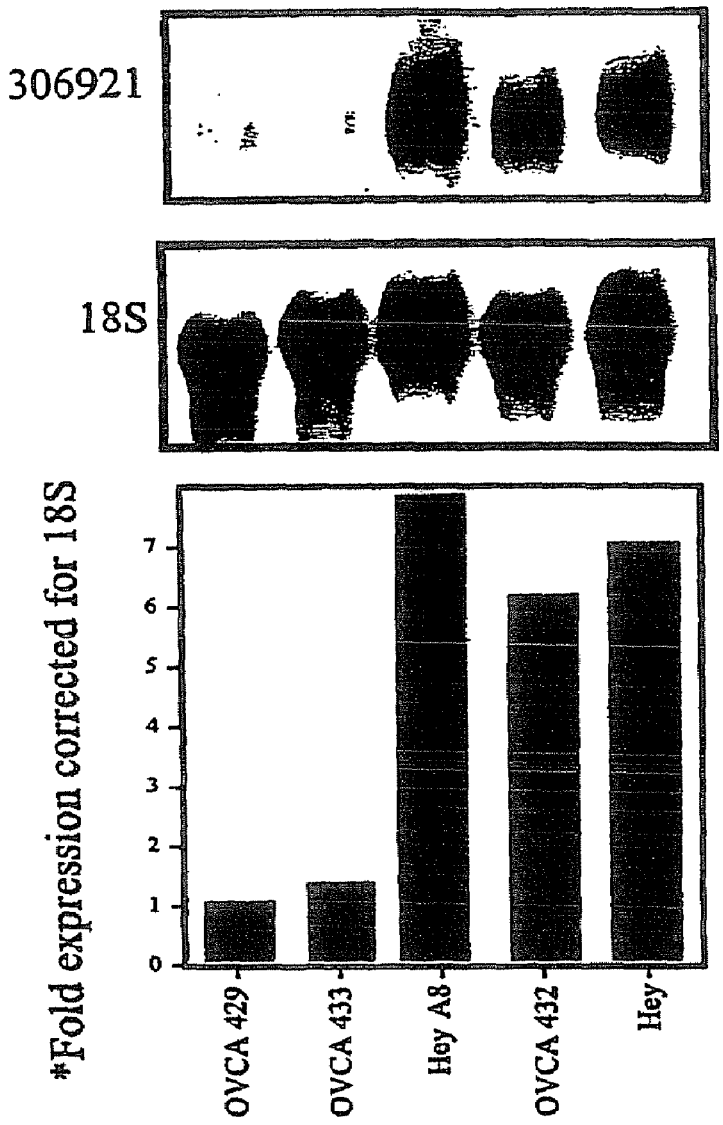
FIG. 13 is a photograph of an autoradiogram showing the results of Northern blot analysis and a graphical representation of the Northern blot results demonstrating that eEF1ε mRNA was down-regulated in ovarian cancer cell lines that were the most resistant to cis-platin.
Figure 13:

The mRNA for eIF2Bε is upregulated in ovarian cancer cell lines showing the highest resistance to cis-platin (FIG. 12). The protein encoded by this gene is the regulatory ε-subunit of a guanine nucleotide exchange factor complex comprised of 5 subunits (Proud, 2001, *Prog. Mol. Subcell. Biol.* 26:95-114).

eEF1 epsilon mRNA was down-regulated in ovarian cancer cell lines showing the highest resistance level to cis-platin (FIG. 13). eEFs are involved polypeptide assembly (Browne and Proud, 2002, *Eur. J. Biochem.* 269: 5360-8).

Figure 14:
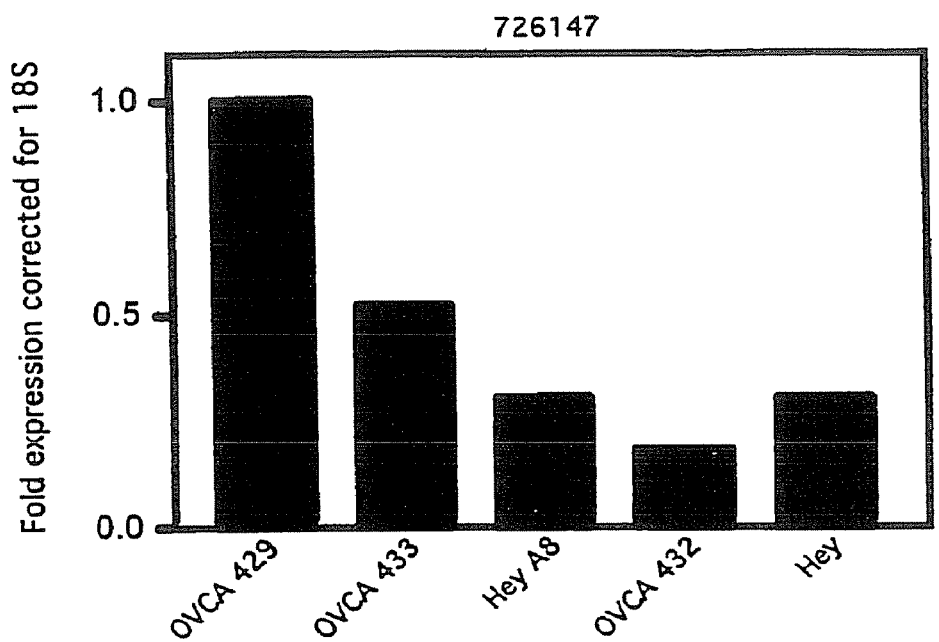
FIG. 14 shows a graphical representation of Northern blot results demonstrating SAPK/Erk1 mRNA levels were elevated in cis-platin resistant cell lines compared to sensitive cell lines.

Kinases:

SAPK/Erk Kinase 1 is a dual-specificity kinase that activates JNK1, JNK2 and p38 but not Erk1 or Erk2 (Cuenda, 2000, *Int. J. Biochem. Cell Biol.* 32:581-7). This gene and its protein have not heretofore been associated with ovarian cancer. mRNA levels for this gene were found to be elevated in more resistant cell lines compared to more sensitive cell lines (FIG. 14).

Figure 15:
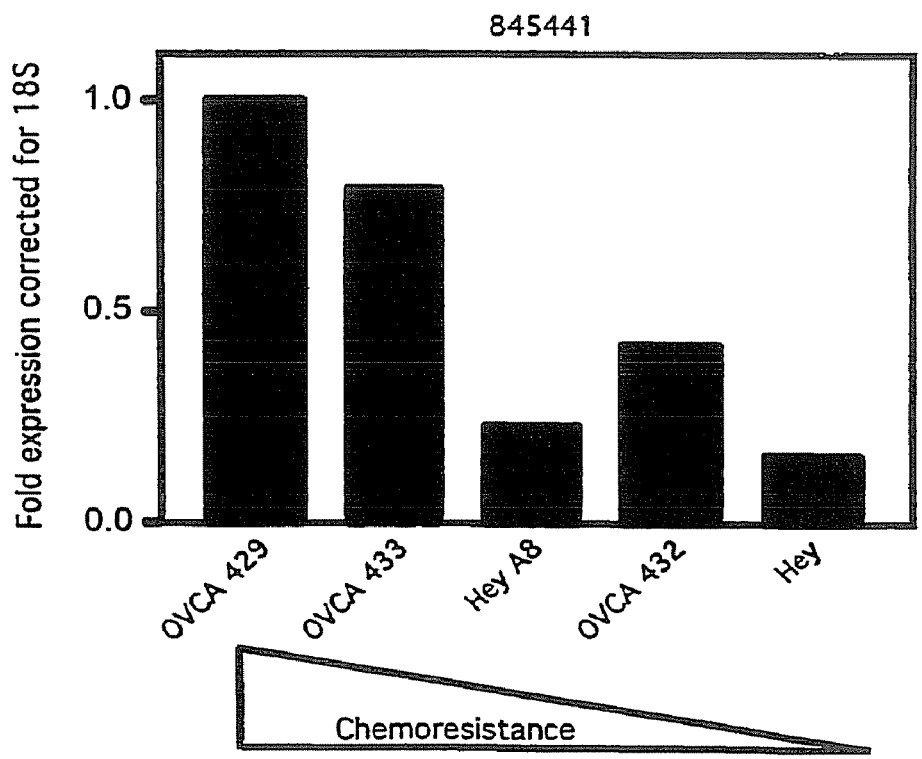
FIG. 15 shows a graphical representation of the Northern blot results demonstrating that TESK2 mRNA was elevated in cis-platin resistant cell lines.

TESK2: This serine/threonine kinase is located predominantly in the cell nucleus. When inactive, however, it translocates to the cytoplasm. TESK2 specifically phosphorylates cofilin (at Ser-3), a protein that, along with actin-depolymerizing factor plays an essential role in the rapid turnover of actin filaments and actin-based reorganization by stimulating depolymerization and severance of actin filaments (Toshima, 2001, *J. Biol. Chem.* 276:31449-58). No previous link to ovarian cancer has been reported. TESK2 mRNA is elevated in more resistant cell lines (FIG. 15).

Figure 16:
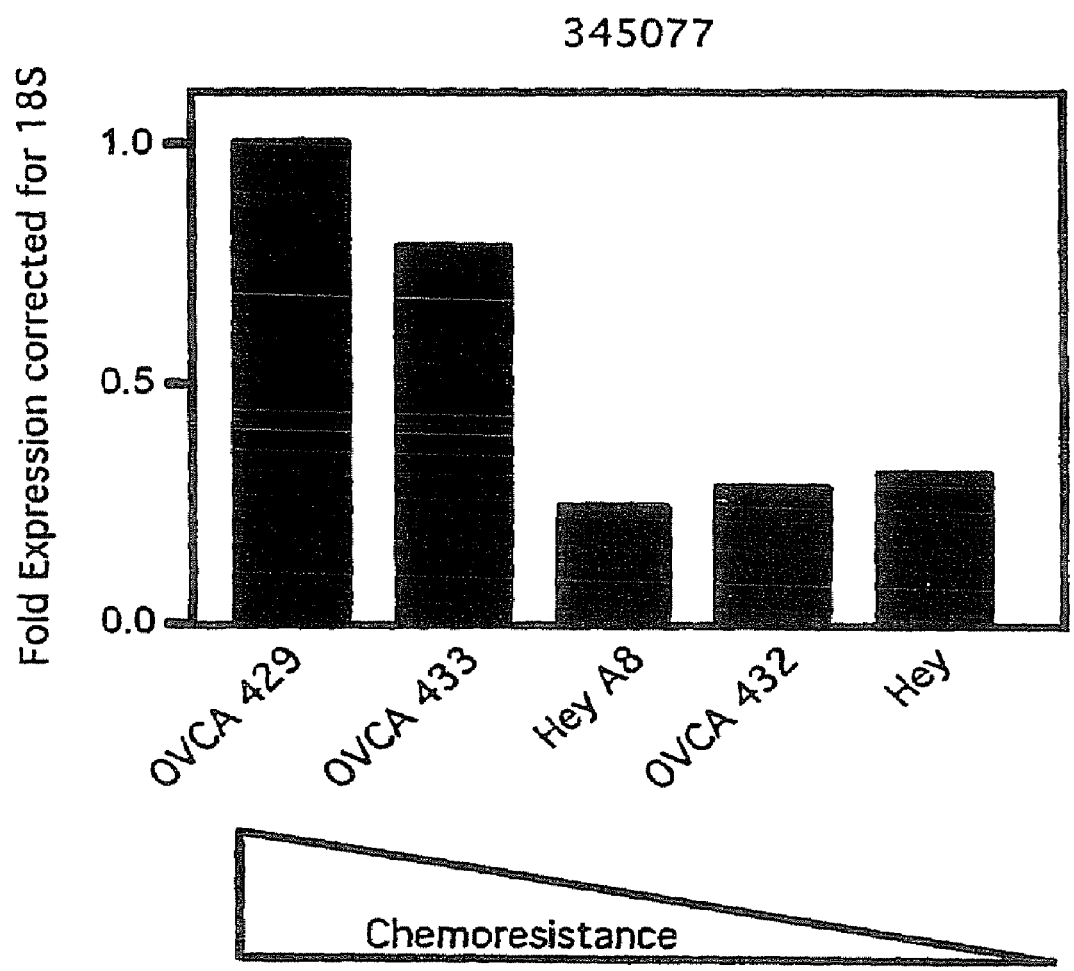
FIG. 16 shows a graphical representation of the Northern blot results demonstrating that FAST kinase mRNA was elevated in cis-platin resistant cell lines.

FAST kinase: This is a Fas-activated serine/threonine kinase, which is thought to be involved in apoptosis mediated by Fas (Tian et al., 1995, *J. Exp. Med.* 182:865-74). FAST kinase mRNA is elevated in more chemoresistant cell lines (FIG. 16).

Figure 17:
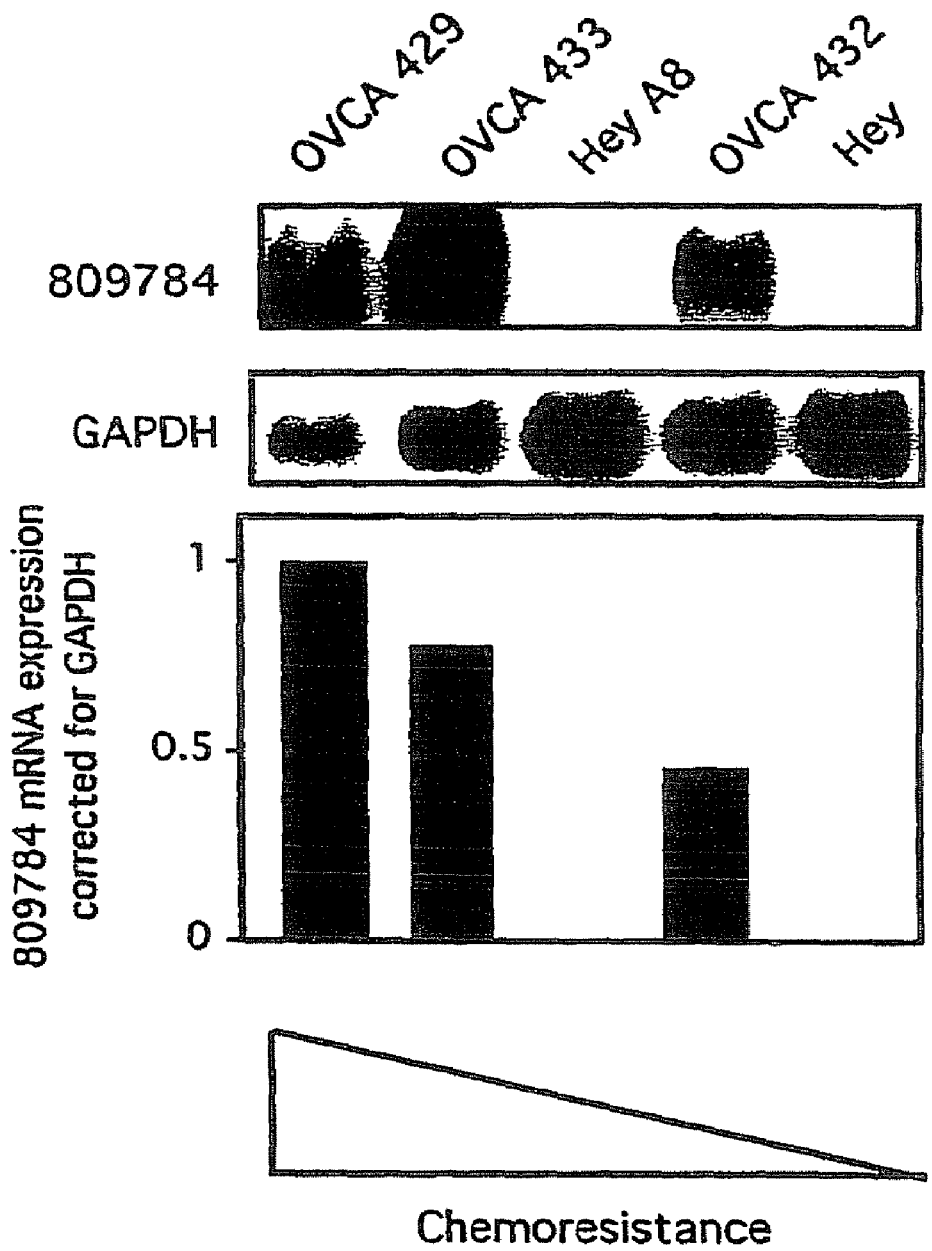
FIG. 17 is a photograph of an autoradiogram showing the results of Northern blot analysis and a graphical representation of the Northern blot results demonstrating that levels of expression of KLK6 were elevated in tested cis-platin resistant cell lines.

Others:

KLK6: This is a serine protease also known as Zyme and Neurosin. This gene belongs to the human kallilrein gene family, which also includes better-known molecules such as prostate specific antigen (PSA) already being used as a marker for prostate cancer and is also being investigated as a marker for ovarian cancer (Diamandis, 2000, *Clinical Biochem.* 33:579-83). Elevated serum levels of KLK6 have been reported in patients with ovarian cancer compared to normal controls (Diamandis, 2000, *Clinical Biochem.* 33:579-83). Expression levels of this gene were elevated in the more chemoresistant cell lines tested (FIG. 17). It is also worthwhile noting that this gene is located in another area of frequent chromosomal re-arrangements in ovarian cancer (Pejovic, 1995, *Ann. Med.* 27:73-78).

Figure 18:
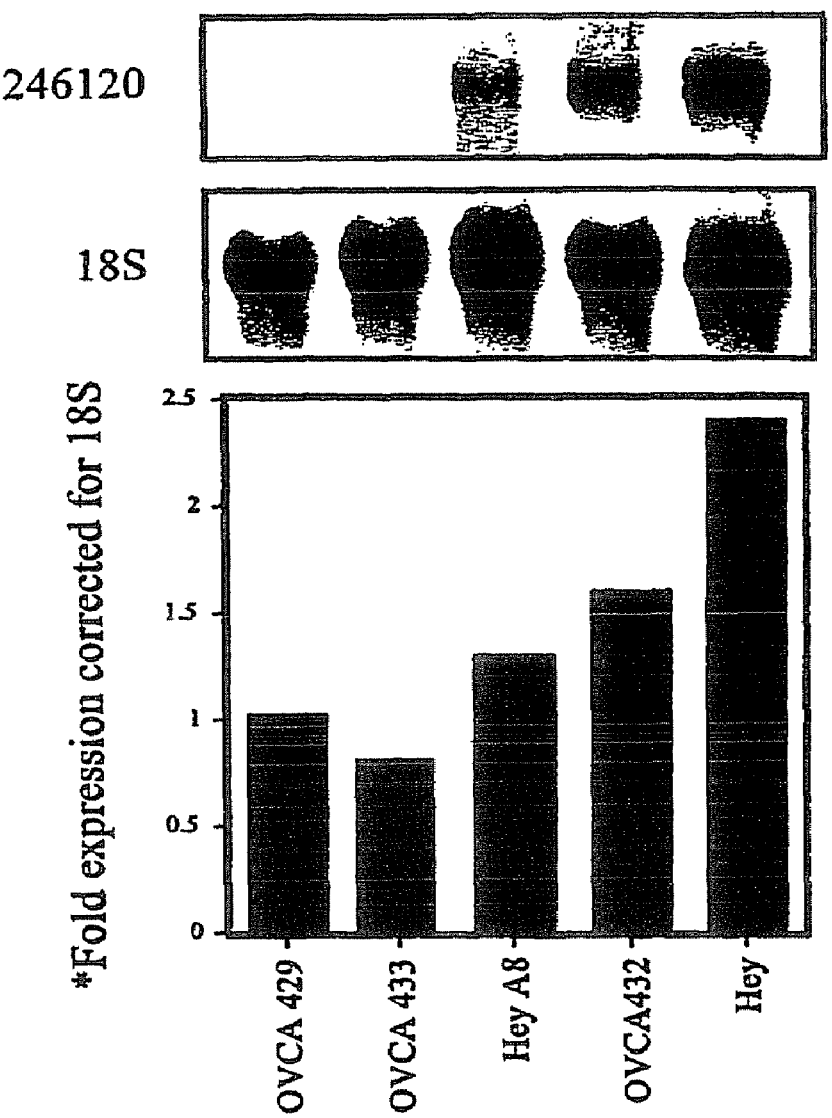
FIG. 18 is a photograph of an autoradiogram showing the results of Northern blot analysis and a graphical representation of the Northern blot results demonstrating that the expression of HMT1 was down-regulated in cells that are resistant to cis-platin.

HMT1 (also known as PRMT1): This gene encodes a protein arginine N-methyltransferase, the expression of two variants of which was found to be down-regulated in breast cancer (Scorlis et al., 2000, *Biochem. Biophys. Res. Commun.* 278: 349-59). HMT1 expression was down-regulated in cells that are more resistant to cis-platin (see FIG. 18). It is also interesting to note that HMT1 is located on chromosome 19 at 19q13.3 in the same chromosomal region where the gene encoding KLK6 resides.

Figure 19:
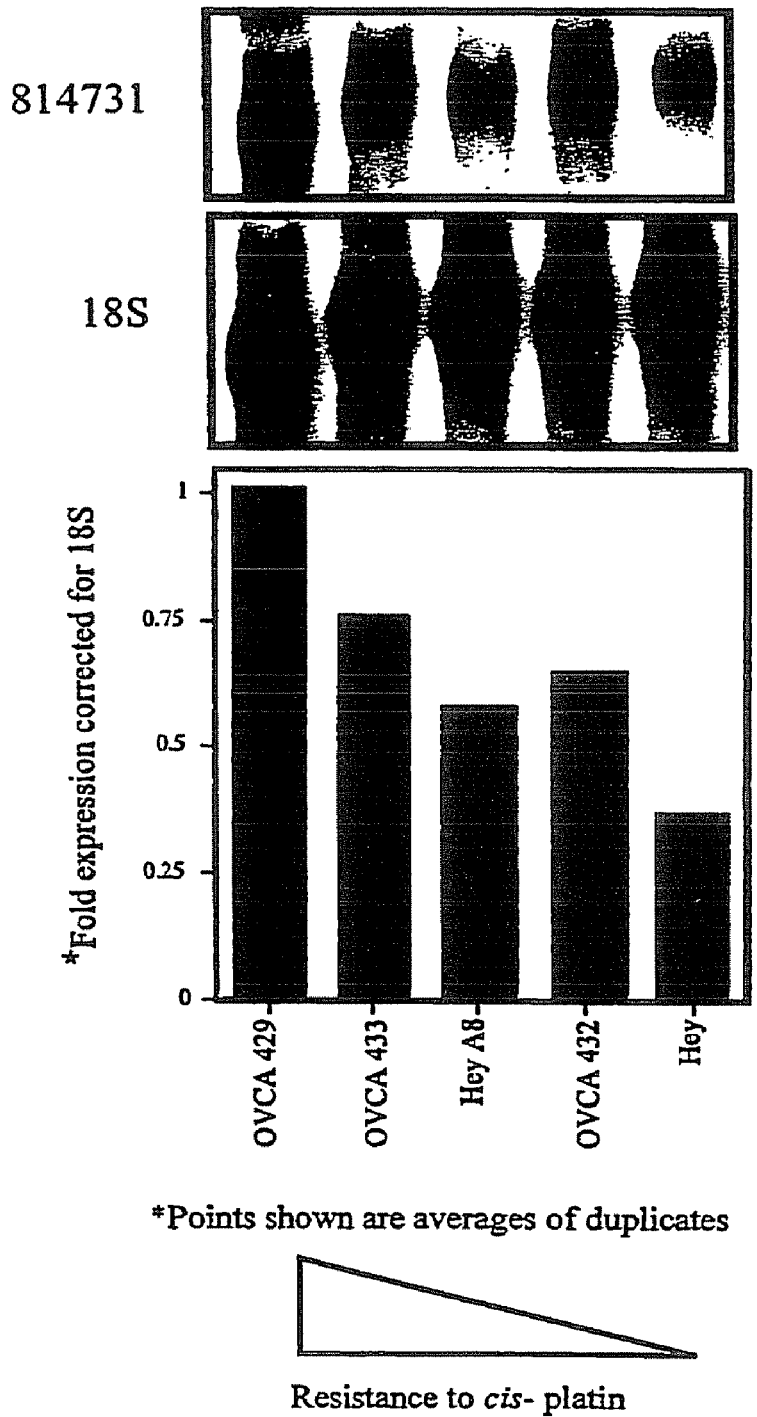
FIG. 19 is a photograph of an autoradiogram showing the results of Northern blot analysis and a graphical representation of the Northern blot results demonstrating that mRNA from ARA9 was elevated in cell lines resistant to cis-platin.

ARA9 (also known as Aryl hydrocarbon receptor-interacting protein (AIP) and XAP2) is thought to play a role in AHR-mediated signaling (Kazlauskas et al., 2002, *J. Biol. Chem.* 277:11795-801). mRNA from this gene was elevated in cell lines more resistant to cis-platin (FIG. 19). It is also located on chromosome 11 (at 11q13.3), another area with increased frequency of chromosomal rearrangements associated with ovarian cancer (Pejovic, 1995, *Ann. Med.* 27:73-78).

Figure 20:
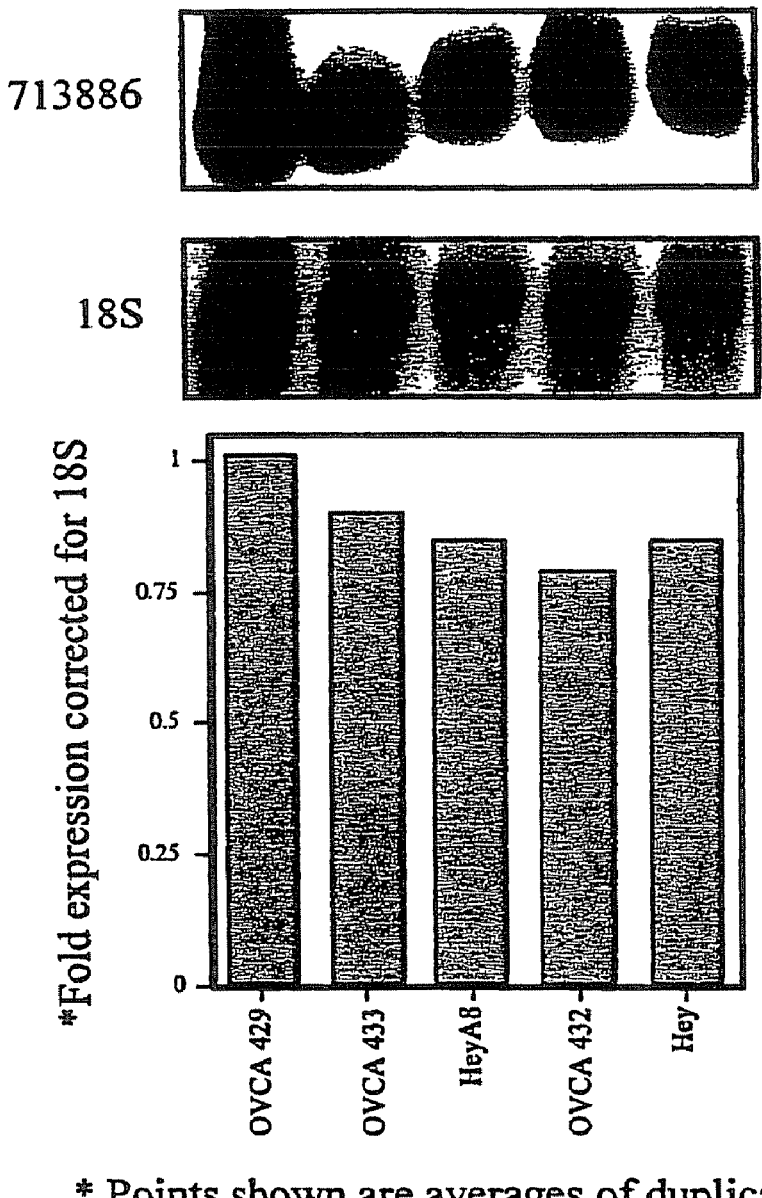
FIG. 20 is a photograph of an autoradiogram showing the results of Northern blot analysis and a graphical representation of the Northern blot results demonstrating that expression of Calponin 2 was elevated in chemoresistant cell lines compared to chemosensitive ovarian cancer cell lines.
Figure 20:
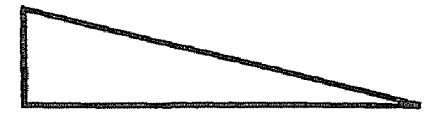

Calponin 2 has been studied in myoepithelial carcinomas (Mosunjac et al., 2000, *Diagn. Cytophathol.* 23:151-5) but not in ovarian cancer. The expression of Calponin 2 was slightly elevated in the more cis-platin resistant cell lines compared to the more sensitive ovarian cancer cell lines (FIG. 20).

Figure 21:
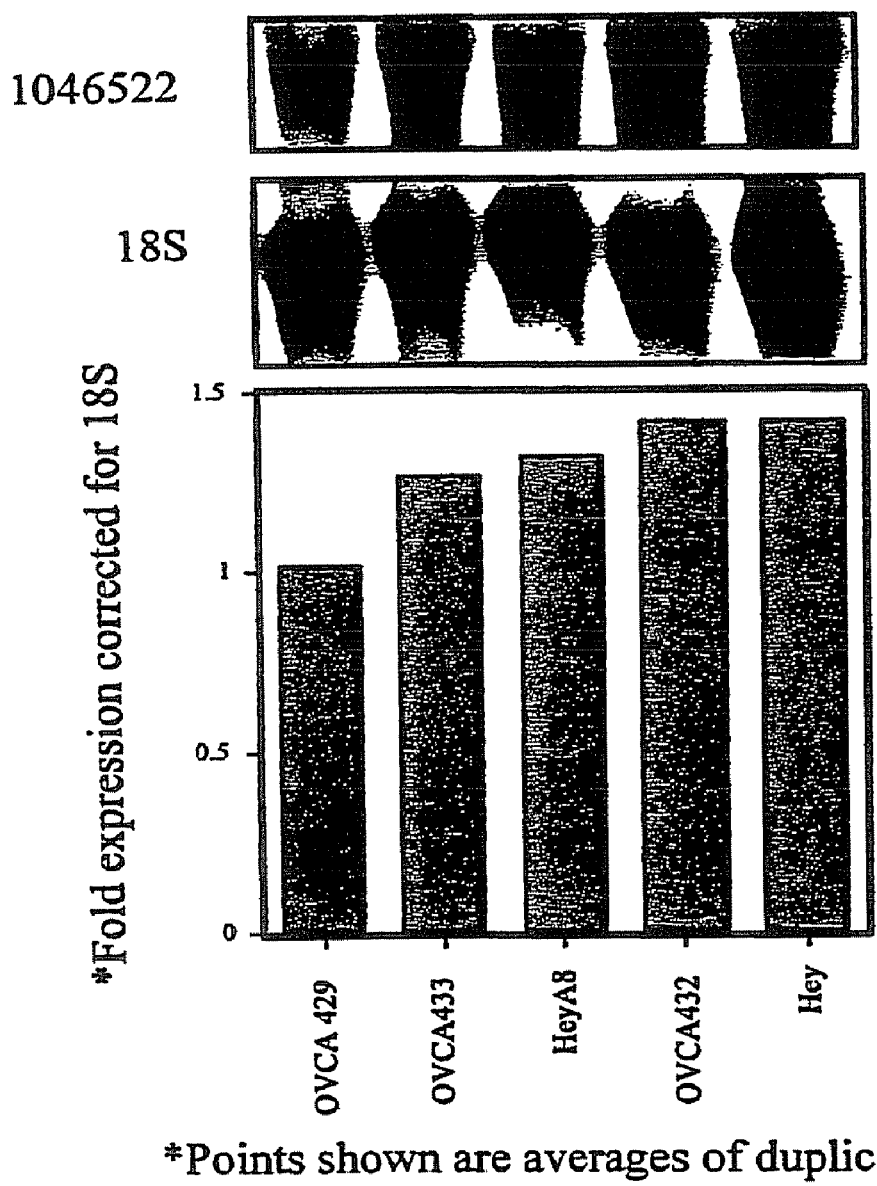
FIG. 21 is a photograph of an autoradiogram showing the results of Northern blot analysis and a graphical representation of the Northern blot results demonstrating that neuronal apoptosis inhibitory protein gene expression was decreased in cell lines most resistant to cis-platin.

Neuronal apoptosis inhibitory protein (NAIP) was found to be slightly down-regulated in cell lines most resistant to cis-platin (FIG. 21). NAIP has never been linked to ovarian cancer (Tamm et al., 2000, *Clin. Cancer Res.* 6:1796-1803).

Figure 22:
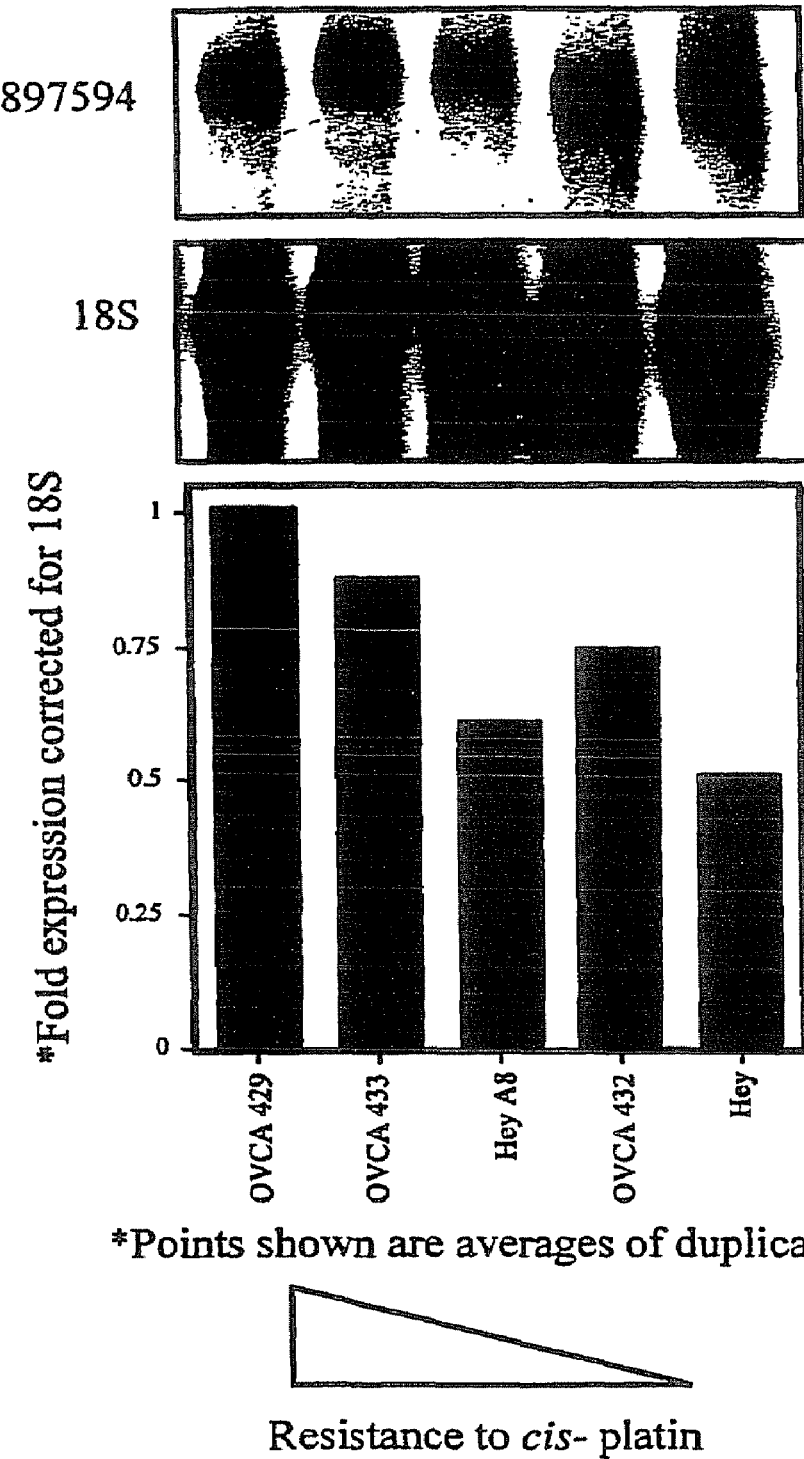
FIG. 22 is a photograph of an autoradiogram showing the results of Northern blot analysis and a graphical representation of the Northern blot results demonstrating that RNPS1 levels were elevated in cell lines resistant to cis-platin.

RNA binding protein S1 (RNPS1) is a general activator of pre-mRNA splicing and may form a complex with ASAP that is involved in promoting apoptosis and the SART3 tumor rejection antigen (Schwerk et al., 2003, *Mol. Cell Biol.* 23:2981-90; Harada et al., 2001, *Int. J. Cancer* 93:623-8). Its levels were found to be elevated in cell lines resistant to cis-platin (FIG. 22).

Figure 23:
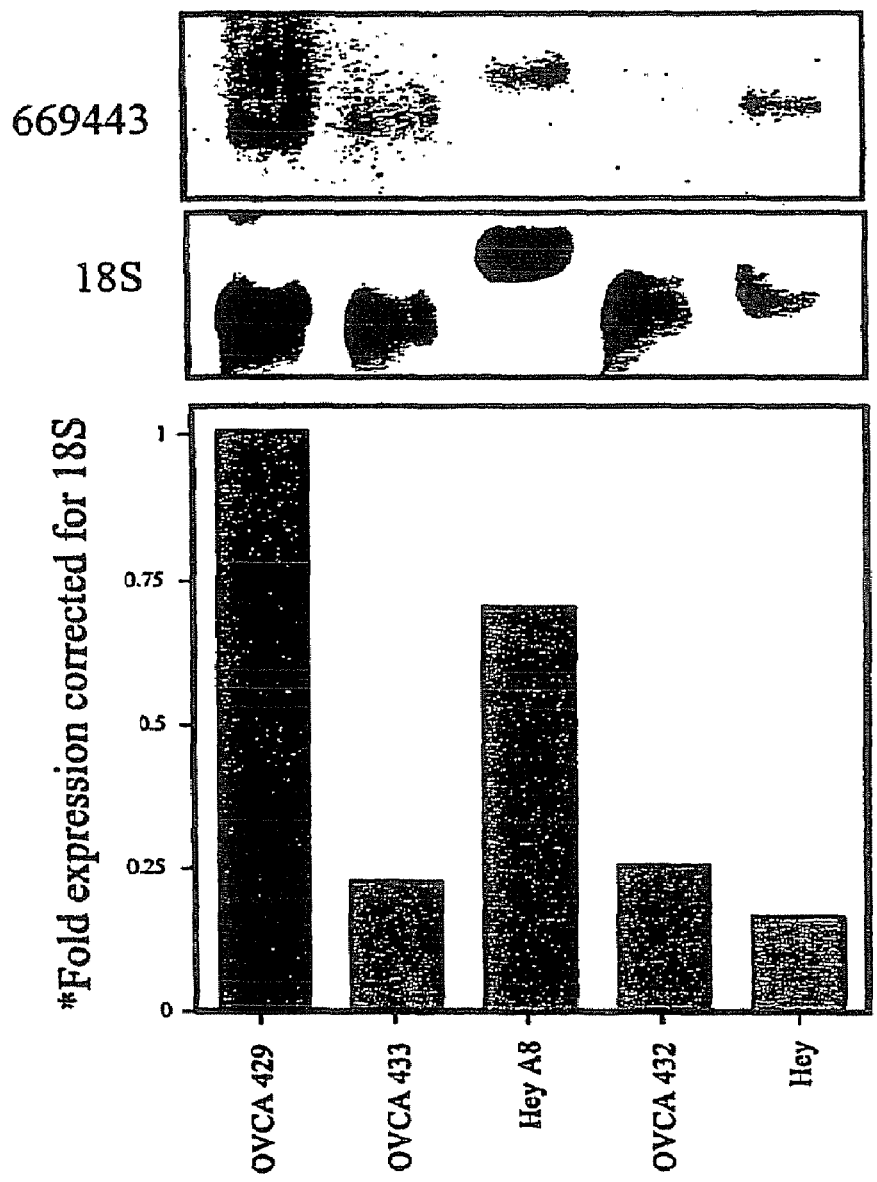
FIG. 23 is a photograph of an autoradiogram showing the results of Northern blot analysis and a graphical representation of the Northern blot results demonstrating that mRNA levels for HSF2 were elevated in the chemoresistant cell lines.
Figure 23:

Heat Shock Transcription Factor 2 (HSF2) regulates expression of heat shock protein genes (Mathew et al., 1998, *Mol. Cell Biol.* 18:5091-8). HSF2 also appears to be able to compete with the catalytic subunit of protein phosphatase 2A (PP2A) for binding to its regulatory subunit PR65, and is thought to act as a novel PP2A regulatory protein (Hong et al., 2000, *Biochem. Biophys. Res. Commun.* 272:84-9). mRNA levels for HSF2 were elevated in the more resistant cell lines (FIG. 23).

Figure 24:
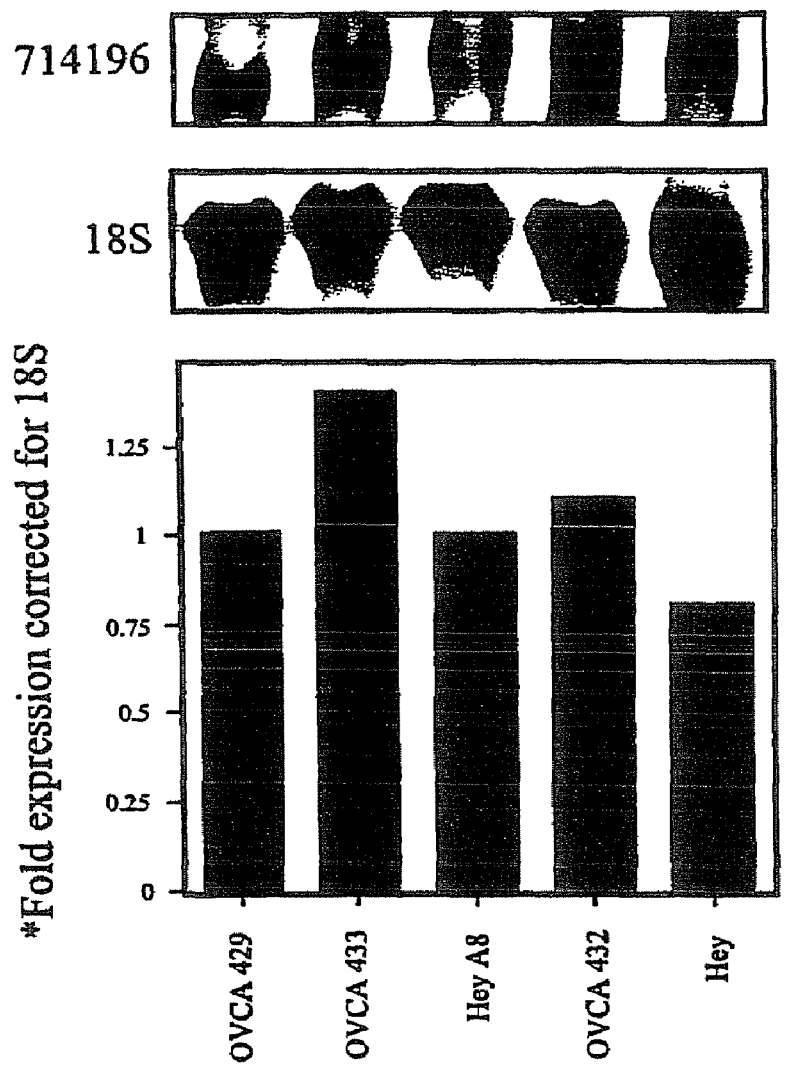
FIG. 24 is a photograph of an autoradiogram showing the results of Northern blot analysis and a graphical representation of the Northern blot results demonstrating that mRNA for WDR1 was elevated in chemoresistant cell lines compared to chemosensitive cell lines.
Figure 24:
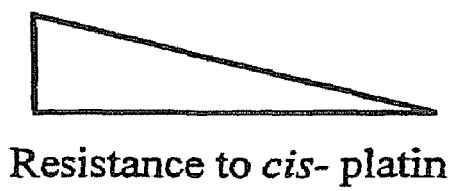

WDR1: The WD-repeat proteins are found in all eukaryotes and play an important role in the regulation of a wide variety of cellular functions including signal transduction, transcription and proliferation (Li et al., 2000, *Biochem. Biophys. Res. Commun.* 274:117-23). However, the exact function of WDR1 is unknown. The mRNA for this gene was elevated in more resistant cell lines compared to the more sensitive cell lines (FIG. 24).

Figure 25:
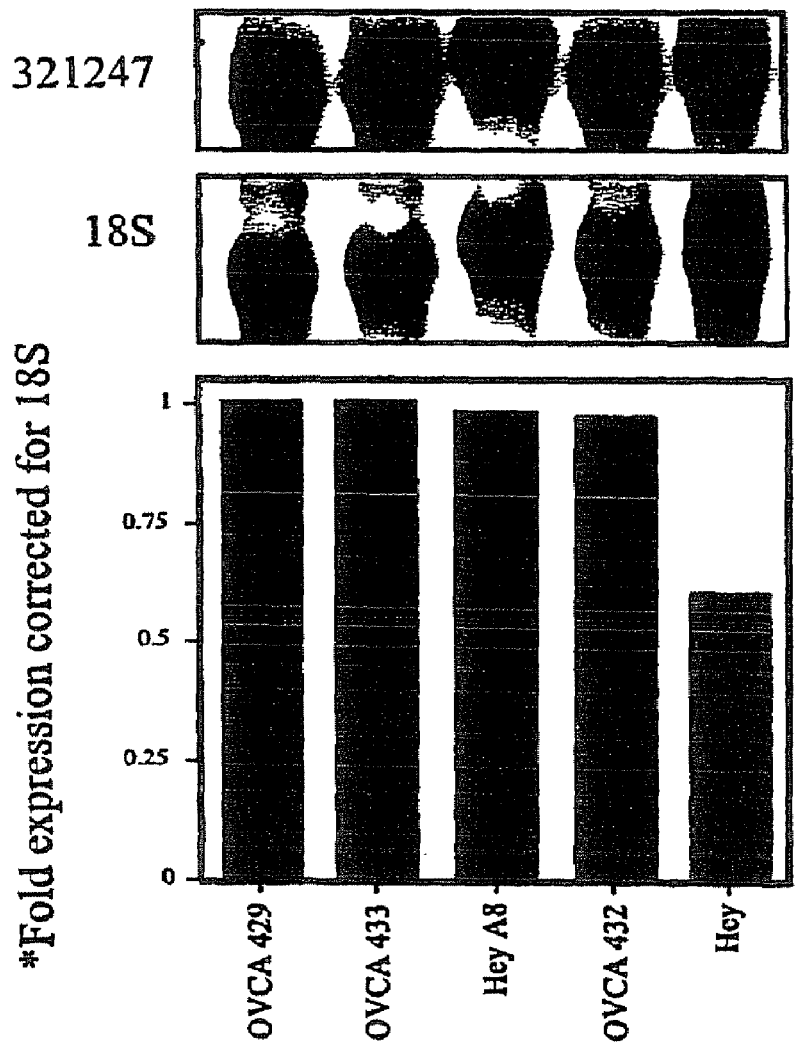
FIG. 25 is a photograph of an autoradiogram showing the results of Northern blot analysis and a graphical representation of the Northern blot results demonstrating that levels of Ft1 mRNA was elevated in cell lines that are resistant to cis-platin.
Figure 25:
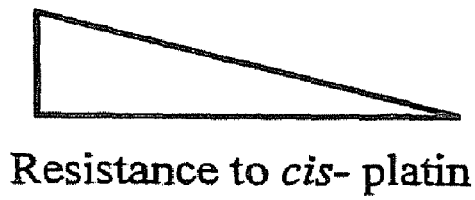

Ft1: The open reading frame of this gene exhibits similarities to ubiquitin-conjugating enzymes and in mice it maps close to the Rb-related p130 gene (Lesche et al., 1997, *Mamm. Genome* 8:879-83). Cytogenetically, Ft1 maps to chromosome 16 at region 16q12.2, an area repeatedly altered in human cancer. Loss of heterozygosity has been reported in this chromosomal region in ovarian cancer. The levels of Ft1 mRNA were elevated in cell lines that are more resistant to cis-platin (FIG. 25).

Figure 26:
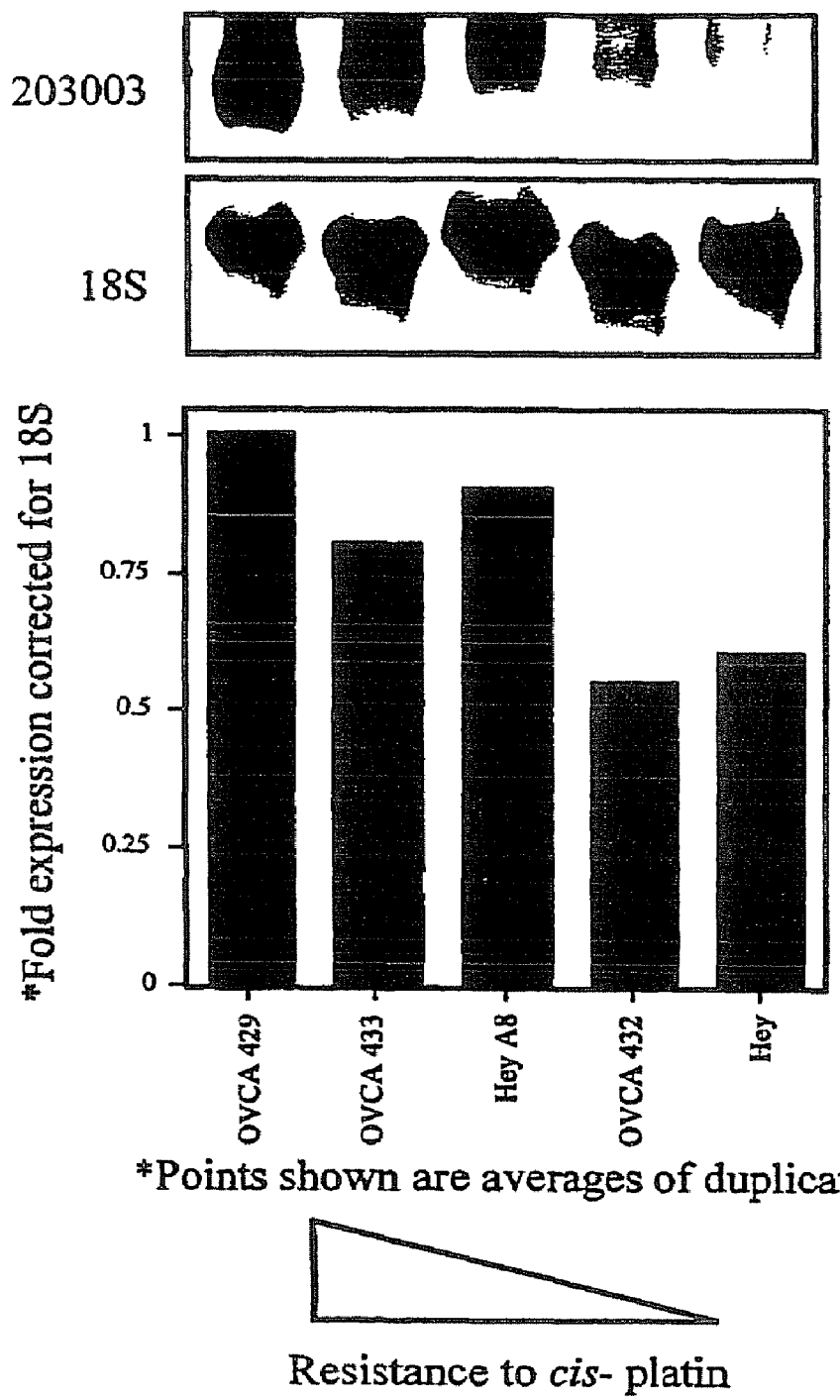
FIG. 26 is a photograph of an autoradiogram showing the results of Northern blot analysis and a graphical representation of the Northern blot results demonstrating that NME4 mRNA was elevated in the chemoresistant cell lines.

NME4 (also known as nm23-h4) is a nucleoside diphosphate kinase that is moderately over-expressed in renal cell carcinoma and strongly over-expressed in colorectal carcinomas (Hayer et al., 2001, *Anticancer Res.* 21:2821-5). NME4 mRNA was elevated in the more resistant cell lines (FIG. 26).

Figure 27:
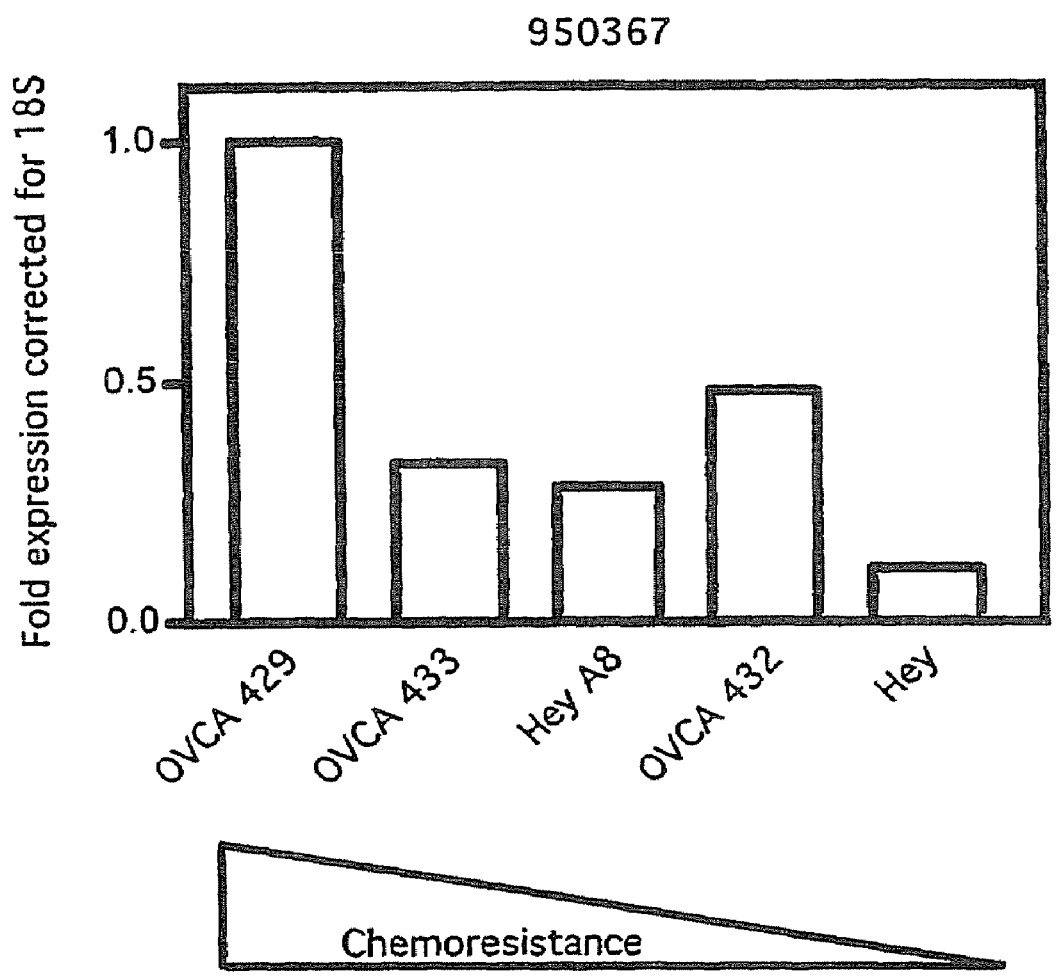
FIG. 27 shows a graphical representation of Northern blot results demonstrating that ADAR1 mRNA was elevated in cell lines that are resistant to cis-platin.

ADAR1: The adenosine-to-inosine RNA editing by adenosine deaminases including ADAR1 results in the creation of alternative splicing sites or alterations of codons and, thus, leads to functional changes in proteins (Wang et al., 2000, *Science* 290:1765). It is also interesting to note that the ADAR1 gene is located on chromosome 1 at 1q21.1-q21.2, in the same frequently rearranged chromosomal region as S100A10 and S100A11 (Pejovic, 1995, *Ann. Med.* 27:73-78). ADAR1 mRNA was elevated in cell lines that are more resistant to cis-platin (FIG. 27).

Figure 28:
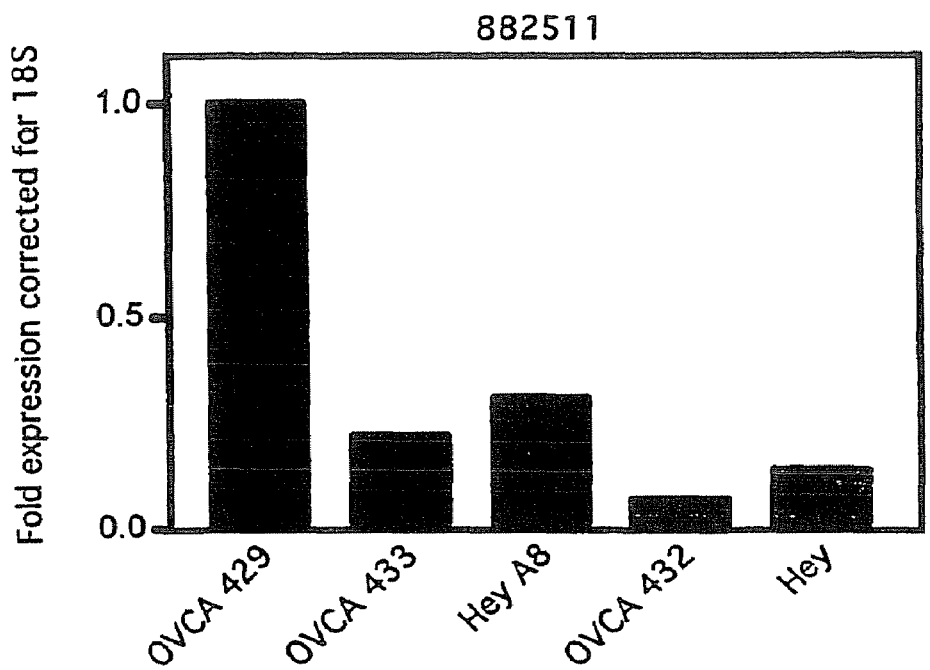
FIG. 28 shows a graphical representation of Northern blot results demonstrating that NBR1 mRNA was elevated in OVCA 429, the most chemoresistant cell line compared to the other cell lines tested.

NBR1: The exact molecular function of NBR1 is unknown. (Those with skill in the art will recognize that the usefulness of a gene in the methods of this invention is not dependent on a detailed or exact notion of the functional properties of a gene.) Mapping studies have revealed that the NBR1 gene lies head-to-head with the BRCA1 gene (Whitehouse et al., 2002, *Eur. J. Biochem.* 269:538-45). NBR1 has no reported association with ovarian cancer. NBR1 mRNA was elevated in the most cis-platin resistant cell line OVCA 429 (FIG. 28).

Figure 29:
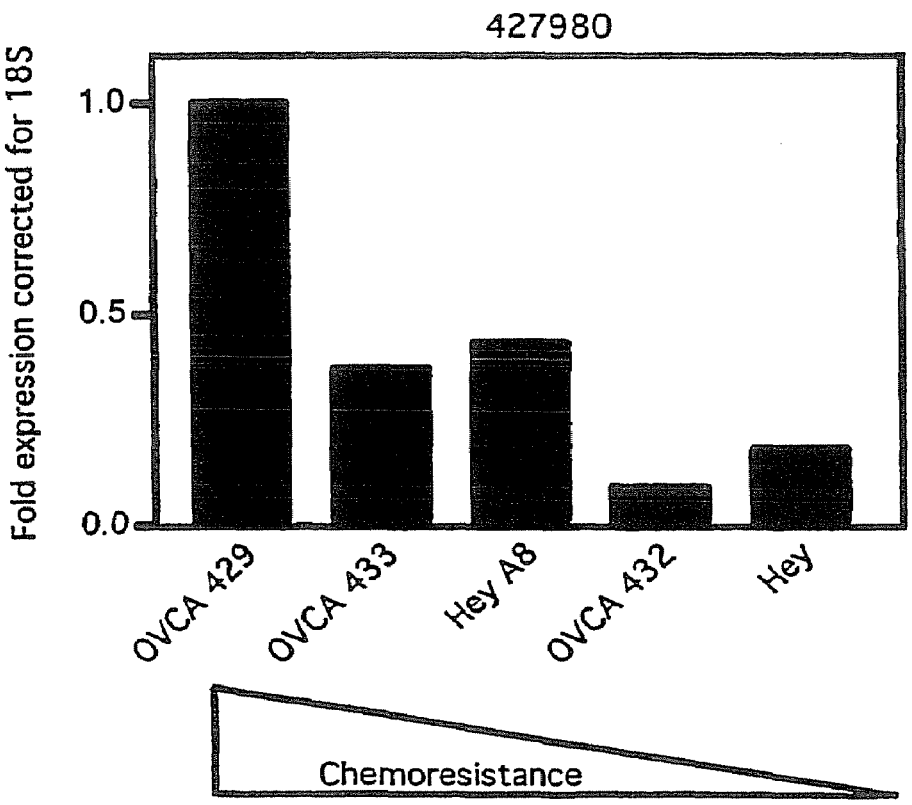
FIG. 29 shows a graphical representation of Northern blot results demonstrating that mRNA for zinc finger protein 262 was elevated in the most cis-platin resistant cell line compared to the other cell lines tested.

Zinc finger protein 262/MYM: A member of a family of genes encoding proteins containing MYM zinc binding motif (Smedley et al., 1999, *Genomics* 60:244-7). This protein has never been associated with ovarian cancer; however, the mRNA for this gene was elevated in the most chemoresistant cell line compared to the other cell lines tested (FIG. 29).

Figure 30:
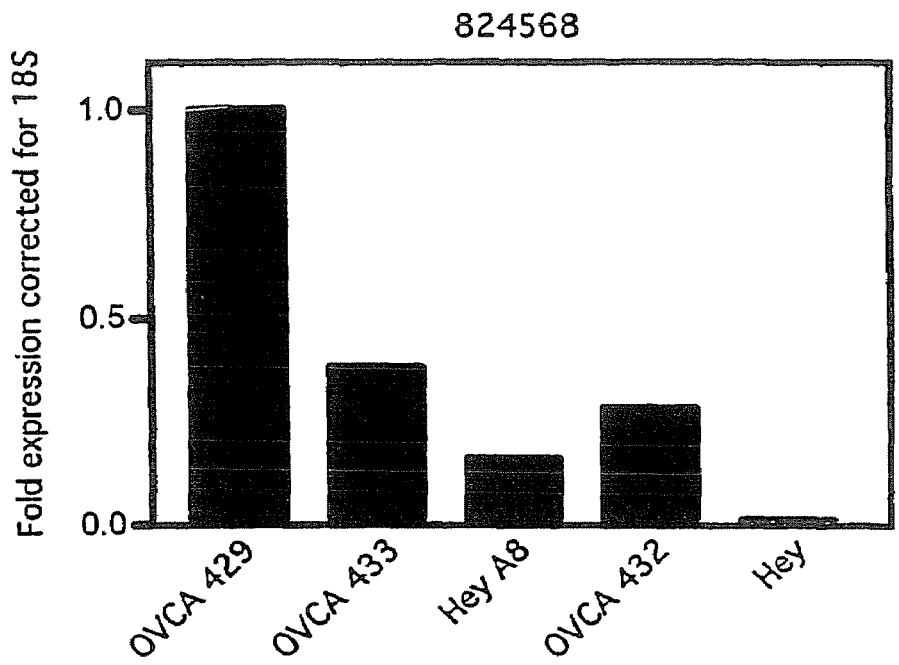
FIG. 30 shows a graphical representation of Northern blot results demonstrating that MRPL4 mRNA was elevated in chemoresistant cell lines.

MRPL4: This gene and its protein have never been associated with ovarian cancer. However, the gene is located on chromosome 19 at 19p13.2, a region frequently rearranged in ovarian cancer (Pejovic, 1995, *Ann. Med.* 27:73-78). MRPL4 mRNA was elevated in chemoresistant cell lines (FIG. 30).

Figure 31:
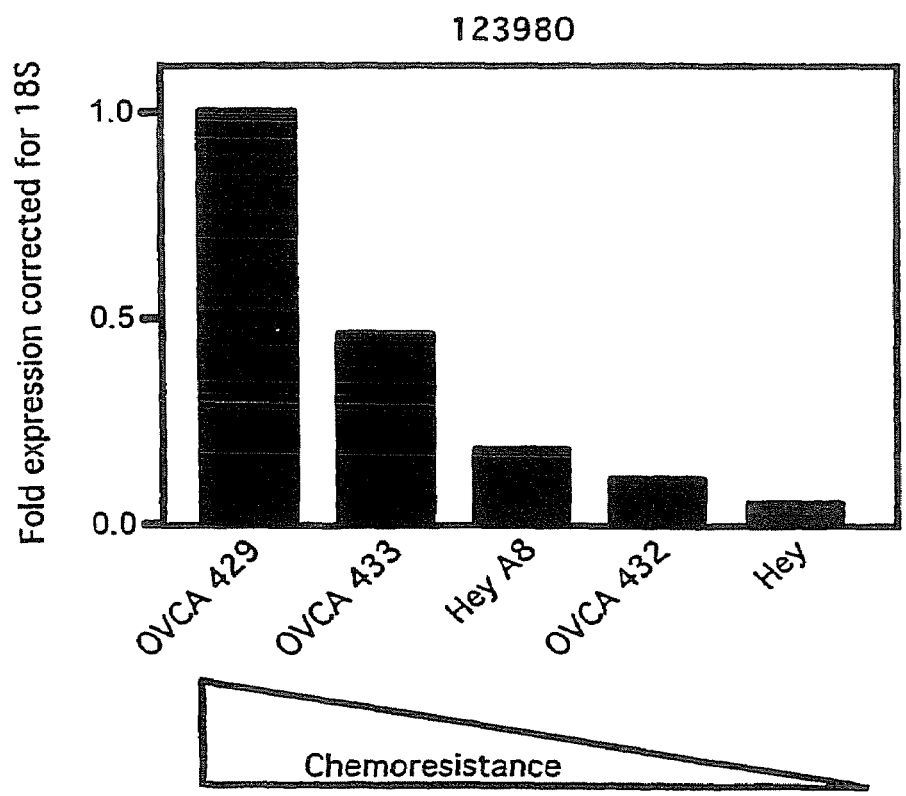
FIG. 31 shows a graphical representation of Northern blot results demonstrating that HYA22 mRNA was elevated in chemoresistant cell lines compared to chemosensitive ones.

HYA22: This gene and its protein have never been associated with ovarian cancer. However, the gene is located on chromosome 3 at 3p21.3, a region associated with chromosomal rearrangements in ovarian cancer (Pejovic, 1995, *Ann. Med.* 27:73-78; Protopopov et al., 2003, *Cancer Res.* 63:404-12; Senchenko et al., 2003, *Oncogene* 22:2984-92). HYA22 mRNA was elevated in cell lines more resistant to cis-platin compared to the more sensitive cell lines (FIG. 31).

Figure 32:
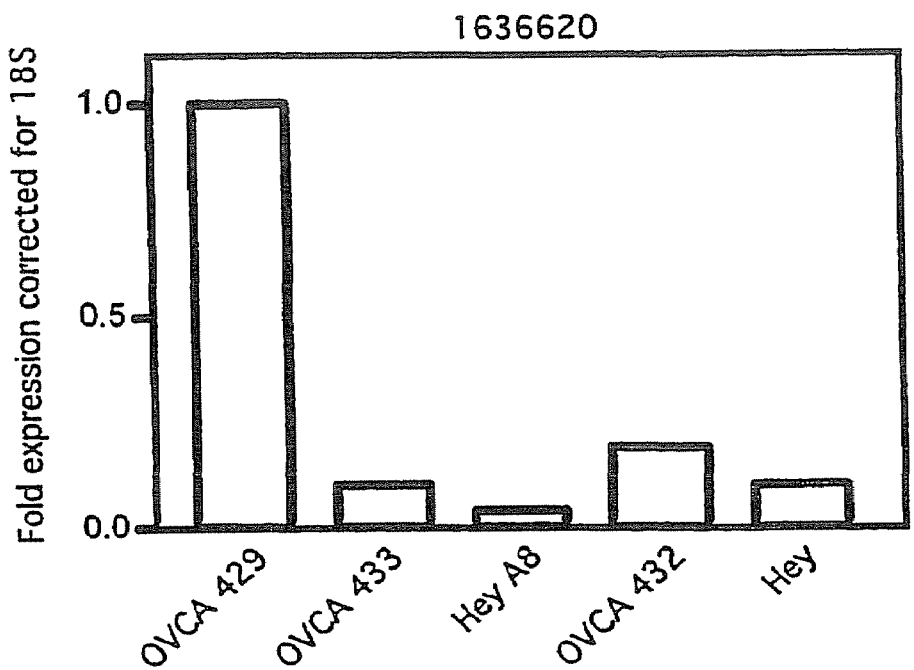
FIG. 32 shows a graphical representation of Northern blot results demonstrating that the mRNA for vinexin β was elevated in chemoresistant cell lines.

Vinexin β: Also known as SCAM-1, this gene encodes an adapter protein belonging to a family of proteins also including Vinexin β, CAP/Ponsin and ArgBP2 (Kioka et al., 2002, *Cell Structure and Function* 27:1-7). Vinexin was not known in the prior art to be linked to ovarian cancer. Vinexin β mRNA was elevated in chemoresistant cell lines (FIG. 32).

Figure 33:
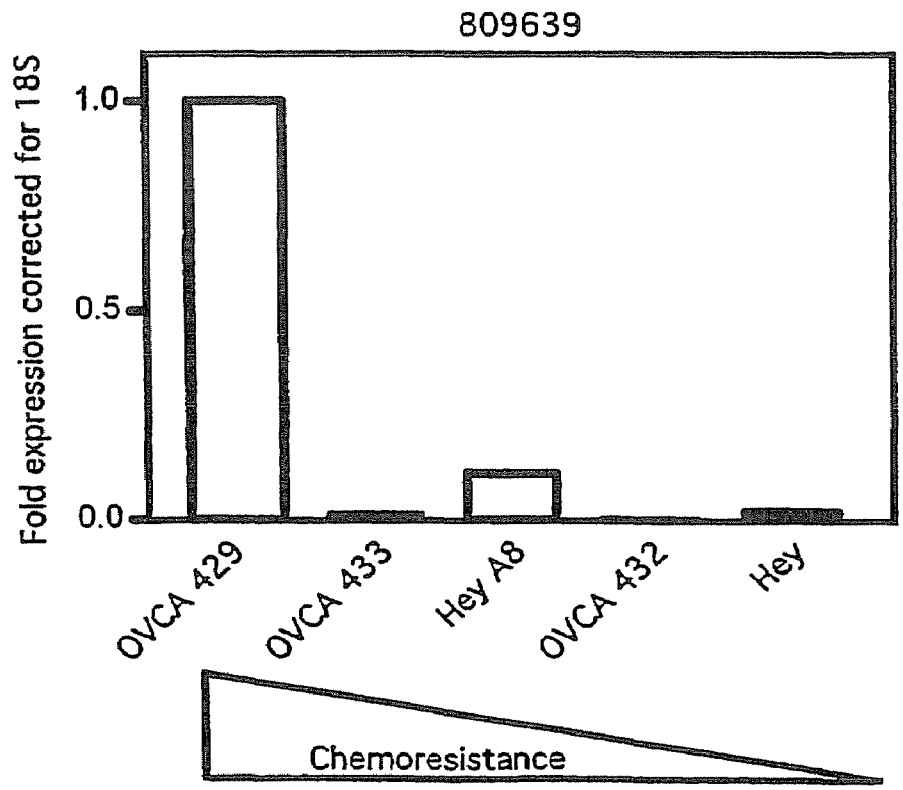
FIG. 33 shows a graphical representation of Northern blot results demonstrating that the mRNA for G-CSFR was elevated in chemoresistant cell lines.

G-CSFR: Granulocyte colony-stimulating factor receptor (G-CSFR) is almost universally expressed in primary ovarian cancer. The expression of its ligand, however, G-CSF was found in the same cells in only half of the cases studied, suggesting the presence of an autocrine system (Savarese et al., 2001, *Cancer Letters* 162:105-15). In another third of the cases studied G-CSF was found exclusively in the stroma, suggesting a paracrine system may be present, in which mesenchymal cells may provide the ligand to cancerous cells expressing the receptor (Savarese et al., 2001, *Cancer Letters* 162:105-15). A preliminary, retrospective evaluation suggested that overall survival is worse in patients expressing the paracrine loop alone as compared to patients whose ovarian cancer expressed an autocrine axis (Savarese et al., 2001, *Cancer Letters* 162:105-15). G-CSF and its receptor can also be co-expressed in normal ovaries and some benign ovarian neoplasms. G-CSFR mRNA was elevated in chemoresistant cell lines (FIG. 33).

Figure 34:
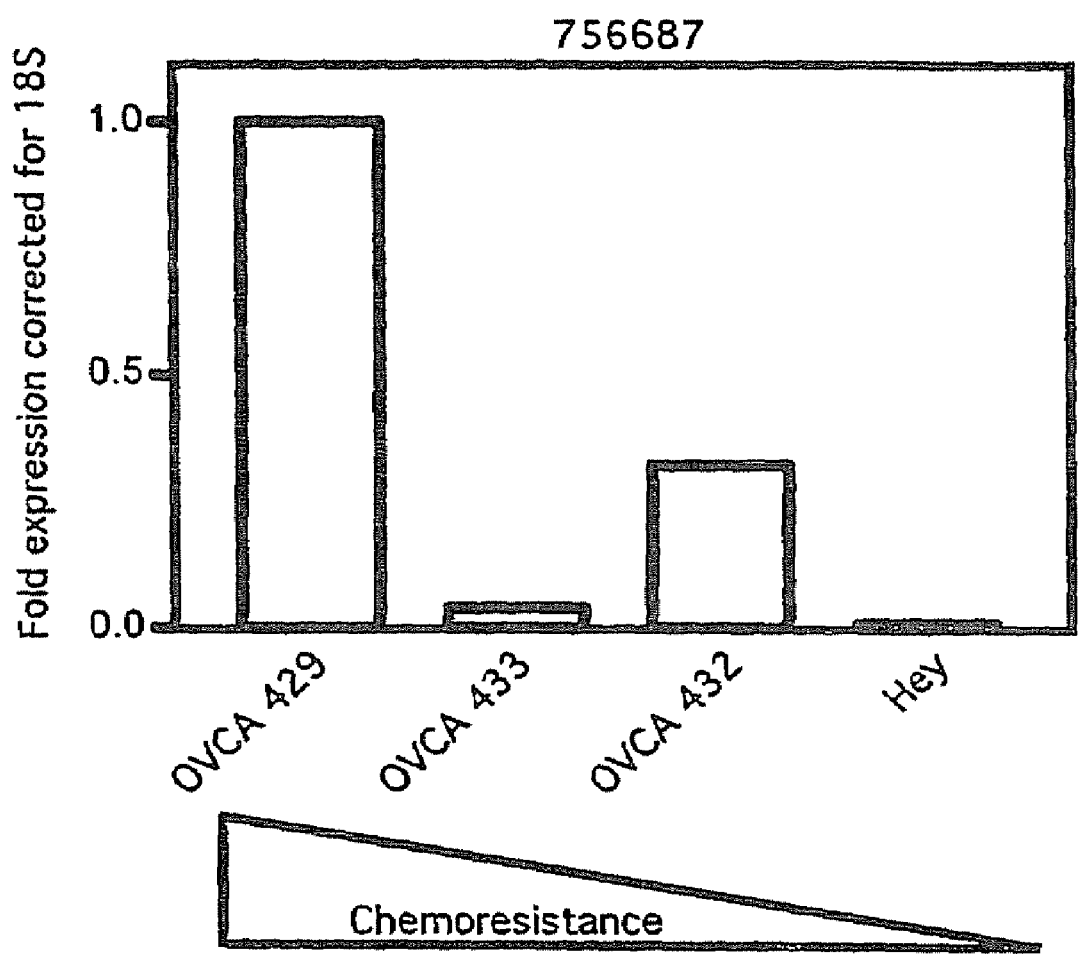
FIG. 34 shows a graphical representation of Northern blot results demonstrating that SRB1 mRNA was elevated in chemoresistant cell lines.

SRB1: Also known as CLA-1, this gene encodes a receptor that recognizes both negatively charged liposomes and apoptotic cells. Tumor cells have been reported to participate in the uptake and removal of apoptotic cells and bodies (Fukasawa et al., 1996, *Exp. Cell Res.* 222:246-50). The biological significance of these observations is poorly understood. There has been no prior disclosure of links between the expression of SRB1 and ovarian cancer. SRB1 mRNA was elevated in chemoresistant cell lines (FIG. 34).

Figure 35:
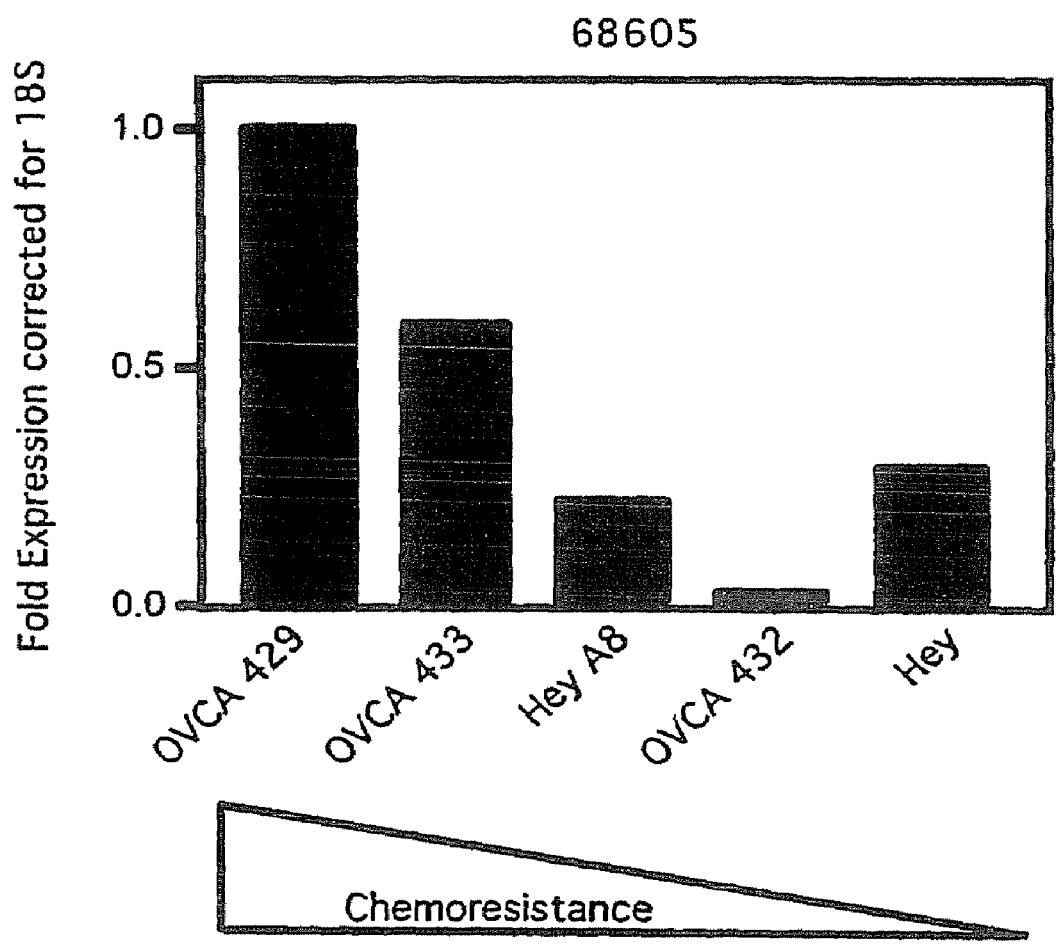
FIG. 35 shows a graphical representation of Northern blot results demonstrating that IGFBP-7 mRNA was elevated in chemoresistant cell lines.

IGFBP-7: A more recently identified member of the IGF binding proteins, this protein binds IGF-I and IGF-II with a relatively low affinity (Oh, 1998, *Breast Cancer Res. Treat.* 47:283-93). IGFBP-7 mRNA was elevated in chemoresistant cell lines (FIG. 35).

Figure 36:
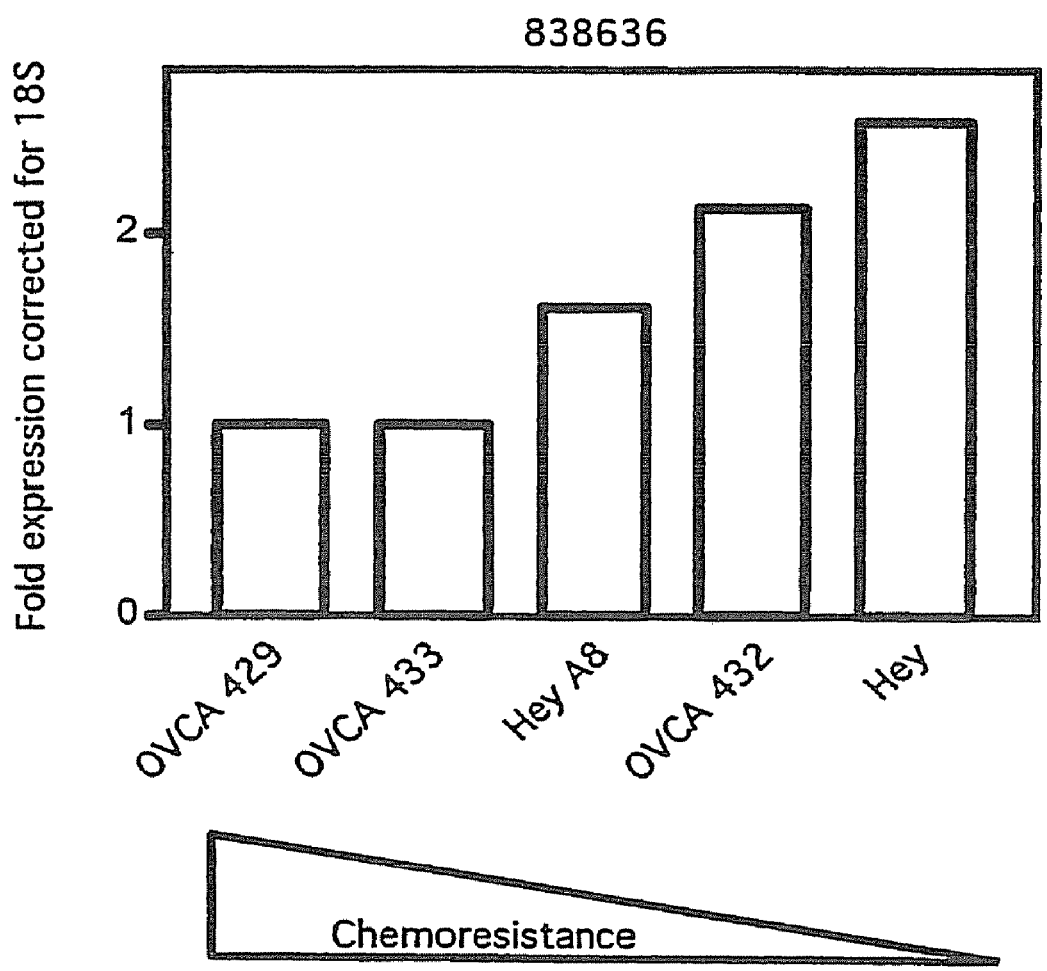
FIG. 36 shows a graphical representation of Northern blot results demonstrating that RAB22A mRNA was decreased in chemoresistant cell lines and is elevated in the more responsive cell lines.

RAB22A belongs to the RAB subfamily of Ras proteins (Kauppi et al., 2002, *J. Cell Science* 115:899-911). RAB22A mRNA was decreased in chemoresistant cell lines and was elevated in cell lines more responsive to cis-platin (FIG. 36).

Figure 37:
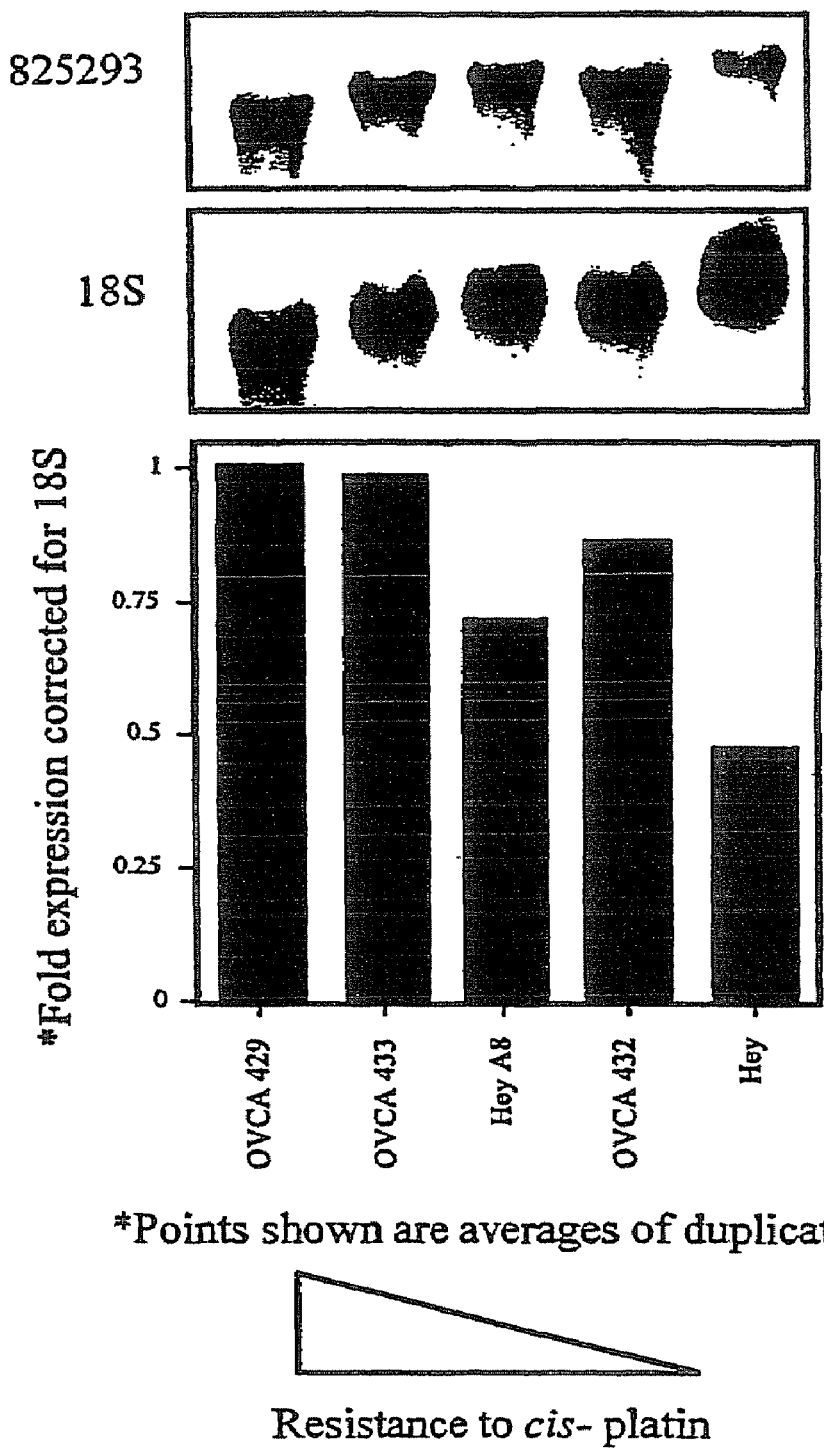
FIG. 37 shows a graphical representation of Northern blot results demonstrating that expression of KIAA0082 mRNA was elevated in chemoresistant cell lines.

KIAA0082: KIAA0082 is a full-length gene for which there is no published information. mRNA expression for this gene was elevated in cell lines resistant to cisplatin (FIG. 37).

Figure 38:
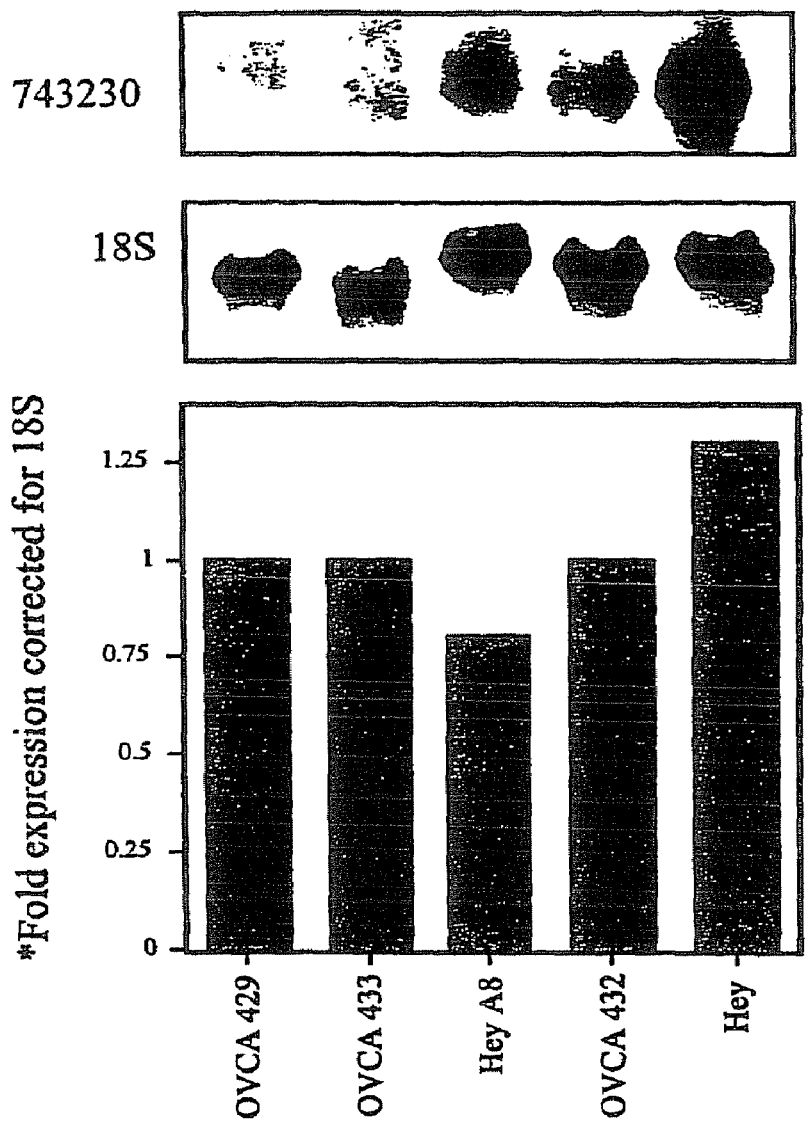
FIG. 38 shows a Northern blot analysis and a graphical representation of results demonstrating that the mRNA for NCOR2 was reduced in cis-platin resistant cell lines compared to sensitive ones.
Figure 38:

NCOR2: This is a co-repressor protein closely related to SMRT with a specific interaction domain for the thyroid hormone receptor (Jepsen and Rosenfeld, 2002, *J. Cell Science* 115:689-98). mRNA expression for this gene was reduced in chemoresistant cell lines compared to cell lines sensitive to cis-platin (FIG. 38).

Figure 51:
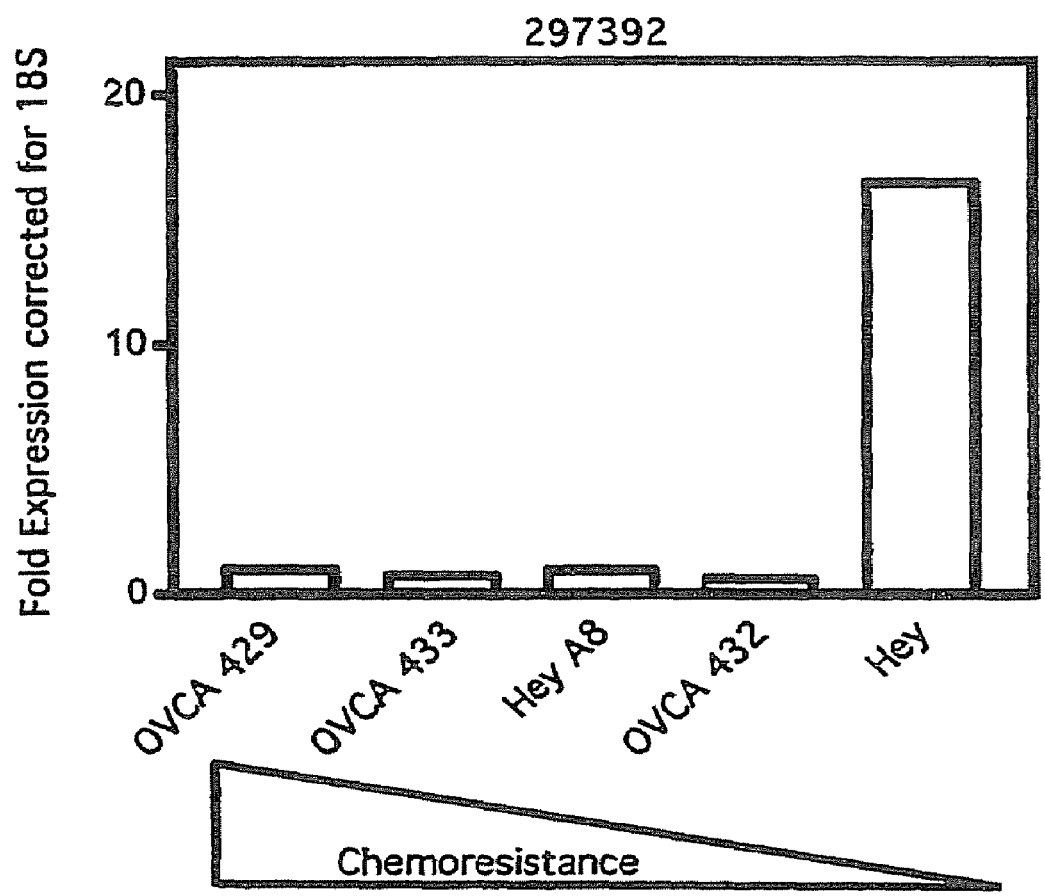
FIG. 51 shows a graphical representation of Northern blot results demonstrating that MT1 mRNA was highly elevated in the cell line most sensitive to cis-platin (Hey).

MT1: The precise physiological role of Metallothionein 1 L (MT1) is unknown, however, previous studies have reported that MT levels are elevated in cis-platin resistant human ovarian carcinoma cells (Andrews and Howell, 1990, *Cancer Cells* 2:35-43) and cells transfected with the MT gene became resistant to cis-platin (Nakano et al., 2003, *Anticancer Res.* 23:299-304). MTs are thought to function in sequestering cis-platin in the cytoplasm, therefore increasing the cells ability to resist the drug (Nakano et al., 2003, *Anticancer Res.* 23:299-304). Paradoxically, the level of MT1 mRNA appeared to be highly elevated in cells most sensitive to cis-platin (Hey) (FIG. 51).

Figure 52:
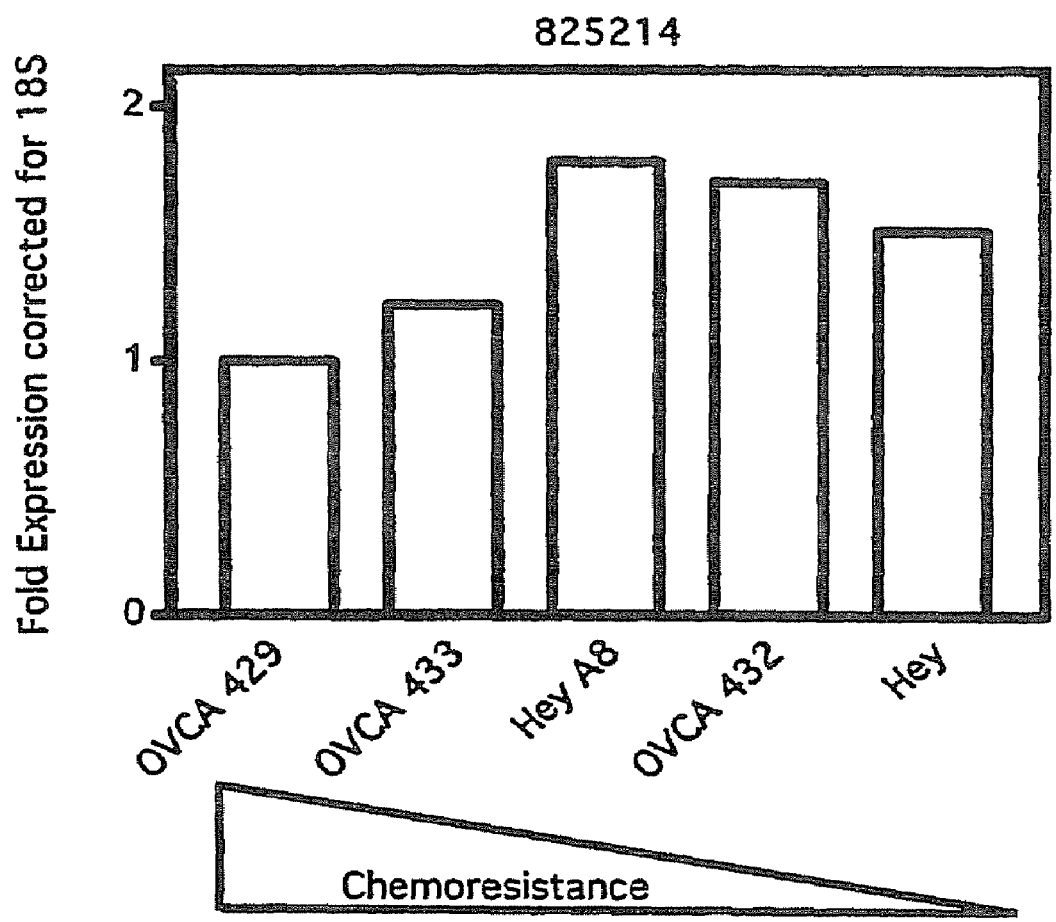
FIG. 52 shows a graphical representation of Northern blot results demonstrating that MPP10 mRNA was increased with increased sensitivity to cis-platin.

MPP10: M-phase phosphoprotein (MPP10) is a mostly cytoplasmic protein but can be secreted and is a component of the human U3 small nucleolar ribonucleoprotein. The majority of this protein co-localizes with fibrillarin (Baserga et al., 1997, *Nucleic Acids Symp. Ser.* 36:64-7), and is involved in rRNA processing. No association has been reported for this gene or its product with ovarian cancer. MPP10 expression levels increased with increased sensitivity to cis-platin (FIG. 52).

Example 3

In Vitro Testing of SPARC as Therapeutic Target

SPARC was expressed at the highest levels in the most cis-platin resistant cell line (OVCA 429) compared to the other cell lines tested (FIG. 4). This protein is known in the art to be a calcium-binding glycoprotein that modulates adhesion and can play an important role in tissue remodeling and angiogenesis promoting tumor progression and invasiveness (Ledda et al., 1997, *J. Invest. Dermatol.* 108:210-214).

SPARC expression was tested in human Ascites fluid samples obtained from an individual before cyto-reductive surgery and then 9 months following surgery when the patient's tumor had recurred (FIG. 5; the two transcripts observed for SPARC arise due to differential polyadenylation; Ledda et al., 1997, *J. Invest. Dermatol.* 108:210-214). SPARC expression levels after surgery were greatly increased and correlated with a poor outcome for this patient. This observation was also consistent with findings made by other groups studying other forms of solid cancers (Golembieski et al., 1999, *Int. J. Dev. Neurosci.* 17:463-72; Briggs et al., 2002, *Oncogene* 21:7077-91; Huang and Wang, 2001, *TRENDS in Molecular Medicine* 7:355; Lollike et al., 2001, *J. Biol. Chem.* 276:17762-9), indicating that increased SPARC expression can be predictive of chemotherapeutic treatment success and disease progression in other types of solid cancer in addition to ovarian cancer.

In order to test whether lowering SPARC protein expression levels in OVCA 429, the most resistant ovarian cancer cell line, would reduce its ability to resist cis-platin, three siRNAs were designed directed against different regions of the SPARC message. The SPARC siRNAs used were:

```
#1 Target Sequence:
AATCC TGT CCA GGT GGA AGT A;      (SEQ ID NO: 1)

#2 Target Sequence:
AAGCT CCA CCT GGA CTA CAT C;      (SEQ ID NO: 2)
and

#3 Target Sequence:
AATGA CAA GTA CAT CGC CCT G.      (SEQ ID NO: 3)
```

The siRNA experiments described herein were conducted using the siPORT Lipid protocol (Ambion). Cells were plated 24 hours before transfection in MEMα media containing 10% FBS, so that cells were 30-70% confluent at the time the experiment was performed. The siPORT and siRNA complexes were prepared using media without FBS or antibiotics. For siPORT, 4 microliters per well for six well plates and 0.5 microliter per well for 96 well plates were added to media, mixed by vortexing, and incubated at room temperature for 25 minutes. For siRNA, 1-25 nM (12.5 nM is normally used) concentration of siRNA was used, diluted in media. The siPORT was added to the siRNA mixture, mixed gently, and incubated at room temperature for 20 minutes. After the cells were washed with serum free media, cells were added to the plates (where 96 well plates were used, cells were plated at a density of $4.5 \times 10^4$; where 6 well plates were used, cells were plated at a density of $1-5 \times 10^5$). The siPORT/siRNA complex was added to each plate/well and the plates were rocked gently to distribute complex over cell surface. After incubating for 4 hours under normal cell culture conditions, additional media containing 10% FBS was added to the cells. After 48 hours, total RNA was extracted.

Cells were transfected with the siRNA constructs following instruction from the supplier (Ambion). For 6-well plates, 12.5 nM siRNA/well was used for transfection. The $OD_{260}$ readings of siRNA were performed in duplicate at a 1:100 dilution. The readings were averaged, then multiplied by the dilution factor and then by multiplied by 40 (the $OD_{260}$ of 1 is equal to 40 μg/ml of RNA) to get the final concentration of siRNA in μg/ml. The number was divided by 14 (the number of μg of RNA in 1 nmole of an average 21mer dsRNA) to get final siRNA concentration in μM, and then converted so that the concentration was presented in nM.

Figure 48:
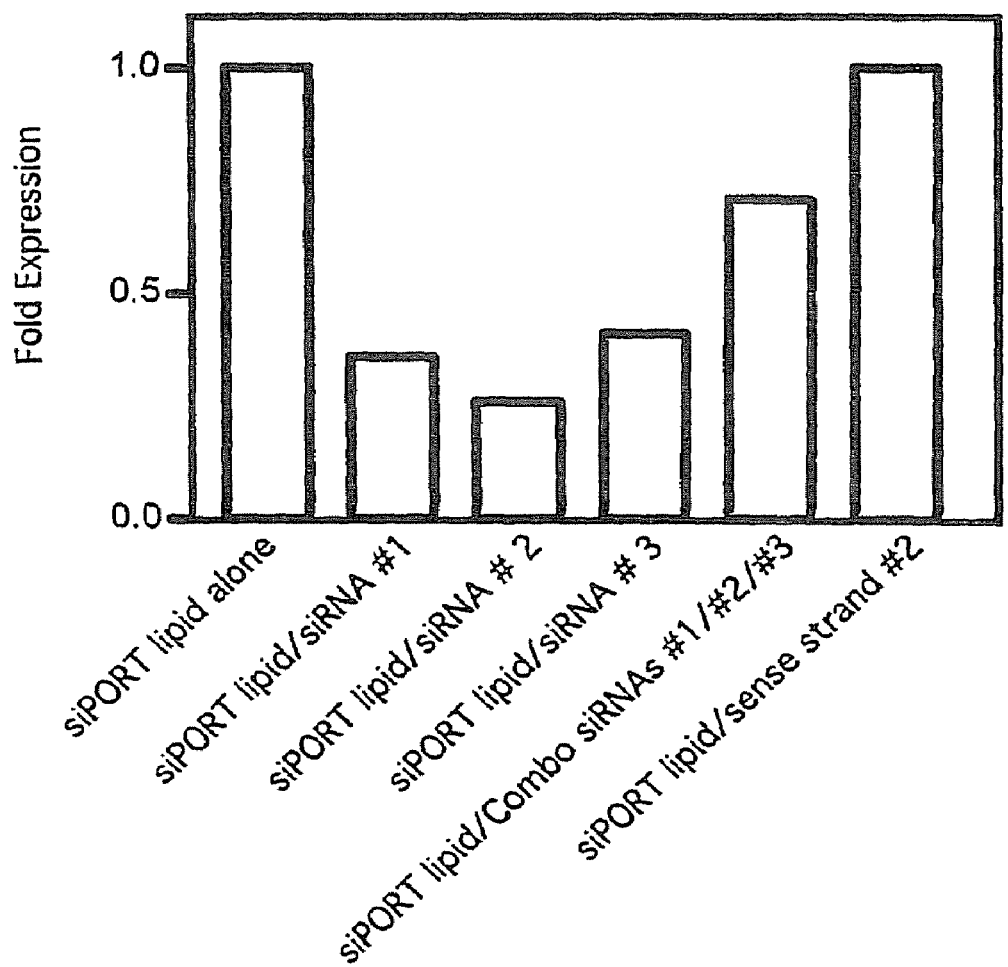
FIG. 48 is a graph representing the results of quantitative real-time PCR analysis of SPARC expression in OVCA 429 cells transfected with the siRNAs shown in FIG. 47.

The results of these studies are shown in FIG. 48. All three siRNAs decreased the level of SPARC mRNA in these cells. Cells treated with siPORT only or with the sense strand of siRNA #2 alone did not show any significant reduction in SPARC mRNA expression. A combination treatment, which included all three siRNAs together, did have some effect, however (FIG. 48).

Figure 49:
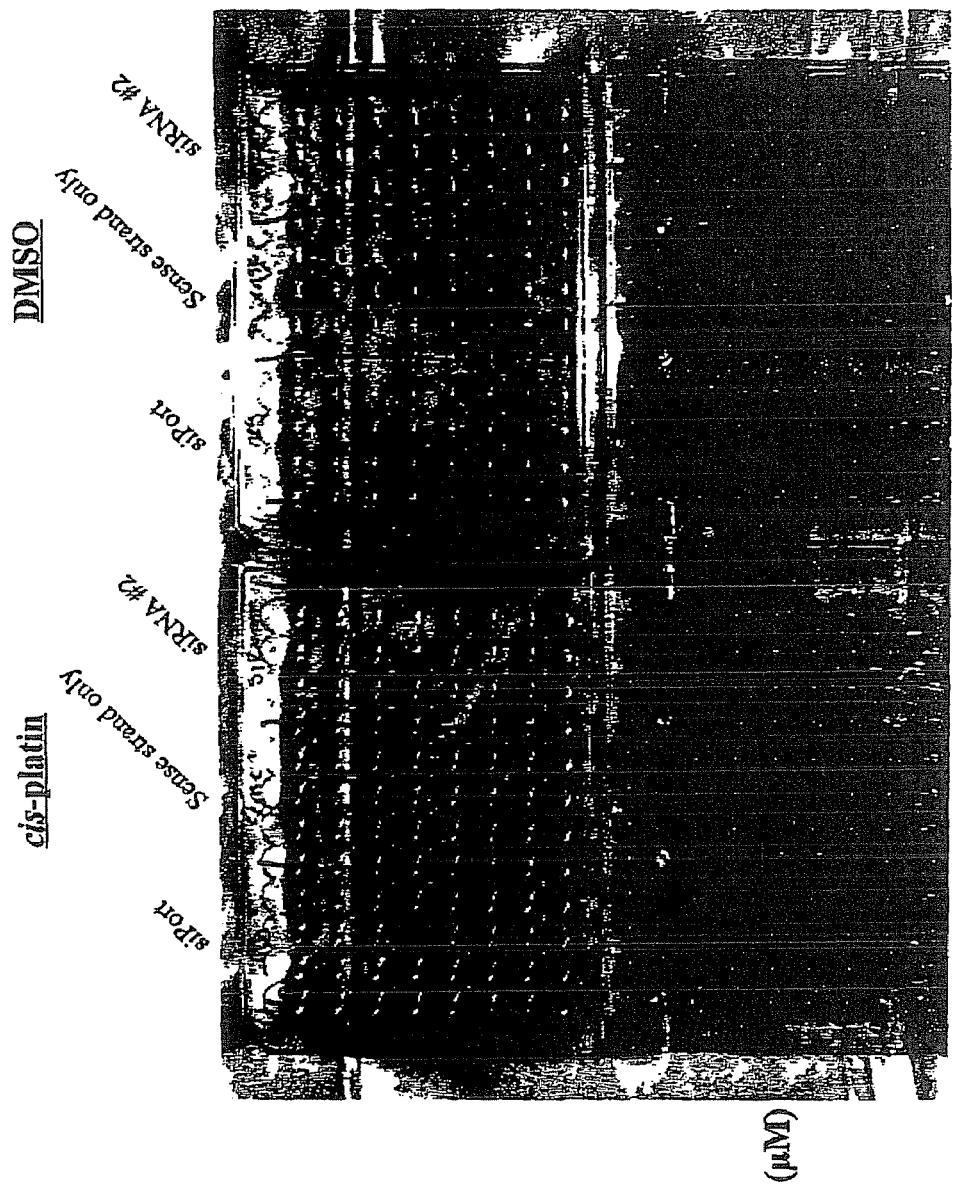
FIG. 49 is a photograph of 96-well plates containing OVCA 429 cells after performing the MTT assay to determine the effects of cis-platin on OVCA 429 cells in the presence of SPARC siRNA #2.
Figure 50:
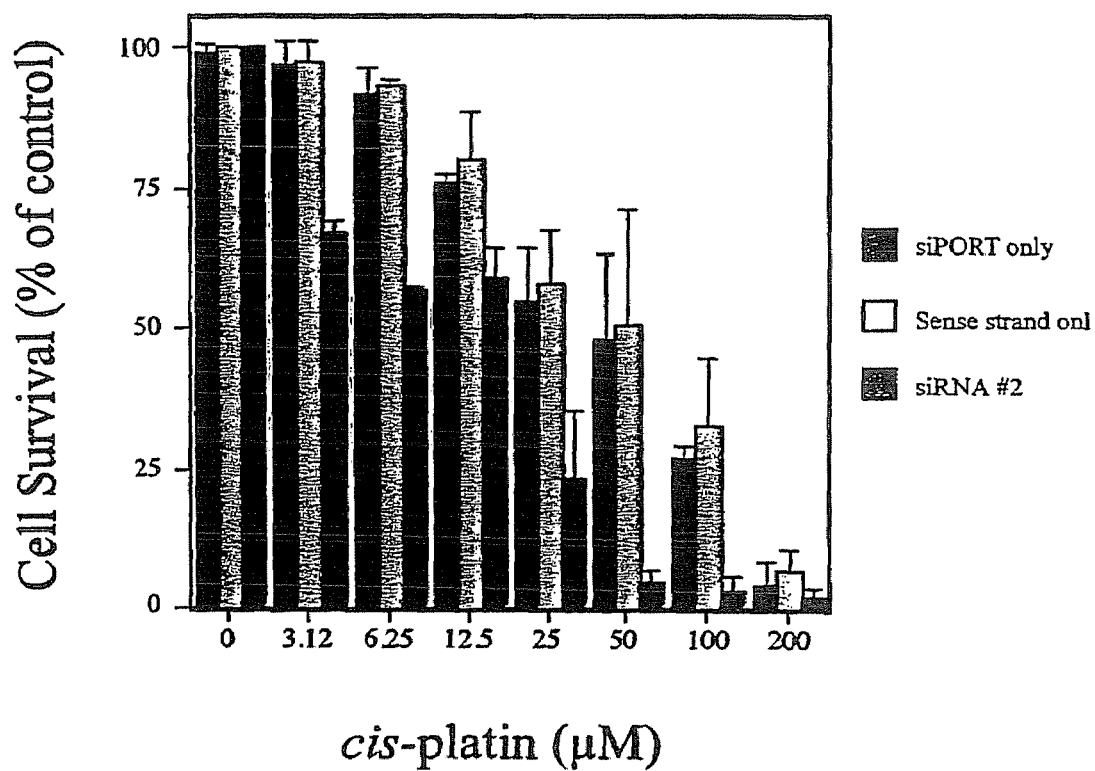
FIG. 50 is a graph representing the effects of siRNA-mediated reduction of SPARC gene expression on cis-platin sensitivity in OVCA 429 cells.

The ability of OVCA 429 cells to resist cis-platin in the presence of the SPARC siRNAs was also investigated. The cells were treated with siPORT alone or transfected with either the sense strand of siRNA #2 alone or the complete siRNA #2. The cells were allowed to recover for 48 hours after transfection and then treated with increasing concentrations of cis-platin or the corresponding concentrations of DMSO as a control. The cells were exposed to the drug for 24 hours after which the drug was removed and the cells were allowed to recover for an additional 72 hours. The effect of this treatment on cell viability was then assessed by an MTT assay. The results are shown in FIG. 49; FIG. 50 shows these results after quantitation of the effects on the cells. The data suggested that treating the cells with the complete siRNA #2 prior to exposure to cis-platin reduced their resistance level by half (IC$_{50}$~25-50 μM for controls treated with siPORT only or sense strand only to an IC$_{50}$ of ~12.5 μM after treating with siRNA #2).

The results of these experiments indicated that SPARC is a therapeutic target and marker for ovarian cancer.

Example 4

In Vitro Testing of MetAP2/p67 as Therapeutic Target

MetAP-2/p67 is a bifunctional protein with both functions being important for cell growth (Li and Chang, 1996, *Biochem. Biophys. Res. Commun.* 227:152-9; Wu et al., 1993, *J. Biol. Chem.* 268:10796-10801). In one role, the protein binds to eukaryotic initiation factor 2 (eIF-2) and inhibits its phosphorylation, and in the other role its C-terminus domain has enzymatic activity catalyzing hydrolysis of N-terminal methionines from a number of cellular proteins (Wu et al., 1993, *J. Biol. Chem.* 268:10796-10801). Phosphorylation of eIF-2 alters its translational repertoire allowing different messages to be translated at different phosphorylation states. Additionally, the methionine aminopeptidase activity is important generally for protein function and failure to remove N-terminal methionines often produces inactive proteins (Li and Chang, 1996, *Biochem. Biophys. Res. Commun.* 227:152-9).

Fumagillin, from *Aspergillus fumigatus*, and its synthetic analogue TNP-470, covalently binds to and inhibits the methionine aminopeptidase activity of MetAP-2 but not that of the closely related MetAP-1 (Griffith et al., 2998, *Proc. Natl. Acad. Sci. USA* 95:15183-8). It is also important to note that treatment of several different cell types with fumagillin resulted in increased expression of MetAP-2 (Wang et al., 2000, *J. Cell. Biochem.* 77:465-73); it is thought that the cell adapts to a loss of function of MetAP-2 by increasing its level of expression.

Figure 8:
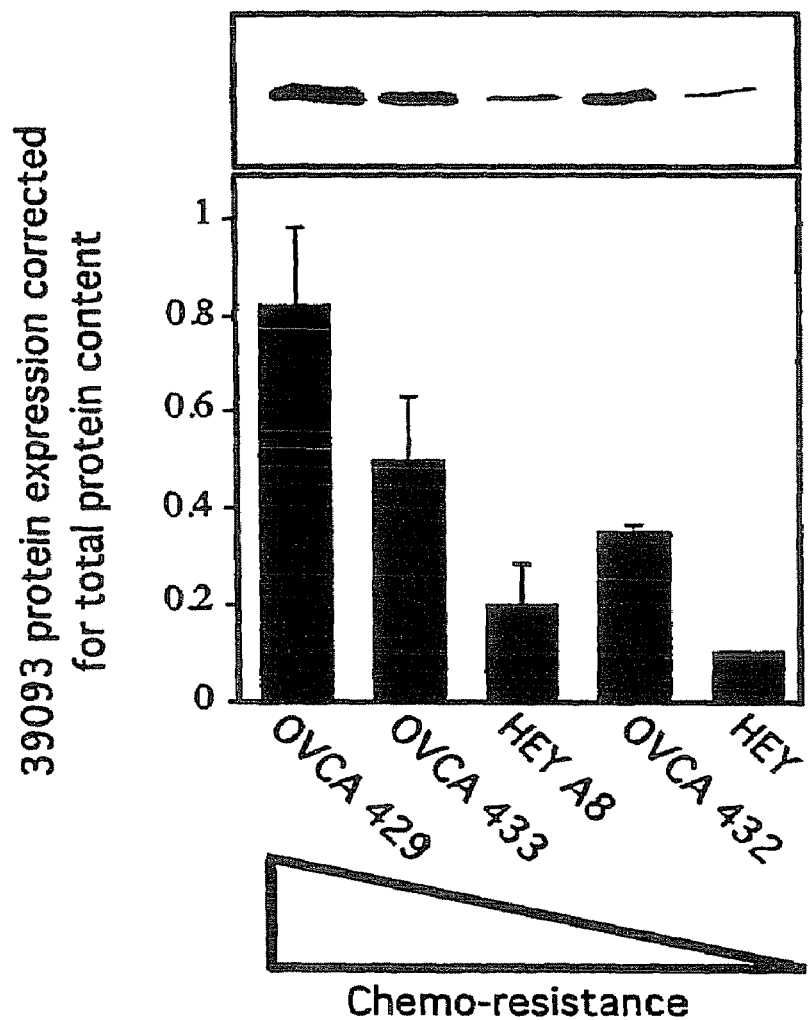
FIG. 8 is a photograph of an autoradiogram showing the results of Western blot analysis and a graphical representation of the Western blot results demonstrating that expression of MetAP2 protein was elevated in the highly chemoresistant cell line OVCA 429 and down-regulated in the Hey cell line, which is sensitive to cis-platin treatment.
Figure 9:
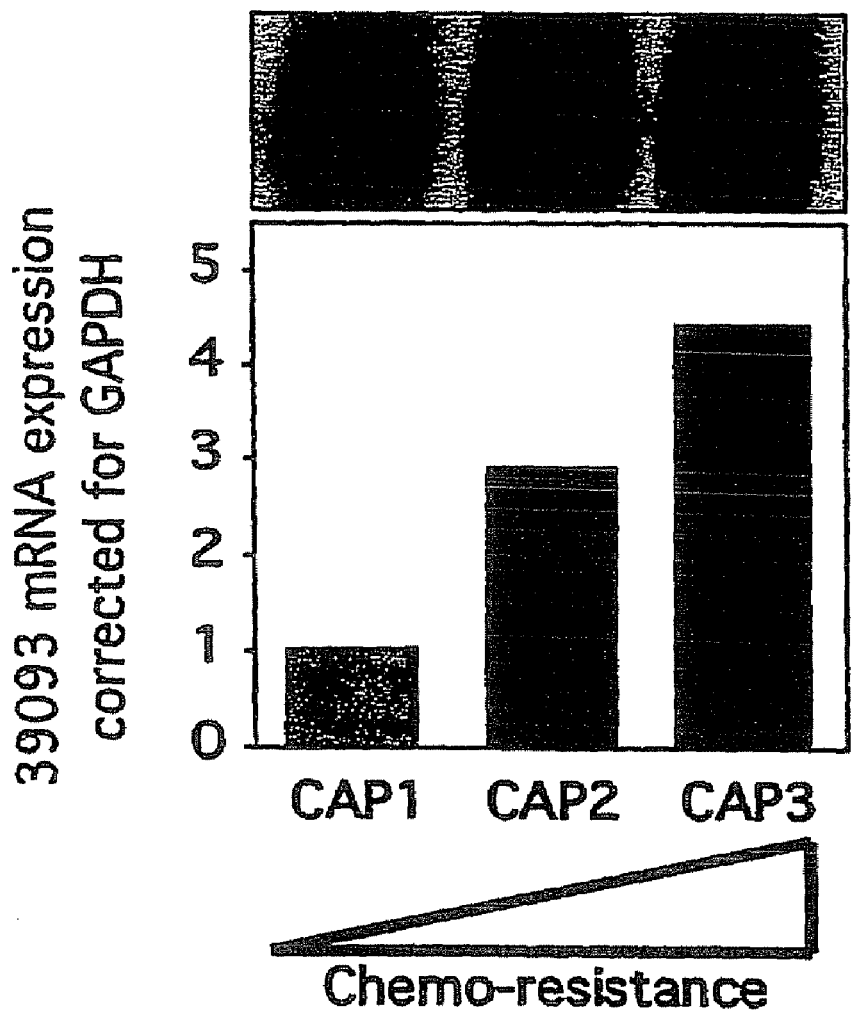
FIG. 9 is a photograph of an autoradiogram showing the results of Northern blot analysis and a graphical representation of the Northern blot results demonstrating expression of MetAP2 mRNA in tissue samples obtained from three patients with different levels of resistance to cis-platin-based chemotherapy. MetAP2 is most elevated in the sample from the patient having the most resistant tumor (CAP3) compared to patients with intermediate (CAP2) and low (CAP1) levels of resistance to chemotherapy.

The experiments described herein suggested that OVCA 429 expressed approximately 7 times more MetAP-2 than the cell line most sensitive to cis-platin, Hey (FIG. 8). Northern blot analysis also confirmed that the levels of MetAP-2 expression are also elevated in patients that are clinically more resistant to cis-platin-based chemotherapy. FIG. 9 shows that the level of MetAP-2 mRNA was approximately 3 fold higher in the most resistant patient (CAP3) than in the least resistant patient (CAP1). A patient with an intermediate level of resistance to cis-platin-based chemotherapy also exhibited an intermediate level of MetAP-2 mRNA.

Figure 40:
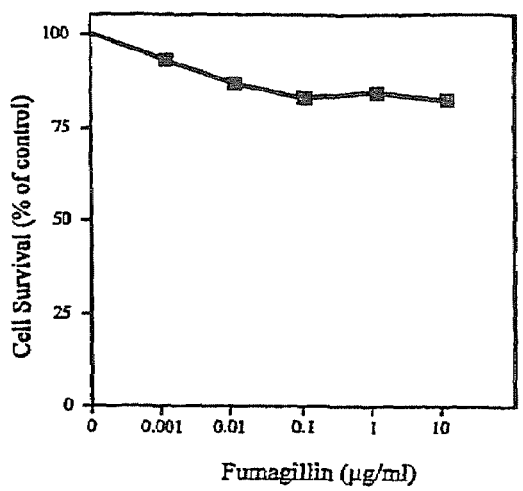
FIG. 40 (upper panel) depicts a graph showing the effects of increasing concentration of fumagillin on OVCA 429 cell survival after 4 hours of exposure to the drug. The bottom panel depicts a graph showing that there was an enhancement of the effect of cis-platin in the presence of 0.1 μg/ml fumagillin but not when the cells were treated with cis-platin in the presence of 10 μg/ml fumagillin for 4 hours.
Figure 40:
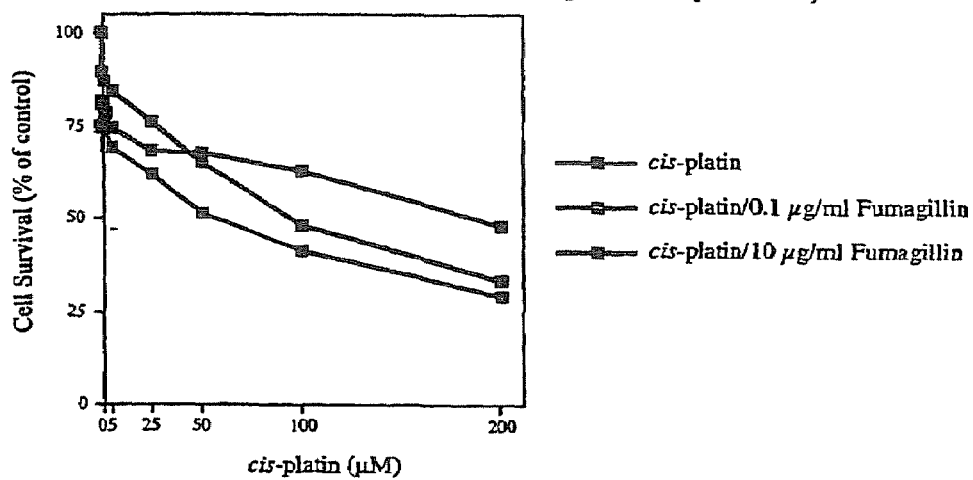
Figure 41:
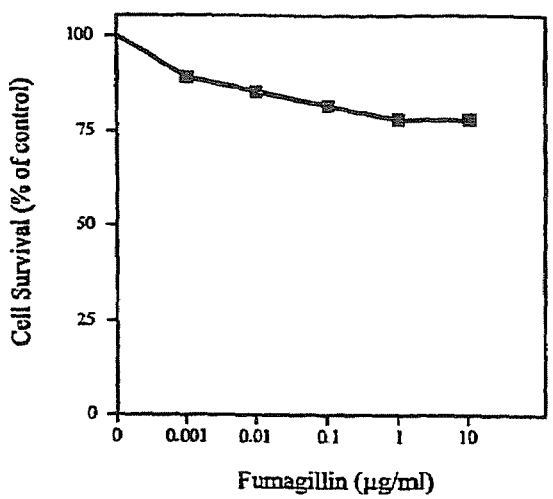
FIG. 41 (upper panel) depicts a graph showing the effects of increasing concentration of fumagillin on OVCA 429 cell survival after 8 hours of exposure to the drug.
Figure 41:
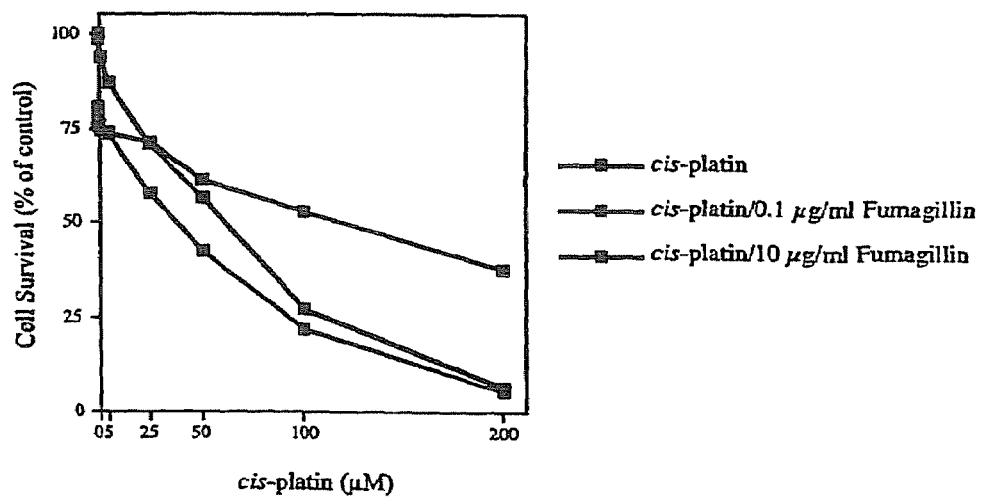
Figure 42:
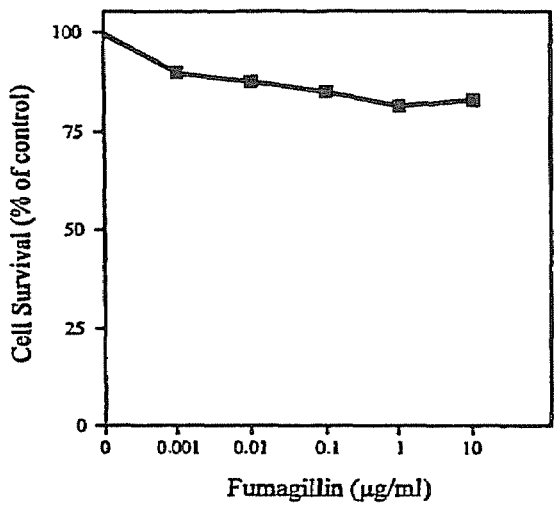
FIG. 42 (upper panel) depicts a graph showing the effects of increasing concentration of fumagillin on OVCA 429 cell survival after 24 hours of exposure to the drug.
Figure 42:
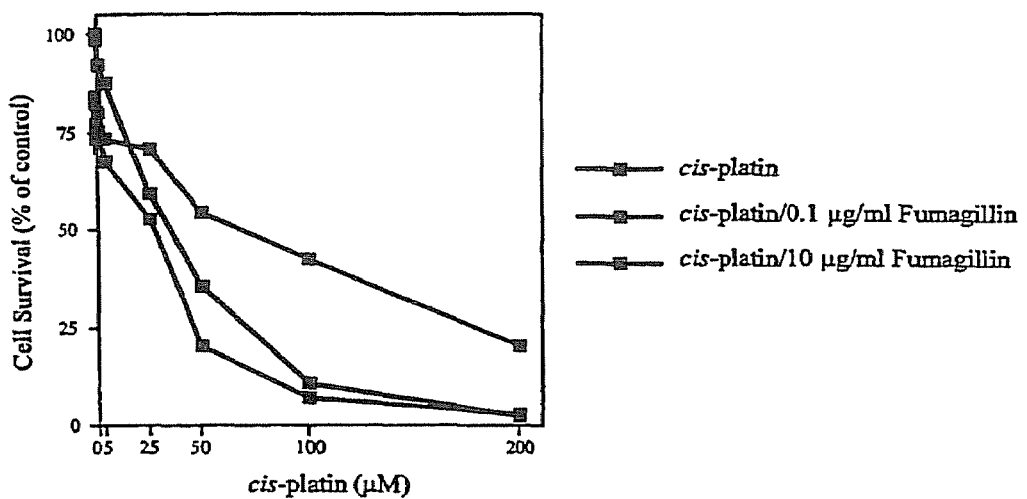

MTT-based assays were conducted in which OVCA 429 cells were treated with fumagillin alone, cis-platin alone and with combinations of different concentrations of cis-platin and fumagillin for 4, 8 and 24 hours. The results are shown in FIGS. 40, 41 and 42. FIG. 40 (top panel) shows the effects of increasing concentration of fumagillin on OVCA 429 cell survival. Some cell death was observed but up to 80% of the cells survived even at very high concentrations of fumagillin. Treating the cells with cis-platin alone (bottom panel) resulted in an IC$_{50}$ of approximately 100 μM cis-platin. The presence of 0.1 μg/ml fumagillin in addition to increasing levels of cis-platin reduced the IC$_{50}$ to approximately 50 μM. However, treating the cells with cis-platin in the presence of 10 μg/ml fumagillin resulted in enhanced cell survival with an IC$_{50}$ of approximately 200 μM.

Regardless of the length of incubation time, there was an enhancement of the effect of cis-platin in the presence of 0.1 μg/ml fumagillin but the opposite effect when the cells were treated with cis-platin in the presence of 10 μg/ml fumagillin (FIGS. 41 and 42). These observations suggested that at low levels of fumagillin, a favorable balance is achieved and the drug acts synergistically with cis-platin leading to the death of more cells.

Figure 43:
FIG. 43 is a schematic representation of three siRNAs (#1, SEQ ID NO: 4; #2, SEQ ID NO: 5; and #3, SEQ ID NO: 6) designed to target different regions of the MetAP-2 messenger RNA.

Three siRNAs were designed to target different regions of the MetAP-2 message (FIG. 43), to determine the effect of inhibiting MetAP-2 expression. The MetAp-2 siRNAs were:

```
#1 Target Sequence:
   AAAGA TCA GCA TTG GAA GAT A      (SEQ ID NO: 4)

#2 Target Sequence:
   AAGCA CAT CGA CAA GTT AGA A      (SEQ ID NO: 5)

#3 Target Sequence:
   AAACA GTG CCG ATT GTG AAA G      (SEQ ID NO: 6)
```

Figure 44:
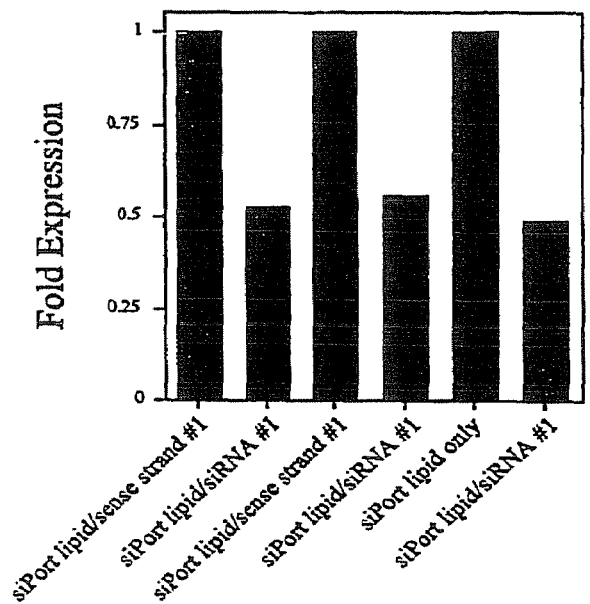
FIG. 44 shows the effect of siRNA #1 on the levels of MetAP-2 expression in OVCA 429 as determined by quantitative real-time PCR.
Figure 44:
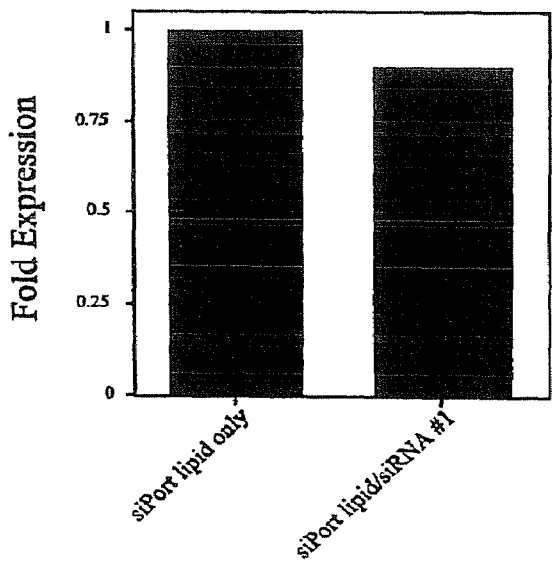

FIG. 44 shows the effect of siRNA #1 on the levels of MetAP-2 expression in OVCA 429. Control cells were transfected with the sense strand of the same siRNA alone or treated with the transfection agent (siPort lipid). Transfection of the cells with siRNA #1 reduced the levels of MetAP-2 expression by half, even though the transfection efficiency was not 100%. Little effect was observed on the levels of expression of GAPDH in those cells, indicating that gene expression was not generally affected by this treatment. Furthermore, treating the cells with siRNAs #2 and #3 did not result in a reduction in MetAP-2 expression.

Figure 45:
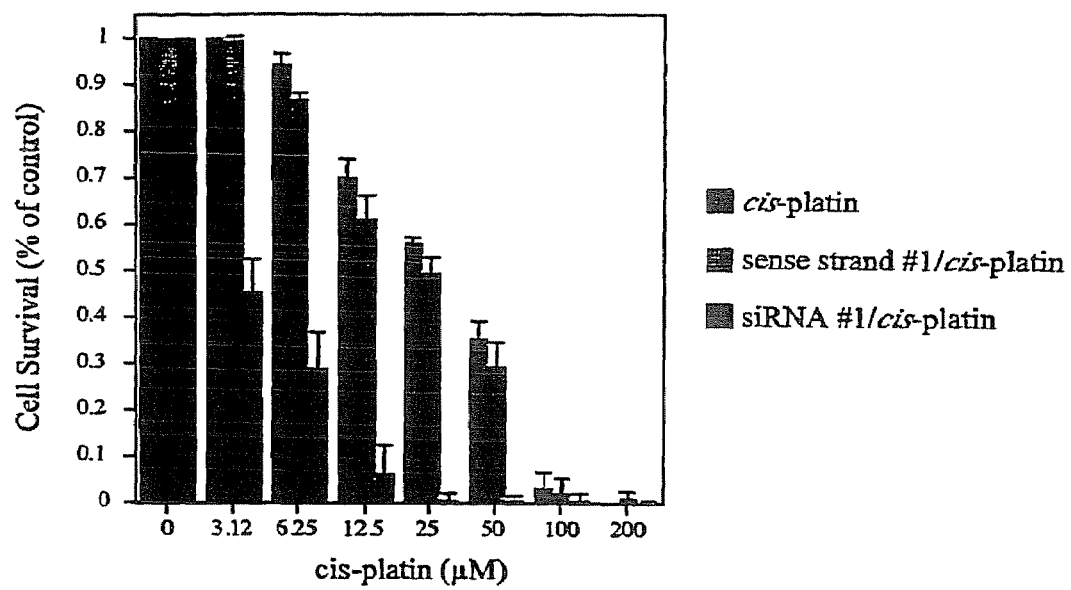
FIG. 45 is a graph representing the quantitation of cell survival as determined by MTT assays after exposing OVCA 429 to cis-platin in the presence of siRNA #1.
Figure 46:
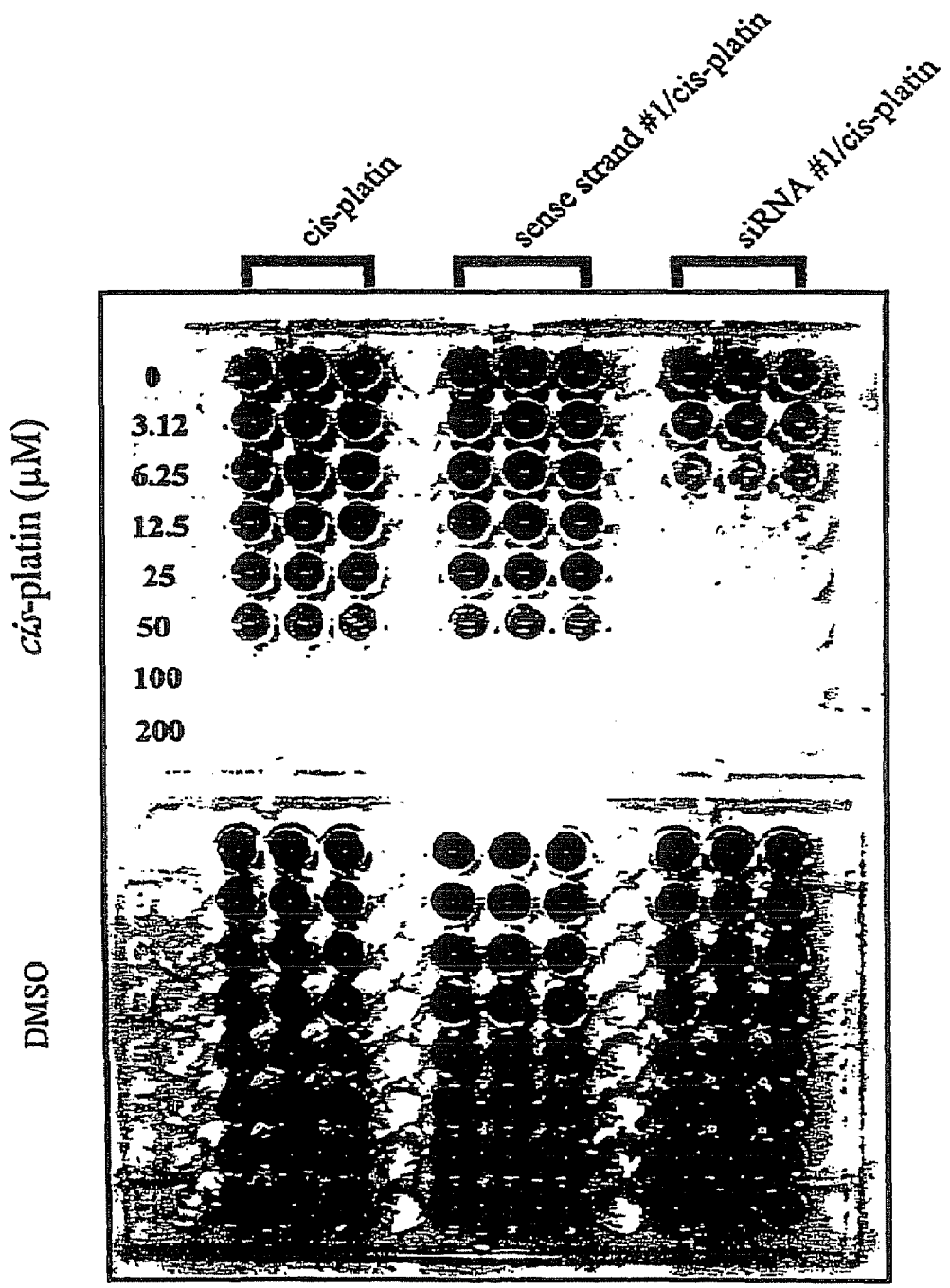
FIG. 46 is a photograph of 96-well plates containing OVCA 429 cells after performing the MTT assay (the quantitation is shown in FIG. 45) that shows the effects of cis-platin on these cells transfected with MetAP-2 siRNA #1.
Figure 47:
FIG. 47 is a schematic representation of three siRNAs (#1, SEQ ID NO: 1; #2, SEQ ID NO: 2; and #3, SEQ ID NO: 3) that were designed to target different regions of the SPARC message.

The ability of OVCA 429 to resist cis-platin when the expression of MetAP-2 was blocked was tested by treating OVCA 429 cells with siRNA #1, the sense strand #1 alone, or siPort lipid alone. After 48 hours of incubation with the siRNA the cells were exposed to varying concentrations of cis-platin or the corresponding concentrations of its solvent, DMSO, for 24 hours. The results of this experiment were quantified and are shown in FIG. 45. The results indicated that the presence of siRNA #1 reduced the IC$_{50}$ of OVCA 429 from 25 μM to approximately 3 μM. FIG. 46 shows a photograph of the 96-well plates after performing the MTT assay.

Taken together the results indicated that MetAP-2 is a useful target for therapeutic intervention in ovarian cancer.

Example 5

In Vitro Testing of Calpain 2 and S100A10 as Therapeutic Targets and Reduction of S100A11 Expression in OVCA 429 Cells 549728 (Calpain 2)

Three siRNAs were designed to target different regions of the Calpain 2 message using methods described above. The Calpain 2 siRNAs were:

```
#1 AA GGC ATA CGC CAA GAT CAA C;    (SEQ ID NO: 7)

#2 AA ACT TCT TCC TGA CGA ATC G;    (SEQ ID NO: 8)
and

#3 AA ACG CTA TTC AAG ATA TTT A.    (SEQ ID NO: 9)
```

Figure 53:
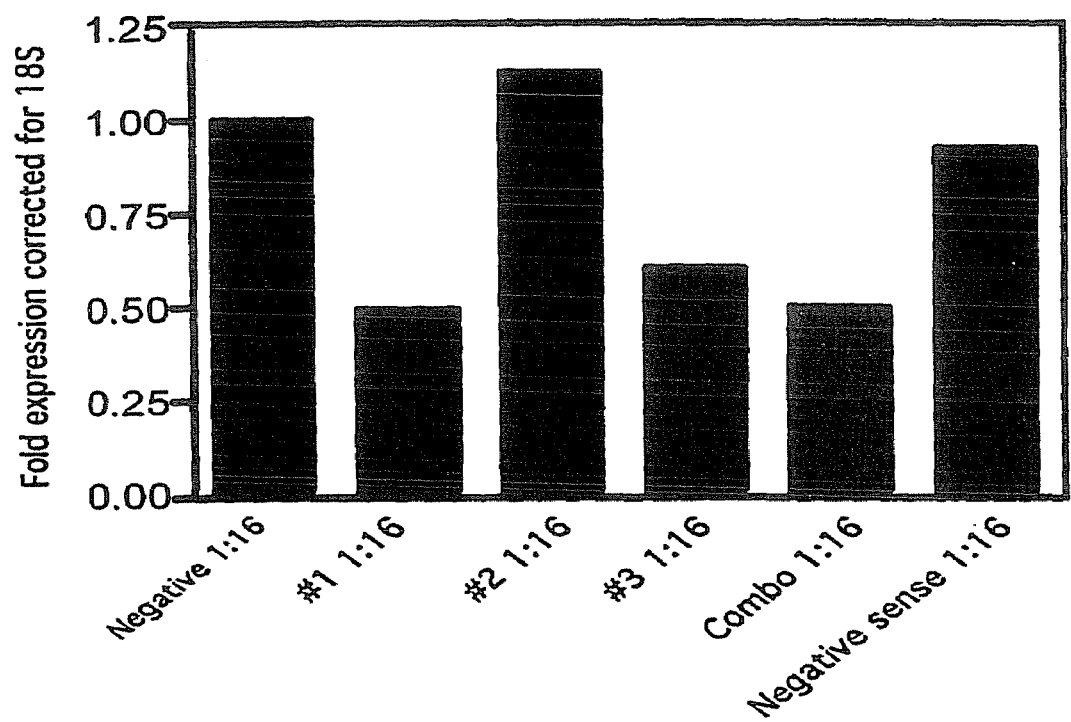
FIG. 53 is a graph representing the effects of siRNA-mediated reduction of Calpain 2 gene expression in OVCA 429 cells.
Figure 54:
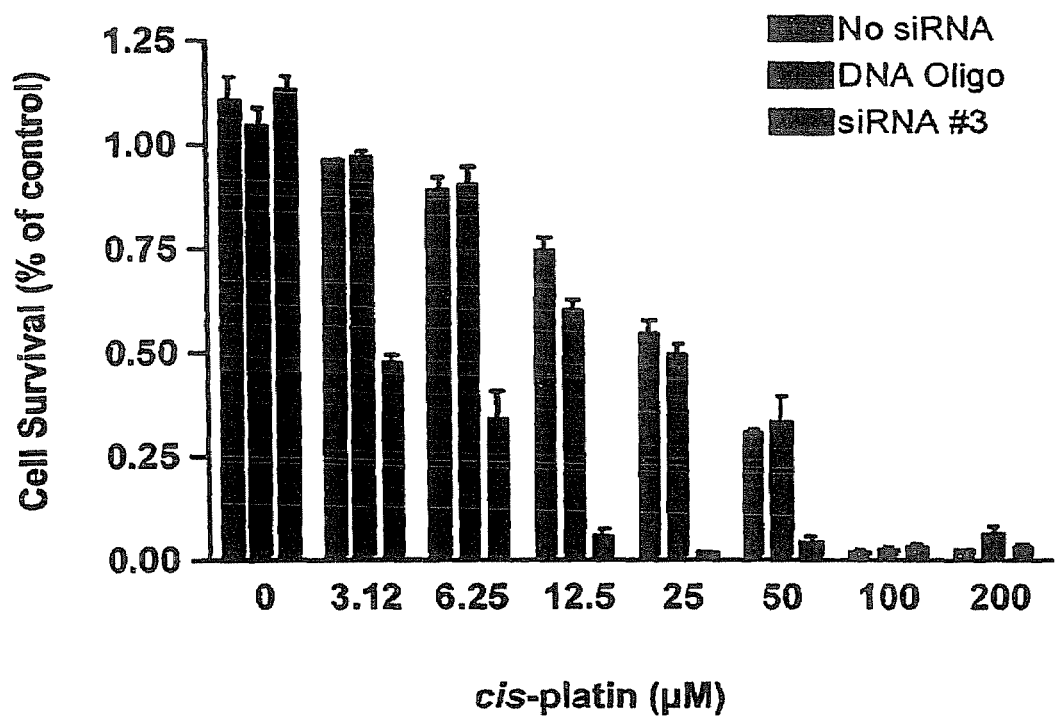
FIG. 54 is a graph representing the effects of Calpain 2 siRNA #3 on cis-platin sensitivity in OVCA 429 cells.
Figure 55:
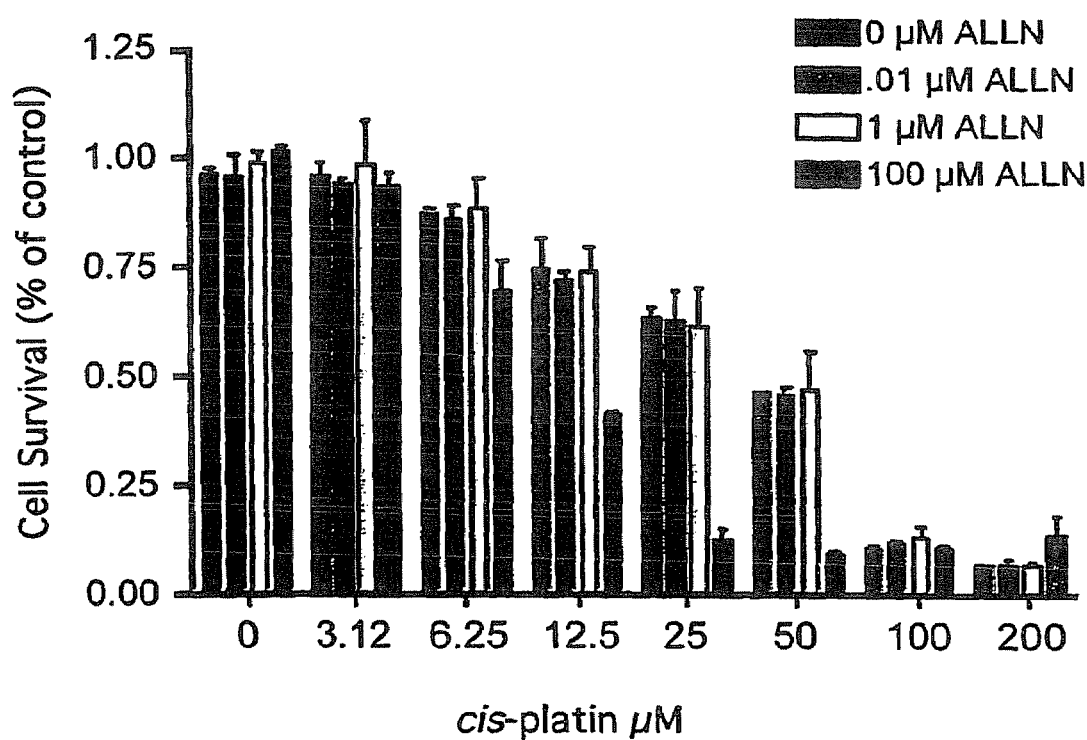
FIG. 55 is a graph representing the effects of the Calpain 2 inhibitor ALLN on cis-platin sensitivity in OVCA 429 cells.

Each siRNA was introduced into OVCA 429 cells as described above. FIG. 53 shows the results of the knockdown experiments in the OVCA 429 cells using these sequences. Sequences #1 and #3 knocked down the gene expression levels by about 50% using the protocol described above. In addition, OVCA 429 cells comprising siRNA #3 were treated with various concentrations of cis-platin. Usually, the $IC_{50}$ of OVCA 429 cells is around 25 µM cis-platin after a 24 hour exposure to the drug. As shown in FIG. 54, Calpain 2 siRNA #3 reduced the $IC_{50}$ to 3.12 µM, thereby increasing the sensitivity of the cells to cis-platin by several fold. Also, OVCA 429 cells were treated with increasing concentrations of Calpain inhibitor I (ALLN) in the presence or absence of cis-platin. As shown in FIG. 55, the ALLN reduced the $IC_{50}$ of these cells in the presence of cis-platin to 12.5 µM. Thus, the Calpain 2 siRNA #3 had a greater effect than ALLN on the sensitivity of the OVCA 429 cells to cis-platin.

756595 (S100A10)

Three siRNAs were generated against the S100A10 message:

```
#1 AA ATG GAA CAC GCC ATG GAA A;  (SEQ ID NO: 59)

#2 AA ATT CGC TGG GGA TAA AGG C;  (SEQ ID NO: 60)
and

#3 AA TAA TGA AGG ACC TGG ACC A.  (SEQ ID NO: 61)
```

Figure 56:
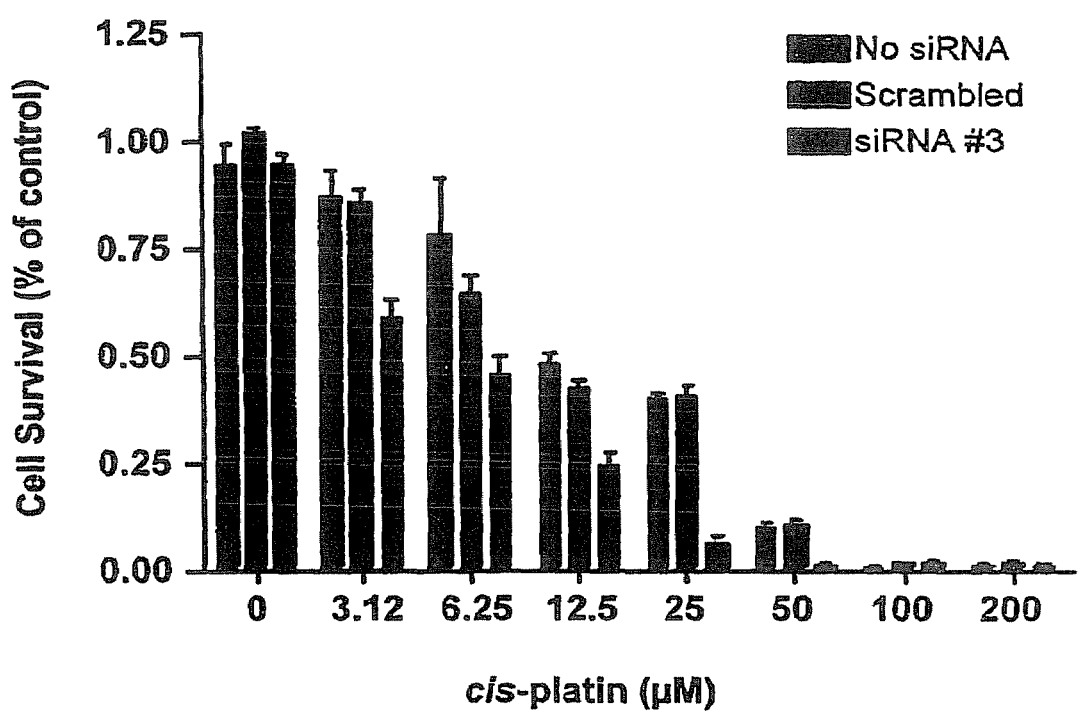
FIG. 56 is a graph representing the effects of siRNA-mediated reduction of SA100A10 gene expression on cis-platin sensitivity in OVCA 429 cells.

As shown in FIG. 56, the siRNA #3 reduced the $IC_{50}$ of the OVCA 429 cells from 25 µM to 6.25 µM cis-platin, thereby increasing the sensitivity of the cells to cis-platin.

810612 (S100A11)

Three siRNAs were designed to target different regions of the S100A11 message using methods described above. The S100A11 siRNAs were:

```
#1 AA AGG ATG GTT ATA ACT ACA C;  (SEQ ID NO: 10)

#2 AA GAA ACT GGA CAC CAA CAG T;  (SEQ ID NO: 11)
and

#3 AA TCT GAT TGG TGG CCT AGC T   (SEQ ID NO: 12)
```

Figure 57:
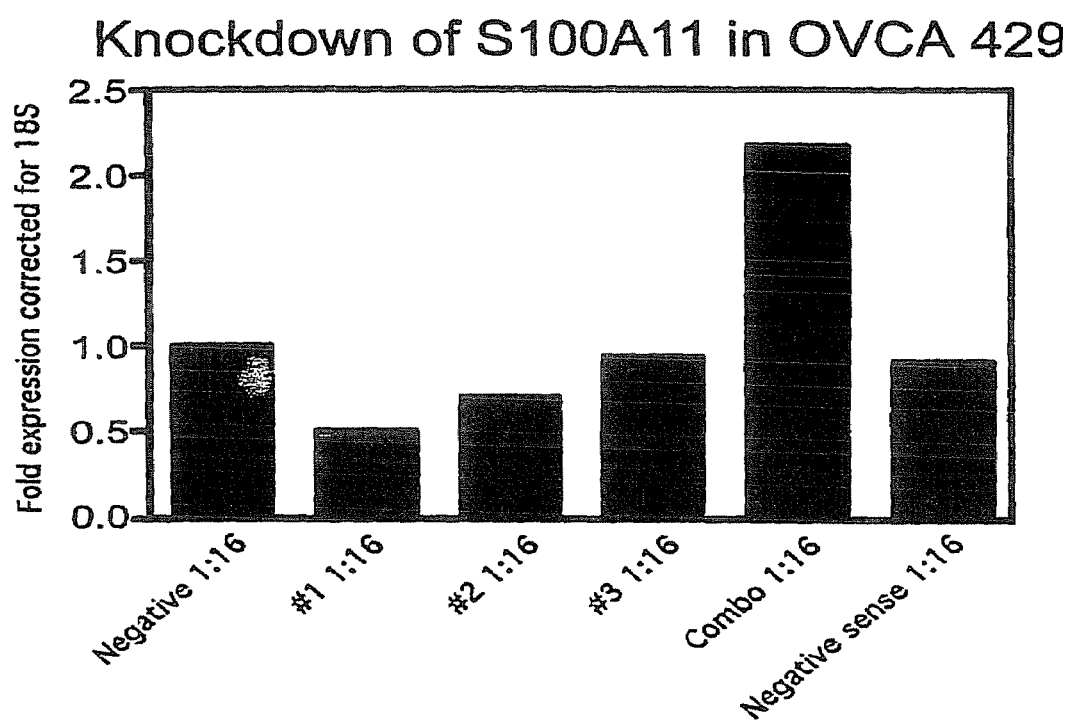
FIG. 57 is a graph representing the effects of siRNAs on S100A11 gene mRNA expression levels in OVCA 429 cells.

Each siRNA was introduced into OVCA 429 cells as described above. FIG. 57 shows that siRNAs #1 and 2 knocked down gene expression levels in the OVCA 429 cells by 50% and 25% respectively, using the methods described above.

Example 6

Expression of MetAP-2, SPARC, Calpain-2, S100A10 and S100A11 in Colon Cancer

Commercially available matched sets of colon cDNAs were obtained from BD Biosciences, Inc. (San Jose, Calif.) that were isolated from five individuals obtained from non-tumor tissue and also from adjacent tumor tissue.

Figure 58:
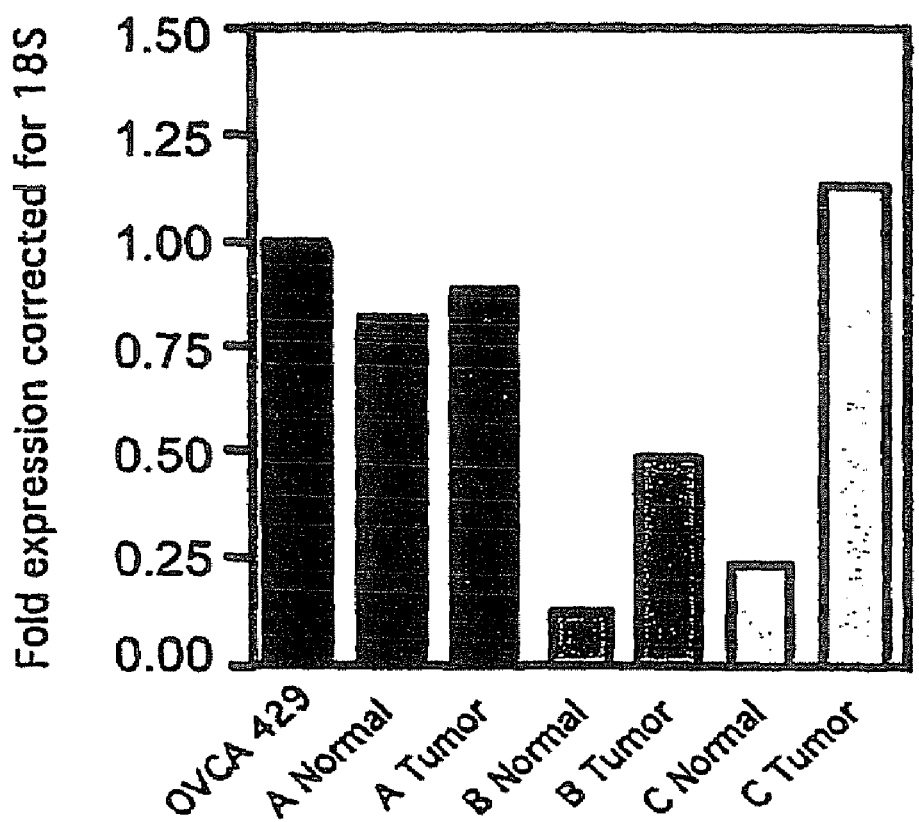
FIG. 58 is a graph representing the expression levels of MetAp-2 mRNA in normal and colon cancer cell cDNA.

Quantitative real-time PCR experiments were conducted to determine the expression levels of MetAP-2, SPARC, S100A10, S100A11 and Calpain-2 in the normal and tumor colon tissues. FIG. 58 shows the expression levels of MetAP-2 in 5 pairs of matched colon cDNAs. The data indicates that two of the patients had highly elevated expression levels in tumor cDNA compared to their matched non-tumor cDNA (patients B and C; FIG. 58). One other patient showed only slightly elevated expression in the tumor cDNA compared to its matched non-tumor cDNA (patient A; FIG. 58). The level of expression in OVCA 429 was used as a reference. Previous reports have shown that hepatic metastasis of human colon cancer can be prevented by the MetAP-2 inhibitor TNP-470 (Tanaka et al., 1995, *Cancer Res.* 55:836-9).

Figure 59:
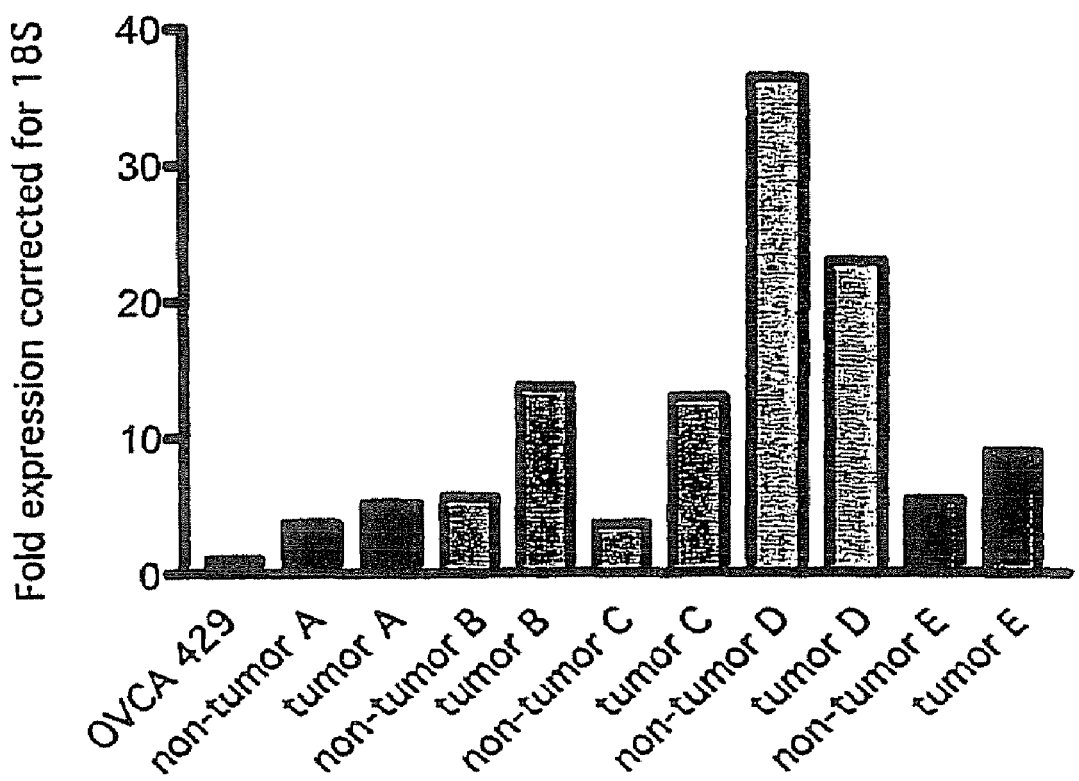
FIG. 59 is a graph representing the expression levels of SPARC mRNA in normal and colon cancer cell cDNA.
Figure 60:
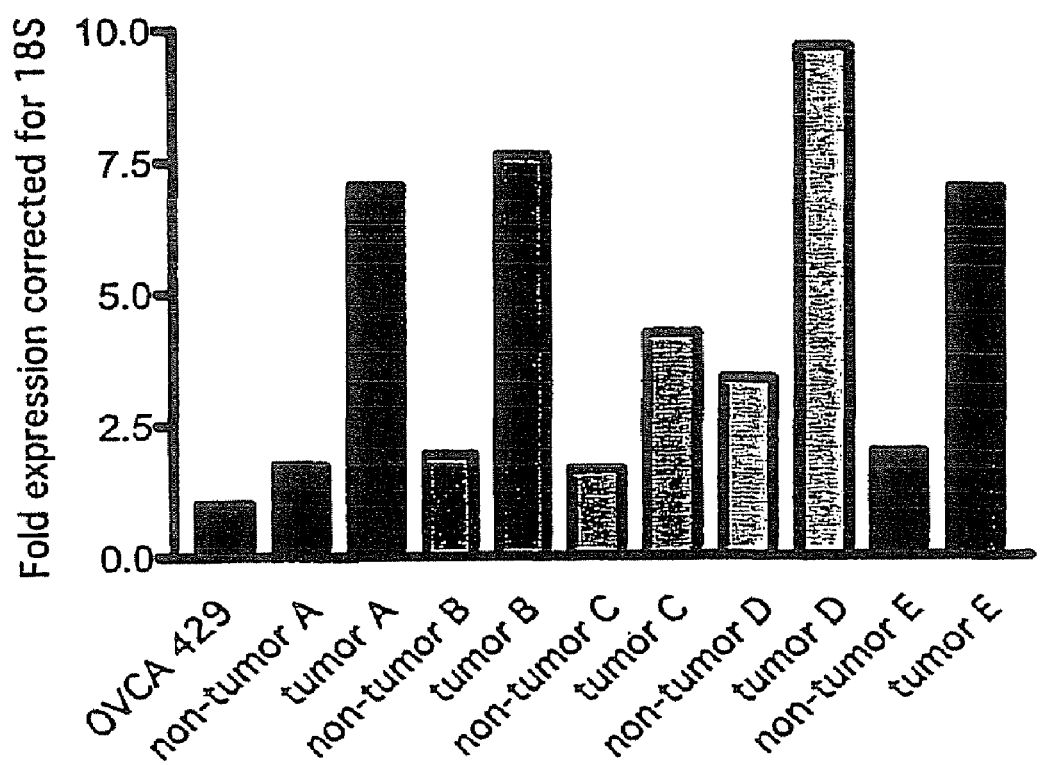
FIG. 60 is a graph representing the expression levels of S100A11 mRNA in normal and colon cancer cell cDNA.
Figure 61:
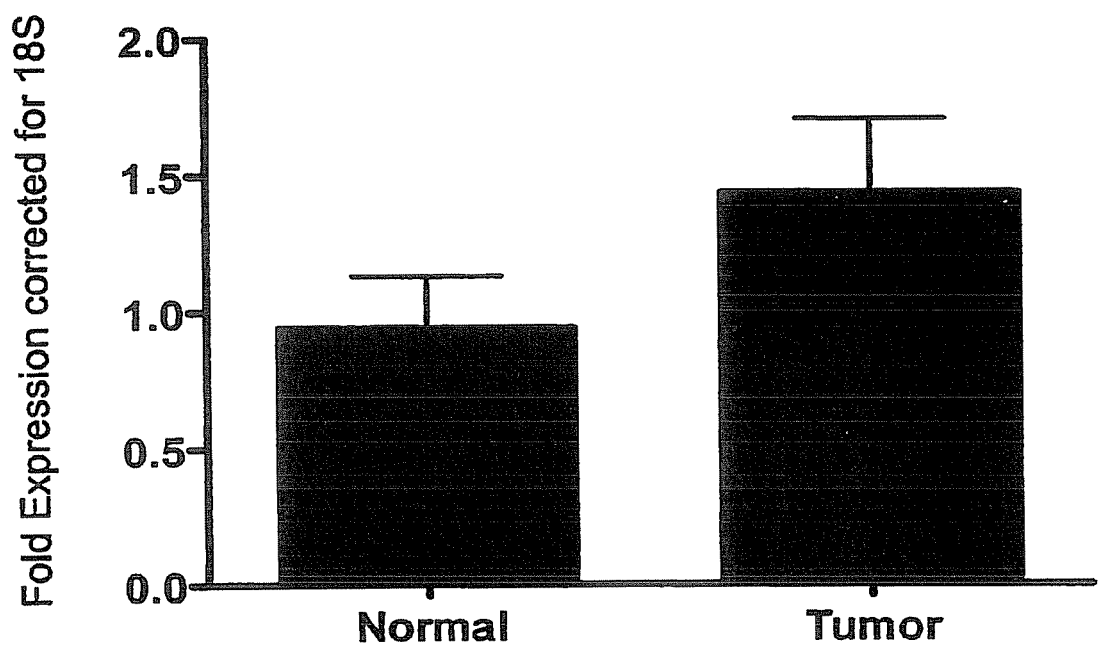
FIG. 61 is a graph representing the expression levels of S100A10 mRNA in normal and colon cancer cell cDNA.
Figure 62:
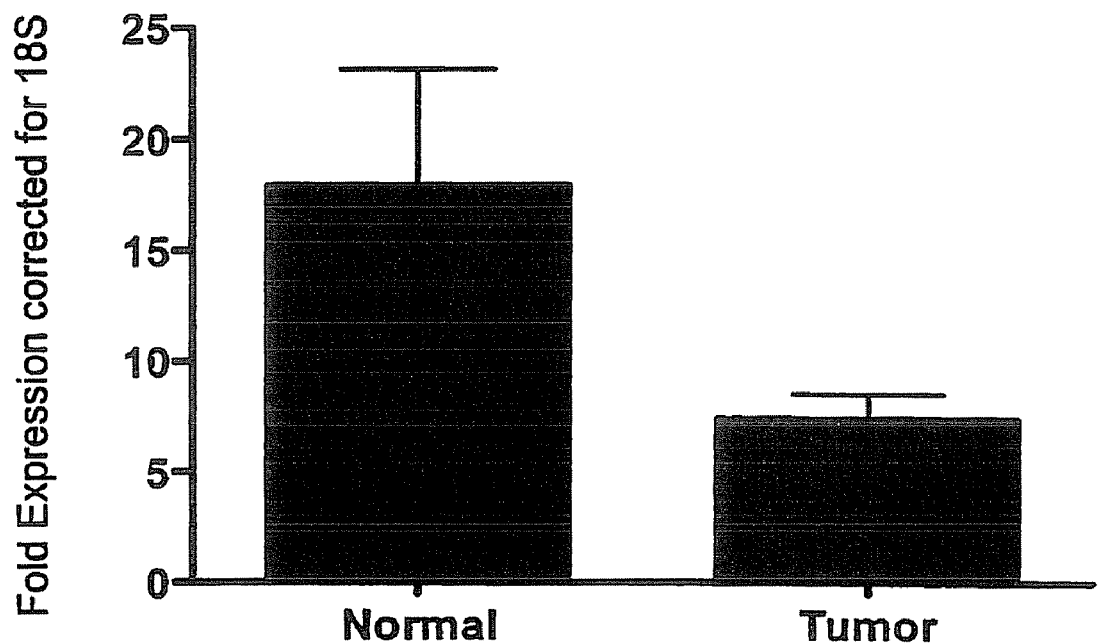
FIG. 62 is a graph representing the expression levels of Calpain-2 mRNA in normal and colon cancer cell cDNA.

FIG. 59 shows that expression levels of SPARC mRNA were elevated in 4 out of 5 matched tumor samples compared to their matched non-tumor cDNAs. FIG. 60 shows that expression levels of S100A11 mRNA were elevated in all of the matched tumor samples compared to their matched non-tumor cDNAs. FIG. 61 shows that expression levels of S100A10 mRNA were elevated in 4 out of 5 matched tumor samples compared to their matched non-tumor cDNAs. FIG. 62 shows that expression levels of Calpain-2 mRNA were elevated in all of the matched tumor samples compared to their matched non-tumor cDNAs.

Taken together these observations suggest that MetAP-2, as well as SPARC, S100A11, S100A10, and Calpain-2, are therapeutic targets for colon cancer patients.

Example 7

Sandwich ELISA for Detecting Secreted Proteins in Serum

The wells of 96-well microtiter plates are coated with antibodies raised against a gene product of interest. Aliquots of the purified recombinant target gene product are diluted serially and are used to generate a standard curve for quantitation. Aliquots of patient sera are then added to each well. The plate is covered to minimize evaporation and is incubated at 4° C. for a few hours to overnight. The antigen is removed and the wells are washed 3 times with phosphate buffered saline (PBS). 300 µl of blocking solution (3% w/v fish gel solution in PBS) is added to each well and incubated for 2 hours at room temperature. Blocking solution is removed and the wells are washed 3 times with PBS. The appropriate antibody conjugated to horseradish peroxidase is then added to each well (100 µl per well) and incubated at room temperature for 1-2 hours. The antibody is then removed and the wells are washed 3 times with NP-40 solution (0.05% v/v NP-40 in PBS). Binding is detected by adding ABTS (Rockland Immunochemicals) to each well (at 100 µl per well) for 30 minutes at room temperature and reading absorbance at 405 nm using a microplate reader. If alkaline phosphate conjugates are used instead of peroxidase, pNPP (Rockland Immunochemicals) is used instead of ABTS to detect binding.

Once the limit of detection is determined from standard curves generated using purified proteins, a number of subjects who do not have cancer and a number of patients who have been diagnosed as having cancer or benign conditions are tested to determine an expected range of concentrations for the particular gene product of interest. The expected range for patients with cancer defines the limit that can be used to identify or distinguish a patient with ovarian cancer or a patient with recurring disease from a responding patient or a healthy subject without cancer.

Example 8 siRNA-Mediated "Knockdown" of Gene Expression siRNAs specific for several genes were tested for their ability to reduce (or "knockdown") their respective genes in ovarian cancer cell lines following the protocols as described above. In each case several siRNAs were tested against a control (non-specific) siRNA that was GC-content matched (from Dharmacon, Inc, Lafayette, Colo.) to the test siRNAs. In some cases a negative control (no treatment) was also included. The level of expression knockdown varied with different siRNAs. The specific genes and the siRNA sequences for each specific gene are described below:

1. Two siRNAs were generated SAPK/Erk1 (L36870):
   L36870 (726147)
   Target sequence #1 (SEQ ID NO: 64): AAA TGG GAC GAG GAG CTT ATG (starts at bp 320 in the coding sequence)
   Target sequence #2 (SEQ ID NO: 65): AAG CGC ATC ACG ACA AGG ATA (starts at bp 831 in the coding sequence)
   Both sequences were successful in reducing expression of SAPK, with sequence #2 giving a 60% reduction in the level of mRNA.

2. Three siRNAs were generated for eEF1ε (BC005291):
   BC005291 (306921)
   Target sequence #1 (SEQ ID NO: 66): AAC AGG ATT GAC TAC TAT AGC (starts at bp 123 in the coding sequence)
   Target sequence #2 (SEQ ID NO: 67): AAT ACA GGG TCA CTC AAG TAG (starts at bp 227 in the coding sequence)
   Target sequence #3 (SEQ ID NO: 68): AAA TAT CTT AAT GTG TCT CGC (starts at bp 412 in the coding sequence)
   Target sequences #s 1 and 2 were successful in reducing the expression of eEF1ε, with sequence #1 giving a 65% reduction in the level of mRNA.

3. Three siRNAs were generated for G-CSFR (M59818):
   M59818 (809639)
   Target sequence #1 (SEQ ID NO: 69): AAG TGT GAG CTG CGC CAC AAG (starts at bp 793 in the coding sequence).
   Target sequence #2 (SEQ ID NO: 70): AAG AGC CCC CTT ACC CAC TAC (starts at bp 1666 in the coding sequence).
   Target sequence #3 (SEQ ID NO: 71): AAC AGG AAG AAT CCC CTC TGG (starts at bp 1957 in the coding sequence).
   Target sequences #s 1 and 3 reduced the level of expression of G-CSFR, with sequence #1 53% reduction in the level of mRNA.

4. Three siRNAs were generated for ARA9/XAP2 (U31913):
   U31913 (814731)
   Target sequence #1 (SEQ ID NO: 72): AAA CGT GTG ATA CAG GAA GGC (starts at bp 48 in the coding sequence)
   Target sequence #2 (SEQ ID NO: 73): AAC AAG TAC GAC GAC AAC GTC (starts at bp 775 in the coding sequence)
   Target sequence #3 (SEQ ID NO: 74): AAC GTC AAG GCC TAC TTC AAG (starts at bp 790 in the coding sequence)
   Target sequences #s 2 and 3 resulted in reduced expression of ARA9, with sequence #3 giving a 50% reduction in the level of mRNA.

5. Three siRNAs were generated for RNPS1 (AF015608):
   AF015608 (897594)
   Target sequence #1 (SEQ ID NO: 75): AAT ATT CAT ACG GCA TGG ACT (starts at bp 327 in the coding sequence)
   Target sequence #2 (SEQ ID NO: 76): AAC CTA AAA TAG AAG ACC CCT (starts at bp 680 in the coding sequence)
   Target sequence #3 (SEQ ID NO: 77): AAA AGA TGC TGA CTC AGA AAA (starts at bp 752 in the coding sequence)
   All three sequences were successful in reducing the expression of RNPS1, with sequence #1 giving a 35% reduction in the level of mRNA.

6. Three siRNAs were generated for Fused toes (BC001134):
   BC001134 (321247)
   Target sequence #1 (SEQ ID NO: 78): AAC CTA AAA TAG AAG ACC CCT (starts at bp 680 in the coding sequence)
   Target sequence #2 (SEQ ID NO: 79): AAG ACC CCT ATG CAA TTA GCT (starts at bp 692 in the coding sequence)
   Target sequence #3 (SEQ ID NO: 80): AAA AAG CCT GAA GAA CAG CAC (starts at bp 769 in the coding sequence)
   All three sequences were successful in reducing the expression of Fused toes, with sequence #2 giving a 43% reduction in the level of mRNA.

7. Three siRNAs were generated for Grancalcin (BC005214):
   BC005214 (34140)
   Target sequence #1 (SEQ ID NO: 81): AAA TGG GAT TTA ATG CAT TCA (starts at bp 323 in the coding sequence)
   Target sequence #2 (SEQ ID NO: 82): AAC TTC ATG ACT GTT GAT CAA (starts at bp 379 in the coding sequence)
   Target sequence #3 (SEQ ID NO: 83): AAC ATC ATG AGT TGC GTC AAG (starts at bp 419 in the coding sequence)
   All three sequences were successful in reducing the expression of Grancalcin, with sequence #2 giving an 83% reduction in the level of mRNA.

8. Three siRNAs were generated for SRB1/CLA1/CD3611 (BC022087):
   BC022087 (756687)
   Target sequence #1 (SEQ ID NO: 84): AAG CAG CAG GTC CTT AAG AAC (starts at bp 109 in the coding sequence)
   Target sequence #2 (SEQ ID NO: 85): AAT CTC ATC AAC AAG TAC TTT (starts at bp 565 in the coding sequence)
   Target sequence #3 (SEQ ID NO: 86): AAT TCA GAA CGT CAG CAC CTG (starts at bp 981 in the coding sequence)
   Target sequences #s 1 and 3 were successful in reducing the expression of SRB1, with sequence #1 giving a 60% reduction in the level of mRNA.

9. Three siRNAs were generated for KIAA0082 (BC031890):
   BC031890 (825293)
   Target sequence #1 (SEQ ID NO: 87): AAG AGG AGA ACT GAC CCA GAA (starts at bp 4 in the coding sequence)
   Target sequence #2 (SEQ ID NO: 88): AAA TGA GCG ATT GGA TGG TGG (starts at bp 509 in the coding sequence)
   Target sequence #3 (SEQ ID NO: 89): AAG ATC ATC AAG GGC TCC AGT (starts at bp 2164 in the coding sequence)
   Sequence #1 gave a 65% reduction in the level of mRNA. Sequence #2 and #3 had no effect on mRNA level.

10. Three siRNAs were generated for eIF2Bε (BC013590):
    BC013590 (1630998)
    Target sequence #1 (SEQ ID NO: 90): AAT GTG GTT CGA ATA ATT ACA (starts at bp 352 in coding sequence)
    Target sequence #2 (SEQ ID NO: 91): AAA CTC GAG ATG ACT TTG TGC (starts at bp 800 in coding sequence)
    Target sequence #3 (SEQ ID NO: 92): AAT CAA CAG CTG CAG AGG TTC (starts at bp 2098 in coding sequence)

Sequence #1 gave a 57% reduction in the level of mRNA, sequence #2 gave a 54% reduction, and sequence #3 gave a 43% reduction in the level of mRNA.

11. Three siRNAs were generated for Calponin 2 (D83735):
    D83735 (713886)
    Target sequence #1 (SEQ ID NO: 93): AAG GAT GGA ACT ATC TTA TGC (starts at bp 163 in coding sequence)
    Target sequence #2 (SEQ ID NO: 94): AAT TTC GAC GAT GCC ACC ATG (starts at bp 457 in coding sequence)
    Target sequence #3 (SEQ ID NO: 95): AAC CGA CAA GTG TGA CAA CTC (starts at bp 708 in coding sequence)
    All three sequences reduced the level of gene expression, with sequence #3 giving a 75% reduction in the level of mRNA.

12. Three siRNAs were generated for HYA22 (D88153):
    D88153 (123980)
    Target sequence #1 (SEQ ID NO: 96): AAA GAA ATG TGT GGT CAT TGA (starts at bp 507 in the coding sequence)
    Target sequence #2 (SEQ ID NO: 97): AAA TCG ATG GAA CTA TAC ATC (starts at bp 596 in coding sequence)
    Target sequence #3 (SEQ ID NO: 98): AAC TAT ACA TCA GGT GTA TGT (starts at bp 606 in coding sequence)
    All three sequences reduced the level of gene expression, with sequence #3 giving a 60% reduction in the level of mRNA.

13. Three siRNAs were generated for CA 125 (BC009808):
    BC009808 (CA 125)
    Target sequence #1 (SEQ ID NO: 99): AAT GGT TTC ACC CAT CAG AGC (starts at bp 235 in the coding sequence)
    Target sequence #2 (SEQ ID NO: 100): AAG GGC TCA GCT ACA TTC AAC (starts at bp 2203 in the coding sequence)
    Target sequence #3 (SEQ ID NO: 101): AAT ACA ACG TCC AGC AAC AGT (starts at bp 3380 in the coding sequence)
    Sequence #3 gave a 50% reduction in the level of mRNA.

14. Two siRNAs were generated for HMT1 (AF222689) and tested in Hey cells:
    AF222689
    Target Sequence #1 (SEQ ID NO: 102): AAC TCC ATG TTT CAT AAAC CGG (starts at bp 202 in the coding sequence)
    Target Sequence #2 (SEQ ID NO: 103): AAC GTG TAT GGC TTC GAC ATG (starts at bp 619 in the coding sequence)
    Both sequences were successful in reducing the expression of HMT1 mRNA with sequence # 1 giving approximately 70% reduction and sequence # 2 just over a 60% reduction.

15. Three siRNAs were generated for MPP10 (X98494) and tested in Hey cells:
    X98494
    Target sequence #1 (SEQ ID NO: 104): AAG TTC CAG AAA TCT GAA ATA (starts at bp 357 in the coding sequence)
    Target sequence #2 (SEQ ID NO: 105): AAG AAA ATC CAG AAC ATG TAG (starts at bp 1043 in the coding sequence)
    Target sequence #3 (SEQ ID NO: 106): AAA ACA GTA GCT TCG GAG AAG starts at bp 1414 in the coding sequence)
    All three sequences gave a reduction in mRNA expression with sequence # 1 giving almost 90% reduction, and sequences # 2 and 3 with approximately 30% and 40% reduction respectively.

16. Two siRNAs were generated for IGFBP-7 (BC017201) and tested in OVCA 429.
    BC017201
    Target sequence #1: AAG GTA AAA AGG GGT CAC TAT (starts at bp 583 in the coding sequence). (SEQ ID NO. 107)
    Target sequence #2: AAA GGG GTC ACT ATG GAG TTC (starts at bp 590 in the coding sequence). (SEQ ID NO. 108)
    Only sequence # 1 gave a reduction in mRNA levels that was approximately 60% compared to the control.

17. One siRNA was generated for NM23-D (BC004880) and tested in OVCA 429 cells:
    BC004880 (203003)
    Target sequence #3 AAT GTC ATC CAC GCC AGC GAC (starting bp 442 from $1^{st}$ ATG) (SEQ ID NO 135)
    Only target sequence # 3 reduced mRNA levels, by approximately 50% compared to control.

18. Three siRNAs were generated for WDR1 (AB010427) and tested in OVCA 429 cells:
    AB010427
    Target sequence #1: AAT GGA AAG TGC GTC ATC CTA (starting bp 106 from $1^{st}$ ATG) (SEQ ID NO 136)
    Target sequence #2 AAG TTC ACA ATT GGC GAC CAC (starting bp 544 from $1^{st}$ ATG) (SEQ ID NO 137)
    Target sequence #3: AAG TGC TTC AGC ATC GAC AAC (starting bp 1309 from $1^{st}$ ATG) (SEQ ID NO 138)
    All target sequences reduced mRNA levels, #1 by approximately 85%, #2 by approximately 75% and #3 by approximately 70% compared to control.

19. One siRNA was generated for Vinexin β (AF037261) and tested in OVCA 429 cells;

```
    AF037261
    Target sequence #2:
    AAG AGT TAC CTA GAA GCA CCT    (SEQ ID NO 139)
    ```

Target sequences #1 and #3 did not reduce mRNA levels compared with control while #2 reduced mRNA by approximately 50% compared to control.

20. Three siRNAs were generated for KLK6 (BC015525) and tested in OVCA 429 cells:

```
    BC015525
    Target sequence #1:
    AAA AAA CCG AAT CTT CAG GTC    (SEQ ID NO 140)

Target sequence #2:
    AAA CTC TCT GAA CTC ATC CAG    (SEQ ID NO 141)

Target sequence #3:
    AAC TGG ATC CAA AAA ACC ATT    (SEQ ID NO 142)
    ```

Target sequences #1 did not reduce mRNA levels compared with control while #2 reduced mRNA by approximately 42% and #3 by approximately 55% compared to control.

21. One siRNA was generated for eIF5 (U49436) and tested in OVCA 429 cell:
    U49436
    Target sequence #1 mRNA Target Sequence: AAT GAC CGT TAC ATT GTC AAT (SEQ ID NO 143)

Target sequences #2 and #3 did not reduce mRNA levels compared with control while #1 reduced mRNA by approximately 59% compared to control.

22. One siRNA was generated for zinc finger protein 262/MYM (AB007885) and tested in OVCA 429 cells:
AB007885
   Target sequence #3: AAA ATA TGG GAA CCT ACA ATA (starting bp 3058 from 1$^{st}$ ATG) (SEQ ID NO 144)
   Target sequences #1 and #2 did not reduce mRNA levels compared with control while #3 reduced mRNA by approximately 45% compared to control.

Example 9

In Vitro Functional Testing of Validated Genes

The ability of specific siRNAs to enhance the sensitivity of OVCA 429 and OVCAR-3 cells to cis-platin was examined substantially as disclosed above in Examples 3-5 above. In each case cis-platin sensitivity was enhanced in the presence of the specific siRNAs but not with the non-specific (control) siRNA or the negative control (no treatment). The data indicate that the genes tested may be functionally involved in the development of cis-platin resistance in ovarian cancer cell lines. The results are summarized in Table 4.

of the two mice. The data demonstrated that the control animal carrying the tumor continued to grow the tumor in the absence of any chemotherapy (mouse #1). The animal that received the cis-platin treatment, in contrast, exhibited a stabilization of the tumor size (mouse #2). A photograph of the tumors before and after cis-platin treatment is also shown.

Figure 64:
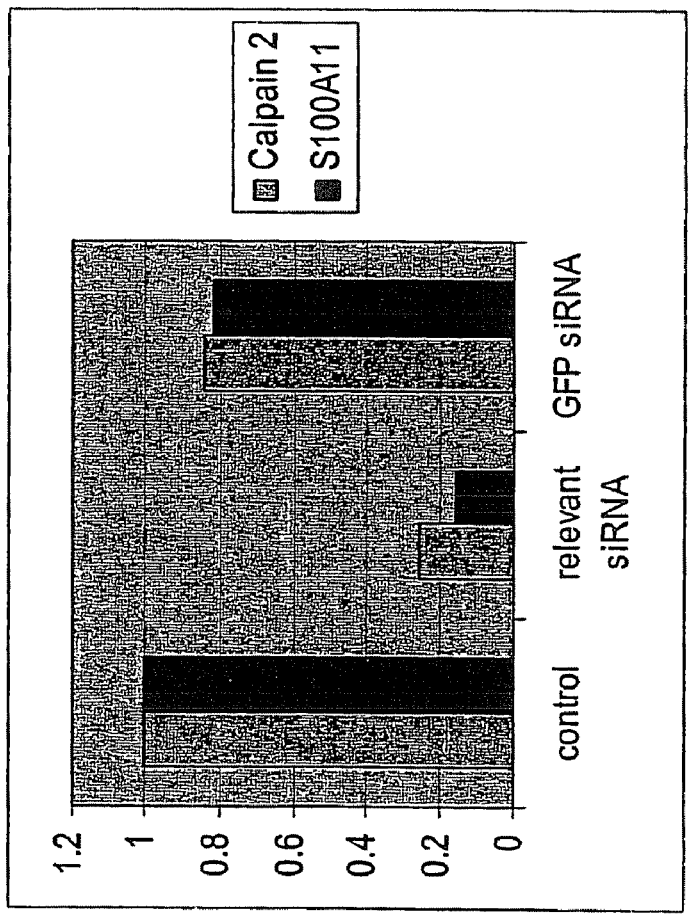
FIG. 64 is a graph that shows stable expression of siRNAs against either Calpain 2 or S100A11 in OVCAR-3 cells. In the control lanes, the expression of both mRNAs was measured in cells without treatment or the irrelevant GFP siRNA.

This protocol is repeated using stable cell lines expressing siRNAs against genes identified herein (MetAP-2, SPARC, S100A10, S100A11 and Calpain-2). Stable OVCAR-3 cell lines expressing either Calpain 2 or S100A11 siRNAs, as well as a control OVCAR-3 cell line expressing stable siRNA against green fluorescent protein (GFP, a cell growth-irrelevant marker protein), have been developed; expression of Calpain 2 and S100A11 and the effects of siRNA expression as measured by real time quantitative PCR are shown in FIG. 64. Fifteen mice are split into three groups of five. One group is treated as control, is injected with OVCAR-3 cells without siRNA expression, the second group is injected with siRNA-expressing OVCAR-3 cells and the third group is injected with GFP-specific siRNA expressing OVCAR-3 cells. After measurable tumors become apparent, the control group receives a saline injection, while the second and third groups receives the standard cis-platin treatment. Tumor growth is observed as a function of body weight as described above.

TABLE 4 in vitro cis-platin sensitivity tests

| Accession Number | Names | siRNA sequence | Tested in OVCA 429 cells | 429: increased sensitivity to cis-platin | Tested in OVCAR-3 cells | OVCAR-3: increased sensitivity to cis-platin |
|---|---|---|---|---|---|---|
| M59818 | G-CSFR | #1 | yes | yes | | |
| U31913 | ARA9 XAP 2 | #3 | yes | yes | yes | yes |
| AF015608 | RNPS1 | #1 | yes | yes | | |
| BC001134 | Fused toes | #2 | yes | yes | yes | yes |
| BC005214 | Grancalcin | #2 | yes | yes | yes | yes |
| BC022087 | SRB1 | #1 | yes | yes | yes | yes |
| BC031890 | KIAA0082 | #1 | yes | yes | yes | yes |
| AB007885 | Zinc-finger protein | #3 | yes | yes | yes | yes |
| BC004880 | NM23D | #3 | yes | yes | yes | yes |
| AB010427 | WDR1 | #1 | | no | yes | yes |
| U49436 | eIF5 eIF5A | #1 | yes | yes | yes | yes |
| D83735 | Calponin 2 | #3 | yes | yes | Yes | yes |
| BC015525 | KLK6 | #3 | yes | yes | yes | yes |
| AF037261 | Vinexin B | #2 | | no | yes | yes |
| BC017201 | IGFBP-7 | #1 | yes | yes | yes | yes |
| D88153 | HYA22 | #3 | yes | marginal | yes | yes |
| BC013590 | eIF2Bε | #1 | yes | yes | yes | yes |
| L36870 | SAPK/Erk1 | #2 | yes | yes | yes | yes |

Example 10

In Vivo Experimentation

Figure 63:
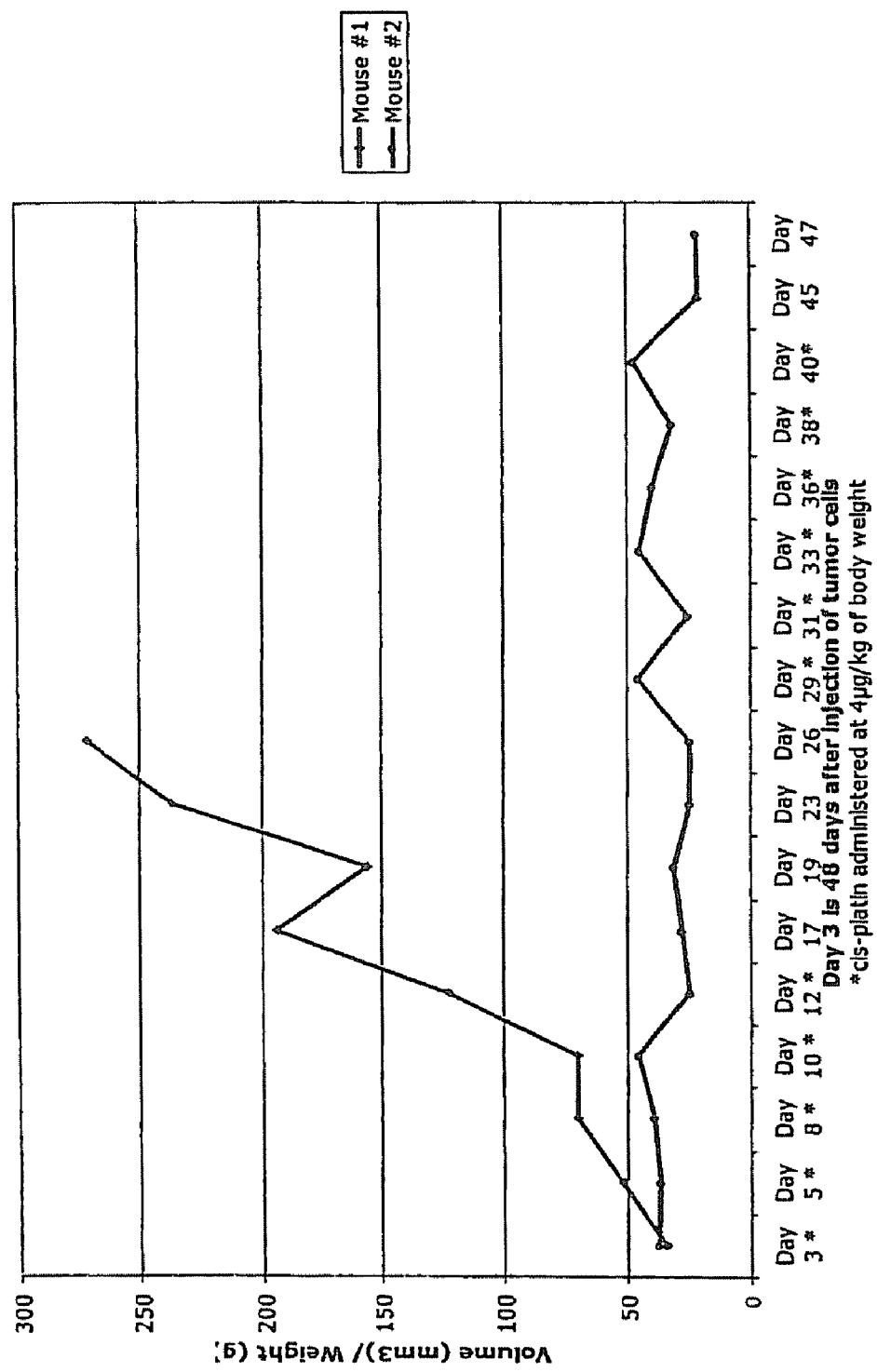
FIG. 63 shows the volume of the tumor as a function of body weight of two nude mice injected with OVCAR-3 cells (15 million/injection, obtained from the AMERICAN TYPE CULTURE COLLECTION, Manassas, Va., Accession No. HTB-161) and treated after 35 days with cis-platin at 4 μg/kg body weight administered by IP injection 3 times a week for 2 weeks, followed by 1 week with no treatment or treated with saline solution alone as control.

The following protocol was developed for examining tumor growth using OVCAR-3 cells and nude mice: OVCAR-3 cells (15 million/injection) were inoculated under upper arm region of nude mice. Visible lumps appeared after 25 days. The tumors were measurable at about 35 days after inoculation and animals were then either treated with cis-platin at 4 μg/kg body weight administered by IP injection 3 times a week for 2 weeks, followed by 1 week with no treatment or treated with saline solution alone as control. FIG. 63 shows the volume of the tumor as a function of body weight In another experiment, fifteen mice split into groups of five ads inoculated with unadulterated (i.e., non-recombinant) OVCAR-3 cells and tumors permitted to grow. One group is treated as control. After measurable tumors become apparent, the control group receives a saline injection, the second group receives the standard cis-platin treatment as described above, and the third group receives the standard cis-platin treatment combined with TNP-470 (a clinically-recognized fumagillin derivative). Tumor growth is observed as a function of body weight as described above.

The information disclosed in the Examples can be summarized as follows:

TABLE 5

| Accession # | Names | Tested in ovarian cancer patient tissue sample panel | Passed in vitro functional validation in OVCA 429, OVCAR-3 (or both) or Hey* |
|---|---|---|---|
| BC015973 | S100A10 p11 CLP11 Calpactin 1 light chain 42C | yes | yes |
| BC001410 | S100A11 S100C Calgizzarin | yes | yes |
| AF261089 | Calpain 2 CANPL2 MCANP | yes | yes |
| BC004974 | SPARC Osteonectin BM-40 | yes | yes |
| BC013782 | MetAP2 p67eIF2 MNPEP | yes | yes |
| BC015525 | KLK6 Zyme Neurosin Protease M | yes | yes |
| AF222689 | HMT1 HMT2 ANM1 HCP1 | yes | no |
| U31913 | ARA9 XAP2 | no | yes |
| D83735 | Calponin 2 | no | yes |
| U19251 | NAIP | yes | no |
| BC005291 | eEF1ε p18 | yes | no |
| AF015608 | RNPS1 | yes | yes |
| U49436 | eIF5 eIF5A | yes | yes |
| BC013590 | eIF2Bε | yes | yes |
| M65217 | HSF2 HSTF2 | no | no |
| AB010427 | WDR1 NORI-1 | yes | yes |
| BC001134 | Fused toes | no | yes |
| BC004880 | NM23D mn23-H4 | yes | yes |
| U10439 | ADAR1 | yes | no |
| BC005214 | Grancalcin | no | yes |
| BC009808 | NBR1 | no | no |
| L36870 | SAPK/Erk1 JNKK1 MEK4 MKK4 MAPKK4 | yes | yes |
| AB007885 | Zinc finger protein-262 MYM | yes | yes |
| D88153 | HYA22 | yes | yes |
| AB049635 | MRPL4 CGI-28 | yes | no |
| AF037261 | Vinexin β | yes | yes |
| M59818 | G-CSFR | yes | yes |
| BC015710 | RAB22A | yes | no |
| BC017201 | IGFBP-7 MAC25 FSTL2 | no | yes |
| BC011770 | FAST kinase | no | no |
| AB057597 | TESK2 | no | no |
| BC022087 | SRB1 CLA1 CD36L1 | yes | yes |
| BC031890 | KIAA0082 | no | yes |
| NM_006312 | NCOR2 | no | no |
| BC032338 | MT1 | yes | no |
| X98494 | MPP10 | no | no |

*All genes (KLK6, ARA9, Calponin 2, RNPS1, eIF5, eIF2Bε, WDR1, Fused toes, NM23D, Grancalcin, SAPK/Erk1, zinc finger protein-262 MYM, HYA22, Vinexin β, G-CSFR, IGFBP-7, SRB1, or KIAA0082) where expression is elevated on drug-resistant tumor cells were tested in OVCAR-3 or OVCA 429 cells, and all genes (MPP10, HMT1, NAIP, Eef1ε, RAB22A, NCOR2, or MT1) where expression is reduced in the most resistant tumor cells were tested in Hey cells.

It should be understood that the foregoing disclosure emphasizes certain specific embodiments of the invention and that all modifications or alternatives equivalent thereto are within the spirit and scope of the invention as set forth in the appended claims.

---

What is claimed is:

1. A method of assessing whether an ovarian cancer patient's tumor is resistant to cisplatin comprising the steps of:
   (a) measuring a gene expression level of at least one gene selected from the group consisting of S100A10 and S100A11 in
      (i) an ovarian cancer tumor sample taken from the patient, and
      (ii) a cisplatin responsive ovarian tumor sample;
   (b) comparing the expression level of said at least one gene in the ovarian cancer tumor sample taken from the patient and the cisplatin responsive ovarian tumor sample; and
   (c) determining that the ovarian cancer patient's tumor is resistant to cisplatin when the expression level of said at least one gene in the ovarian cancer tumor sample taken from the patient is at least 1.2-fold greater than the expression level of said at least one gene in the cisplatin responsive ovarian tumor sample.

2. The method of claim 1, wherein said measuring is by nucleic acid hybridization, reverse transcription-polymerase chain reaction (RT-PCR), or antibody-binding.

3. A method for assessing disease progression of ovarian cancer in a patient, comprising the steps of:
   (a) measuring a gene expression level of at least one gene selected from the group consisting of S100A10 and S100A11 in an ovarian cancer tumor sample taken from the patient;
   (b) repeating step (a) using an ovarian cancer tumor sample obtained from the patient at a subsequent time;
   (c) comparing the expression level of said at least one gene from step (a) with the gene expression level from step (b); and
   (d) determining that the cancer has progressed when the expression level measured in step (b) is not less than the expression level measured in step (a).

4. The method of claim 3, wherein said measuring is by nucleic acid hybridization, reverse transcription-polymerase chain reaction (RT-PCR), or antibody-binding.

5. The method of claim 3, wherein the tumor sample assayed in step (b) is obtained from the patient after treatment.

6. The method of claim 5, wherein the treatment comprises cisplatin administration.

7. The method of claim 1 or 3, wherein said expression levels are determined are measured by RT-PCR, and wherein said expression levels are measured relative to expression levels of a control gene.

8. The method of claim 7, wherein the control gene is an 18S RNA gene.

9. A method of assessing treatment efficacy in an ovarian cancer patient comprising the steps of:
   (a) assaying an ovarian cancer tumor sample from the patient for an expression level of at least one gene selected from the group consisting of S100A10 and S100A11;
   (b) repeating step (a) at a subsequent time during treatment of the subject for ovarian cancer;
   (c) comparing the expression level of said at least one gene from step (a) with the gene expression level from step (b); and
   (d) determining that the treatment is efficacious when the expression level of said at least one gene in step (b) is less than the expression level in step (a).

* * * * *